(12) United States Patent
Iijima et al.

(10) Patent No.: US 9,700,389 B2
(45) Date of Patent: Jul. 11, 2017

(54) ABUTMENT, FIXTURE, DENTAL IMPLANT SET, DENTAL TAP, DENTAL GUIDE, DENTAL TAP SET AND DENTAL DRILL

(71) Applicant: Medical Corporation IT, Chiba (JP)

(72) Inventors: Toshikazu Iijima, Chiba (JP); Yasushi Nakajima, Osaka (JP)

(73) Assignee: MEDICAL CORPORATION IT, Chiba (JP)

( * ) Notice: Subject to any disclaimer, the term of this patent is extended or adjusted under 35 U.S.C. 154(b) by 72 days.

(21) Appl. No.: 14/672,583

(22) PCT Filed: Sep. 30, 2013

(86) PCT No.: PCT/IB2013/058990
§ 371 (c)(1),
(2) Date: Mar. 30, 2015

(87) PCT Pub. No.: WO2014/064558
PCT Pub. Date: May 1, 2014

(65) Prior Publication Data
US 2015/0335403 A1 Nov. 26, 2015

(30) Foreign Application Priority Data

Oct. 22, 2012 (JP) .................................. 2012-233044
Dec. 3, 2012 (WO) .................. PCT/JP2012/081268
(Continued)

(51) Int. Cl.
*A61C 8/00* (2006.01)
*A61C 1/08* (2006.01)

(52) U.S. Cl.
CPC ............ *A61C 8/0074* (2013.01); *A61C 1/084* (2013.01); *A61C 8/006* (2013.01); *A61C 8/0018* (2013.01);
(Continued)

(58) Field of Classification Search
CPC ... A61C 8/0062; A61C 8/0065; A61C 8/0066; A61C 8/0068; A61C 8/0048–8/0074
See application file for complete search history.

(56) References Cited

U.S. PATENT DOCUMENTS 4,787,848 A    11/1988  Ross
5,125,839 A *  6/1992   Ingber ................. A61C 8/0001
                                                   433/169
(Continued)

FOREIGN PATENT DOCUMENTS

DE    10-2009-031692    12/2010
EP         1224920       7/2002
(Continued)

OTHER PUBLICATIONS

JP Patent Office; Office Action dated Aug. 25, 2016 in Application No. 2015-245476 (English translation).
(Continued)

*Primary Examiner* — Michael Kahelin
(74) *Attorney, Agent, or Firm* — Snell & Wilmer L.L.P.

(57) ABSTRACT

An abutment is obtained that enables an operation of detaching the abutment from a fixture to be readily performed without having a patient open his/her mouth wide while inhibiting accidental ingestion or swallowing of an abutment that comes off. In a dental implant 100 comprising a fixture 110 and an abutment 120, when a fitting recess 121 of the abutment 120 is fitted onto a fixture head 112 so that a space is formed between a top surface 112*b* 1 of the fixture head 112 and a bottom surface 121*a* of the fitting recess 121, the fixture head 112 is secured to the fitting recess 121 by a frictional force, and an instrument insertion hole 129 for inserting an instrument for disengaging the securement by the frictional force in the space is formed on a sidewall 121*c* of the fitting recess 121.

12 Claims, 34 Drawing Sheets

(30) Foreign Application Priority Data

Feb. 28, 2013 (JP) .................. 2013-038299
Aug. 20, 2013 (JP) .................. 2013-170439

(52) U.S. Cl.
CPC .......... *A61C 8/0066* (2013.01); *A61C 8/0078* (2013.01); *A61C 8/0089* (2013.01); *A61C 8/0048* (2013.01); *A61C 8/0095* (2013.01)

(56) References Cited

U.S. PATENT DOCUMENTS

| | | |
|---|---|---|
| 5,417,570 A | 5/1995 | Zuest et al. |
| 2007/0224574 A1 | 9/2007 | Poirier |
| 2010/0081107 A1 | 4/2010 | Bagambisa |
| 2011/0136076 A1* | 6/2011 | Li .................. A61C 5/04 433/167 |
| 2011/0287381 A1 | 11/2011 | Sanders |
| 2011/0311947 A1 | 12/2011 | Schoene et al. |

FOREIGN PATENT DOCUMENTS

| | | |
|---|---|---|
| EP | 2168529 | 3/2010 |
| EP | 2324795 | 5/2011 |
| FR | 2902311 | 12/2007 |
| GB | 2119258 | 11/1983 |
| JP | 6349155 | 3/1988 |
| JP | 63169115 | 11/1988 |
| JP | 2002-153493 | 5/2002 |
| JP | 2003-521330 | 7/2003 |
| JP | 2005276109 | 10/2005 |
| JP | 2006-505339 | 2/2006 |
| JP | 2007-515198 | 6/2007 |
| JP | 2010521269 | 6/2010 |
| JP | 2011-72773 | 4/2011 |
| WO | 99/39651 | 8/1999 |
| WO | 2008/088105 | 7/2008 |
| WO | 2010/028811 | 3/2010 |
| WO | 2011027689 | 3/2011 |

OTHER PUBLICATIONS

International Search Report in Application No. PCT/IB2013/058990 dated Aug. 28, 2014.
International Search Report in Application No. PCT/JP2012/081268 dated Feb. 26, 2013.
Office Action dated Oct. 13, 2016 in Japanese Application No. 2015-245475.

* cited by examiner

[Fig. 1]
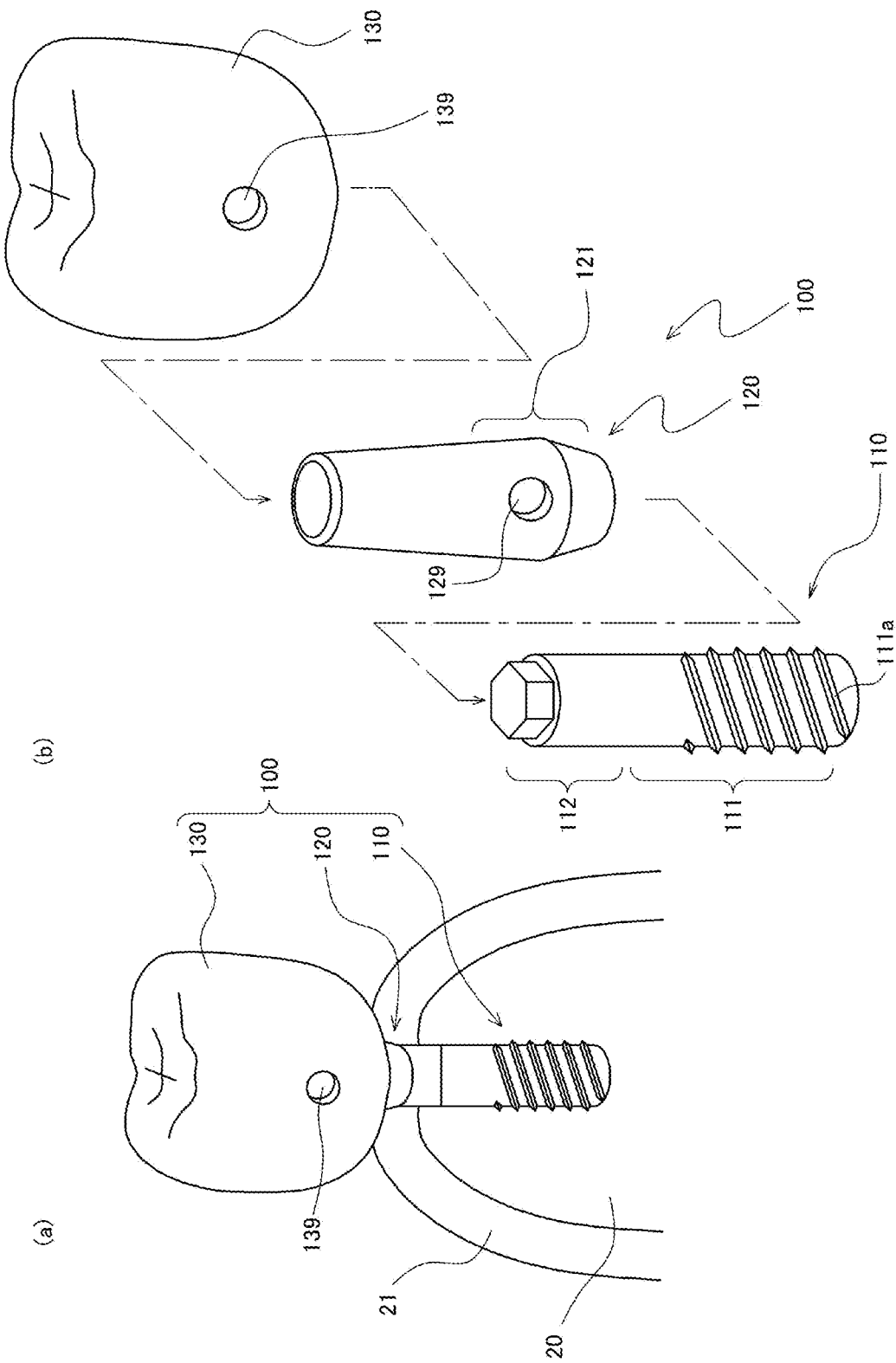

[Fig. 2]
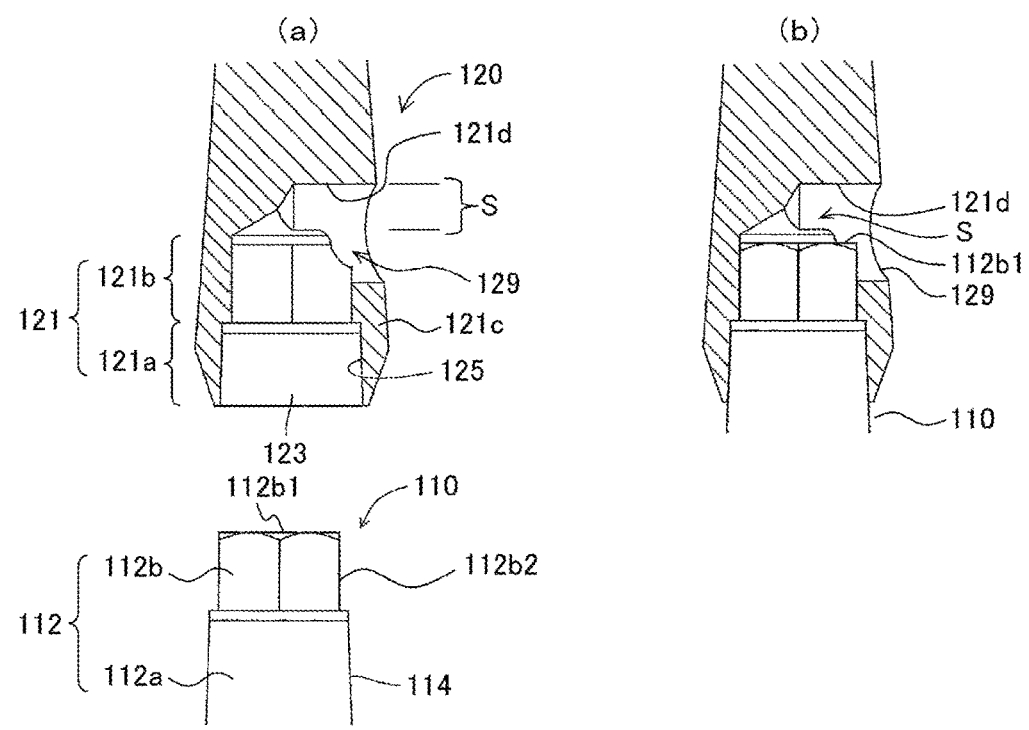

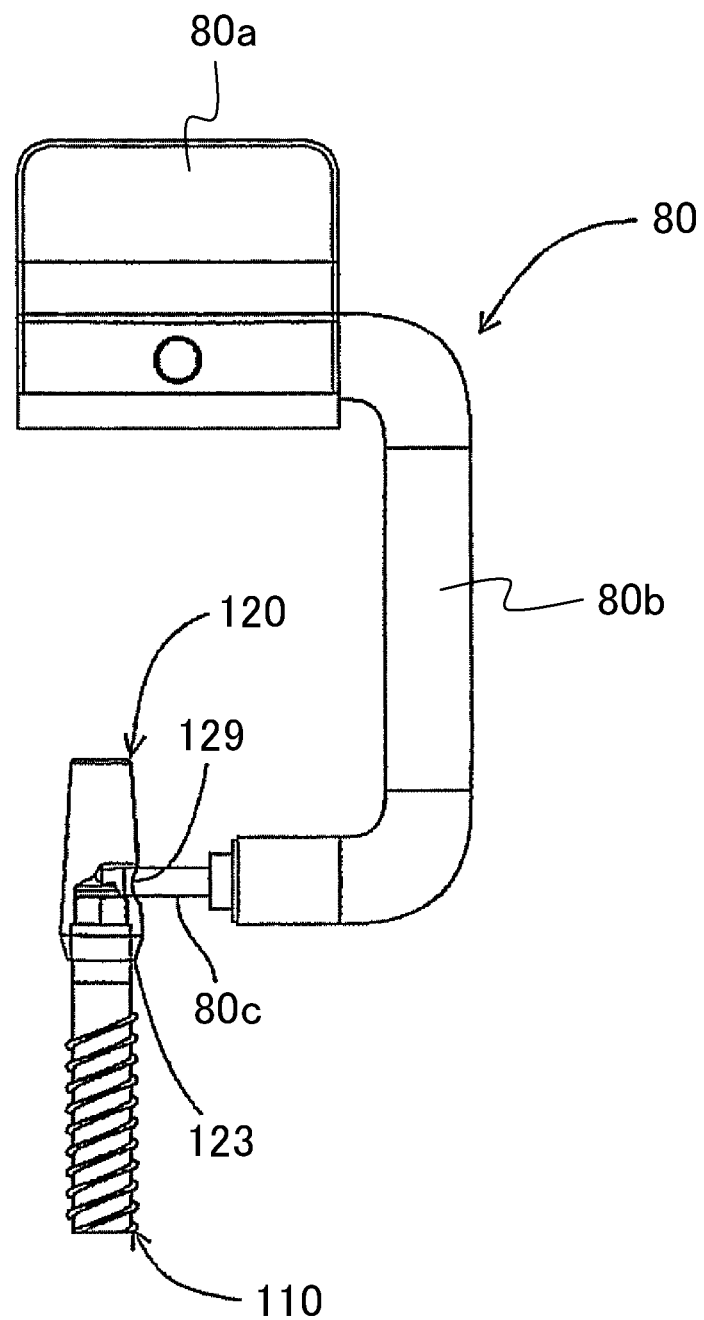
[Fig. 3]

[Fig. 4]
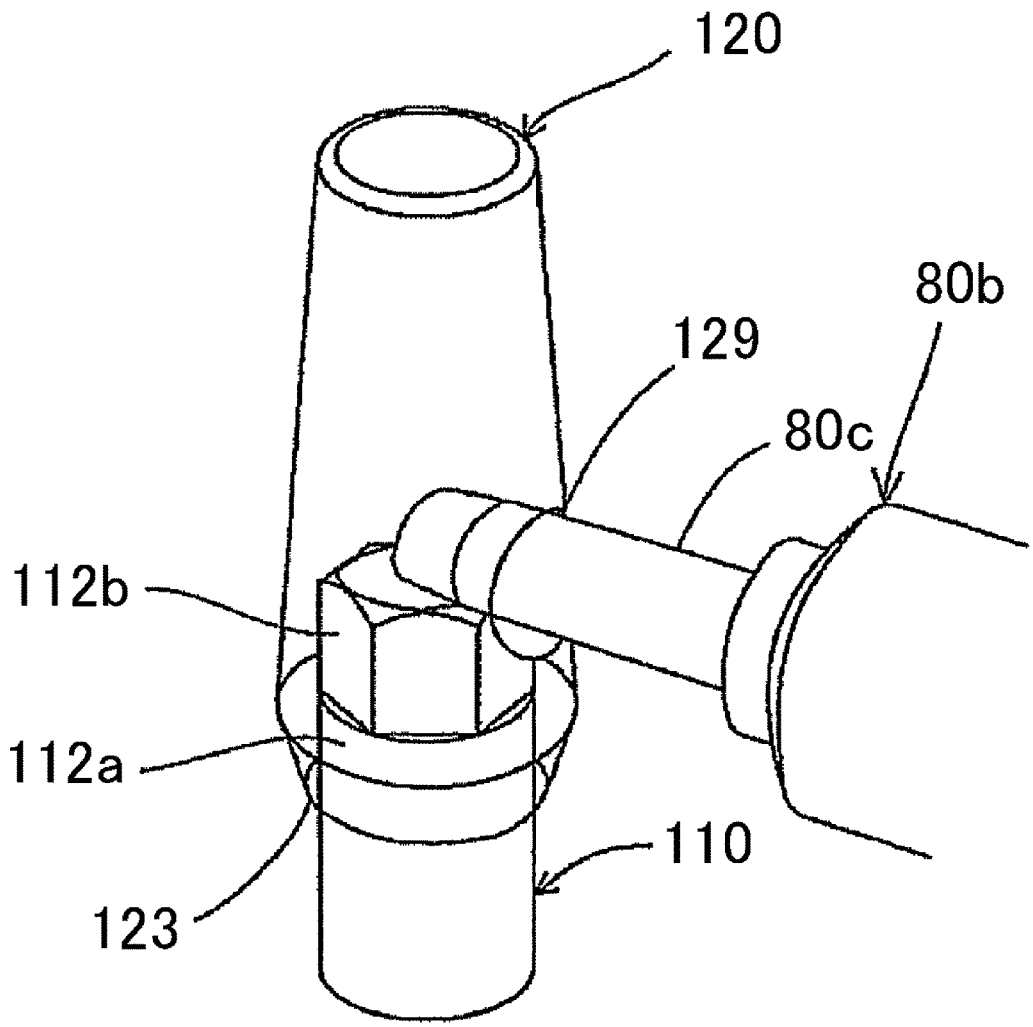
[Fig. 5]
(a) 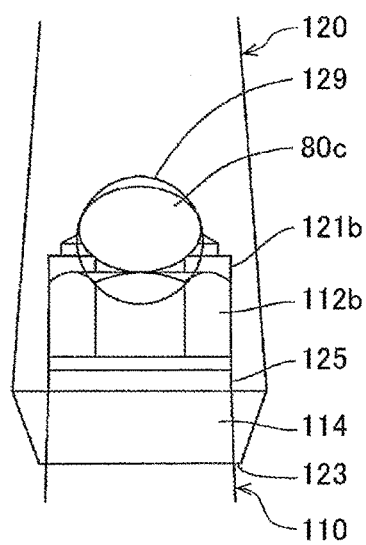  (b) 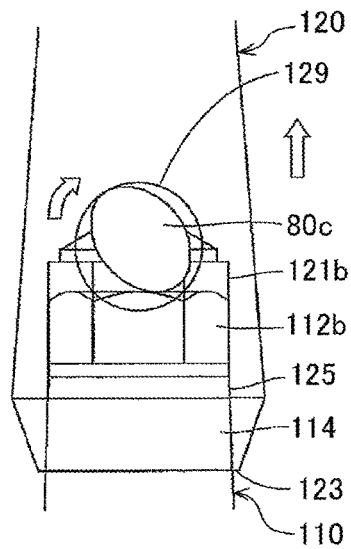

[Fig. 6]
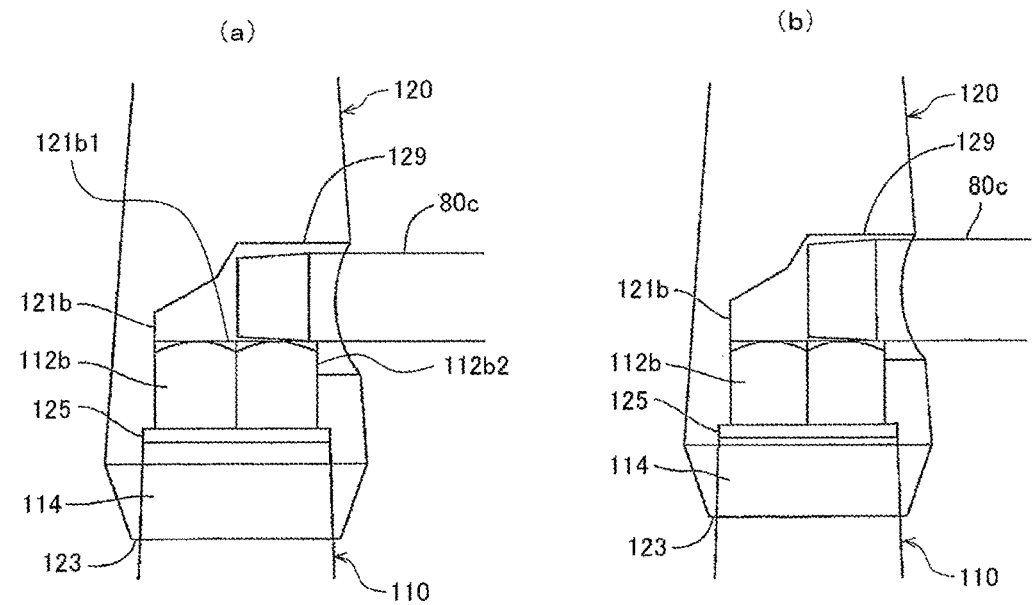
[Fig. 7]
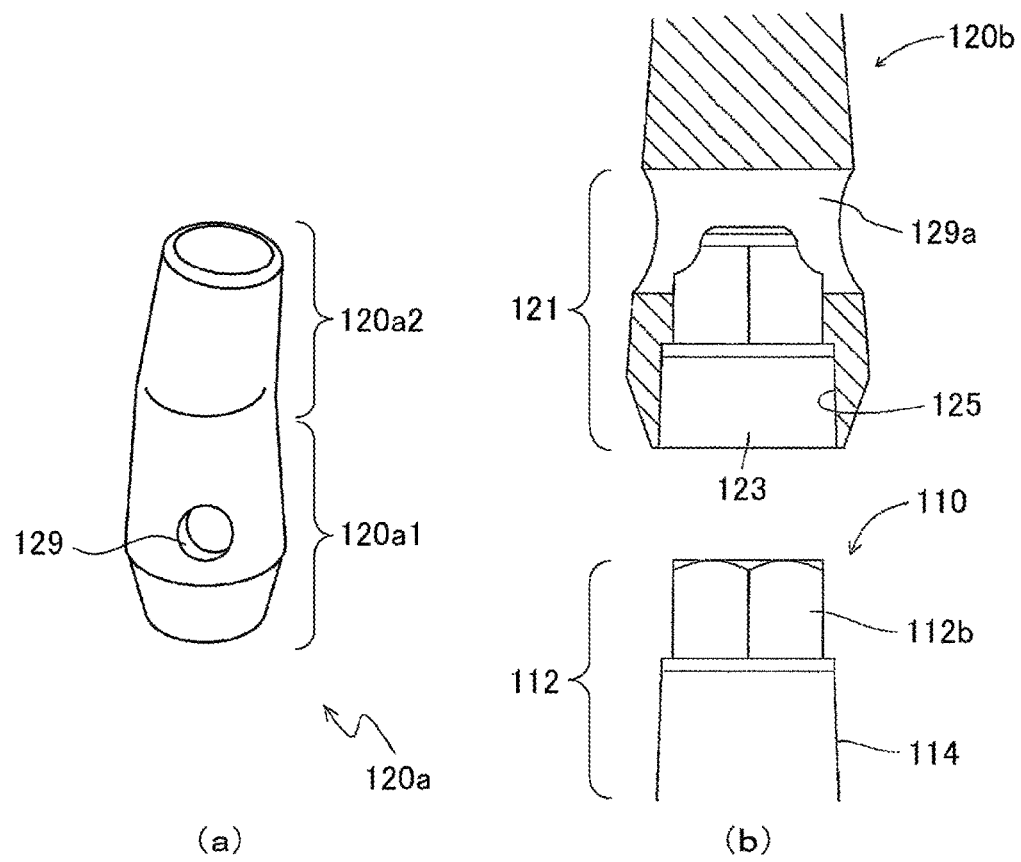

[Fig. 8]
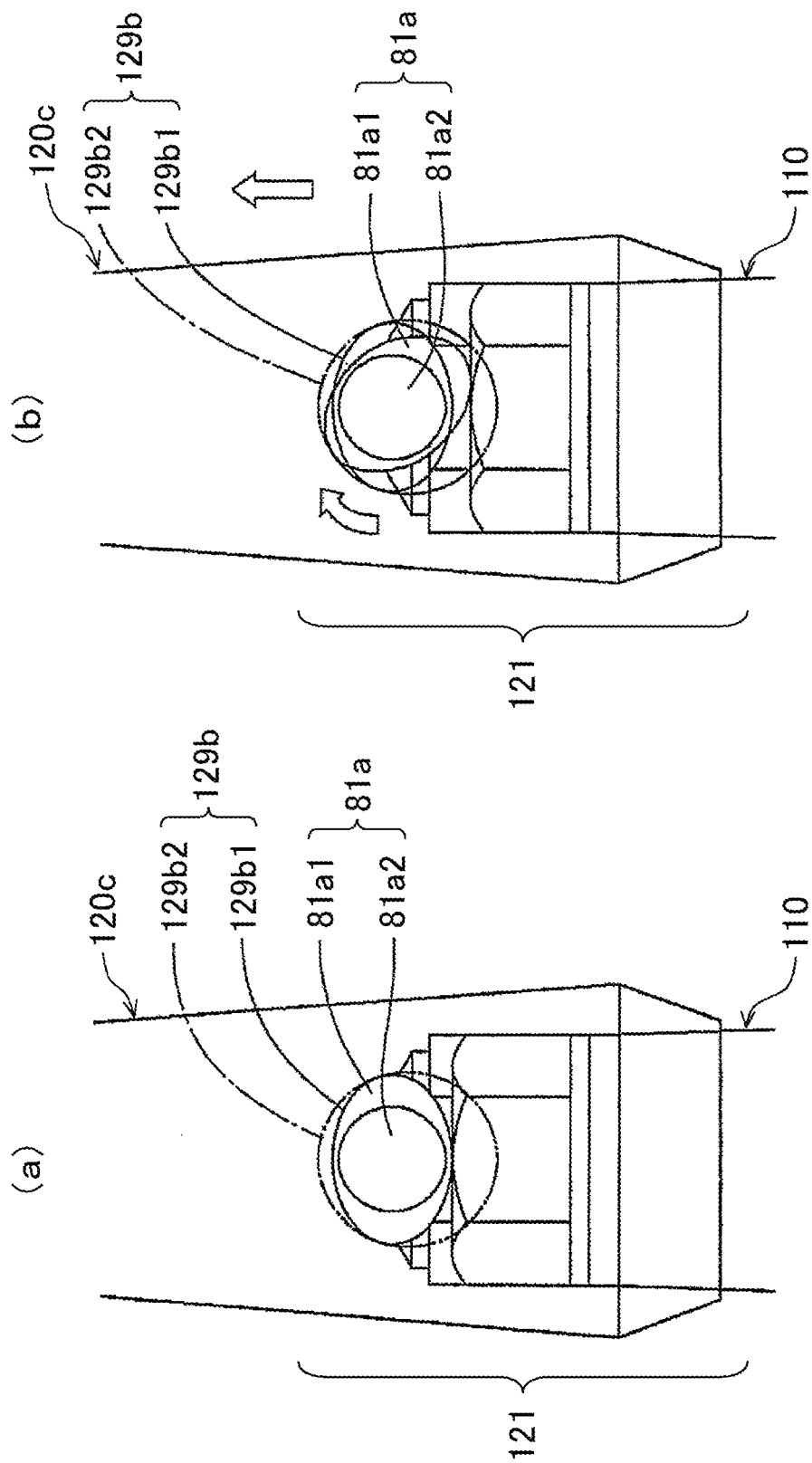

[Fig. 9]
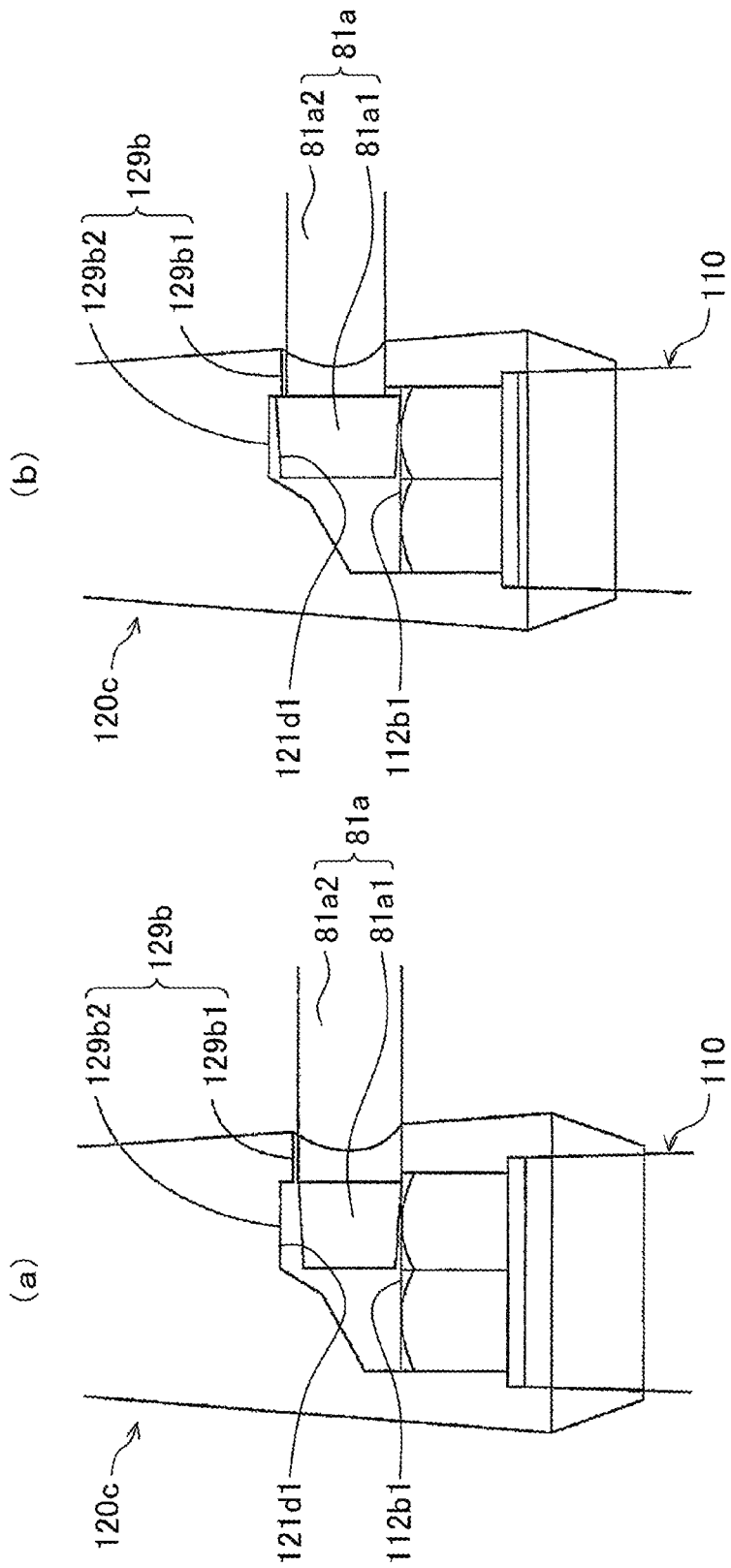

[Fig. 10]
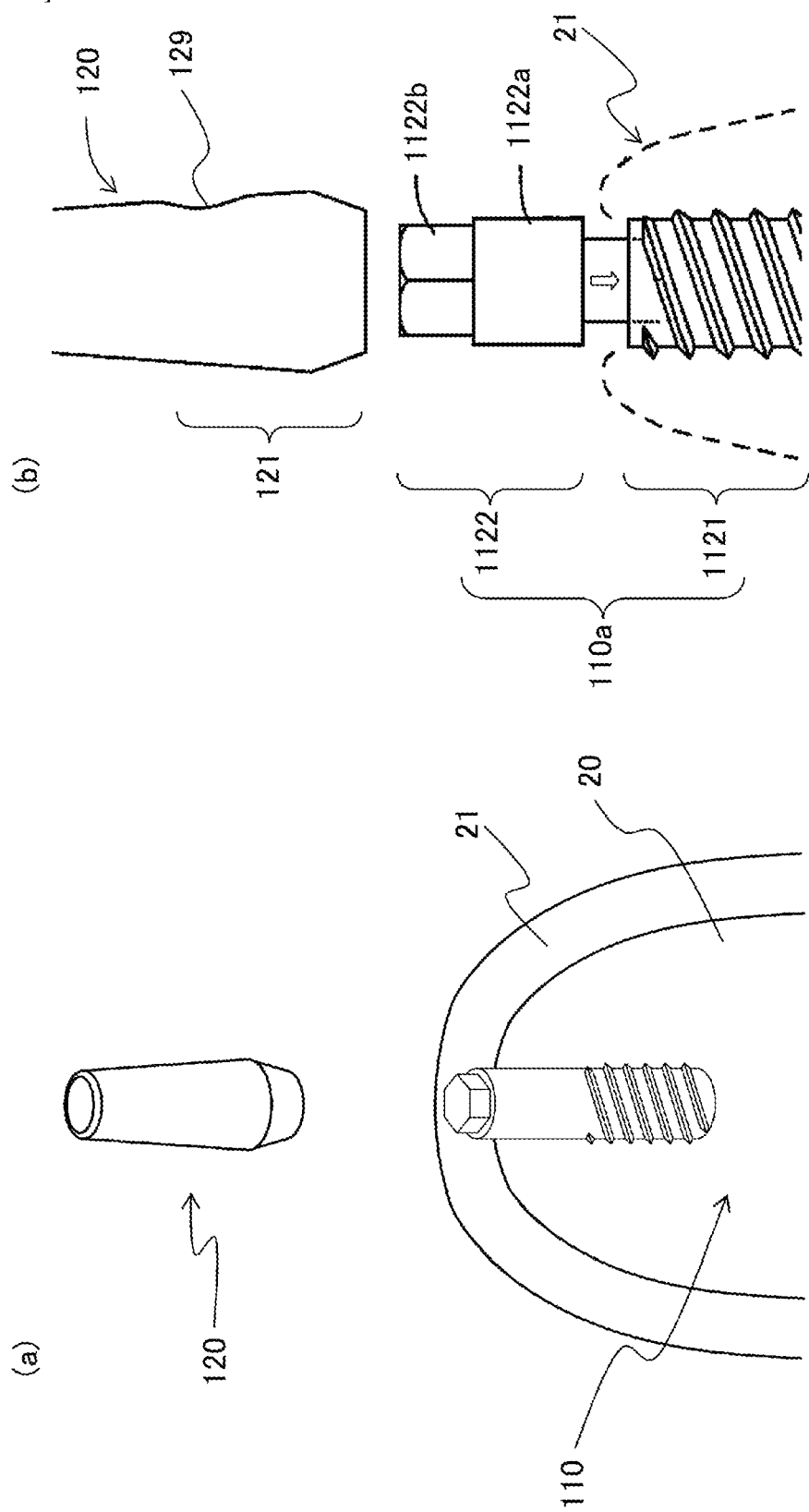

[Fig. 11]
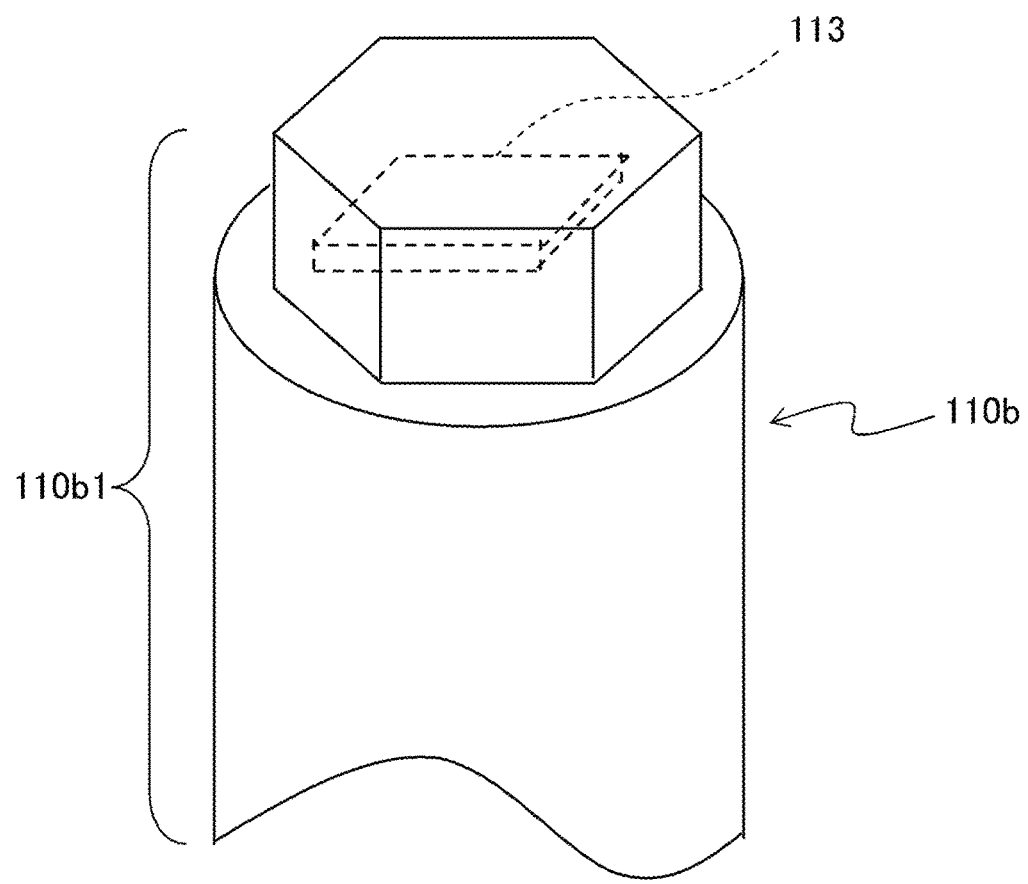

[Fig. 12]
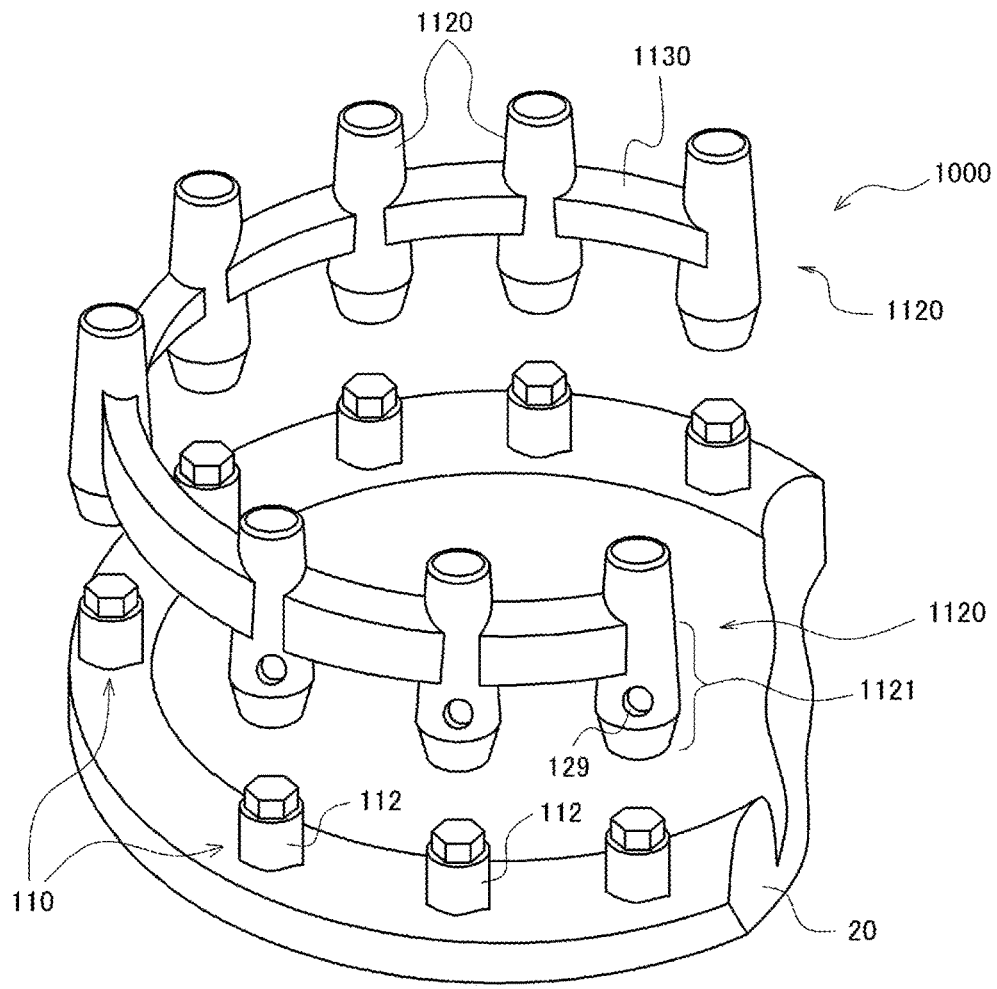

[Fig. 13]
(a)  (b)
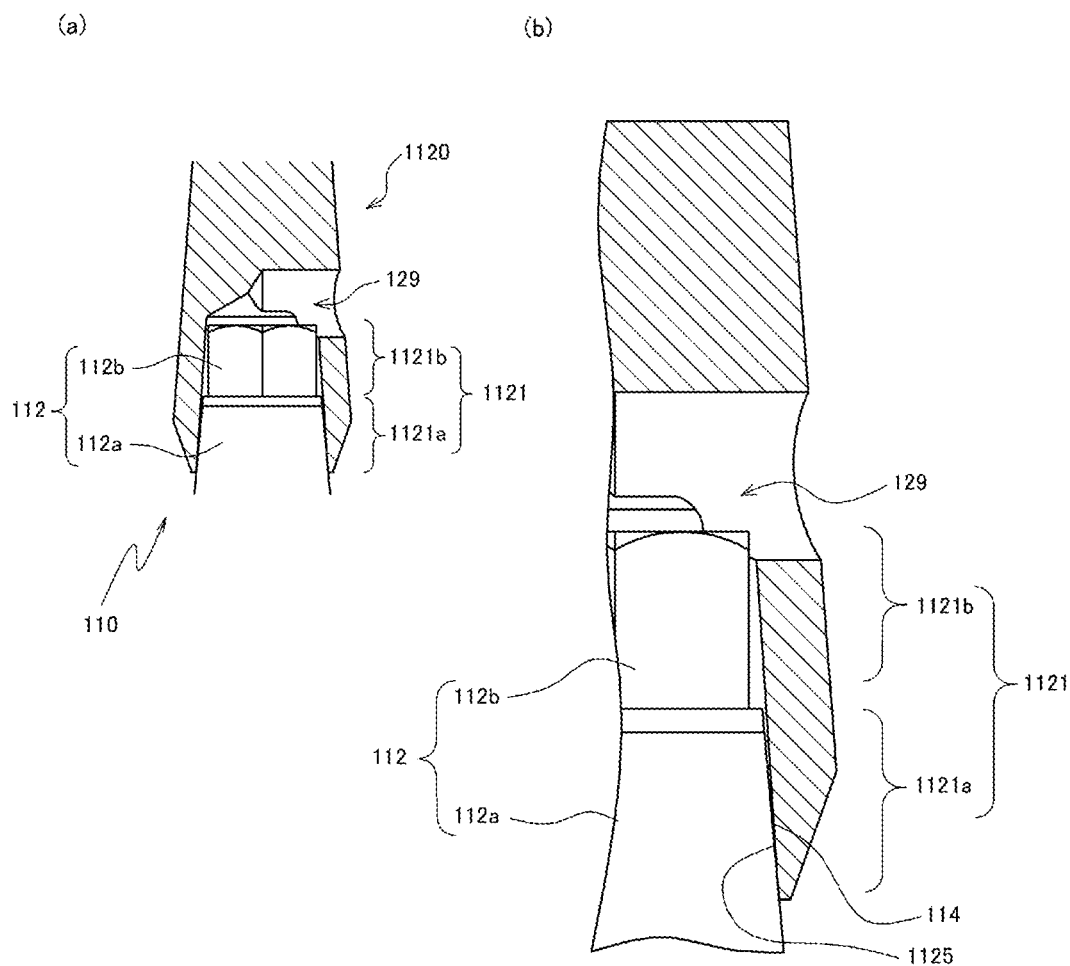

[Fig. 14]
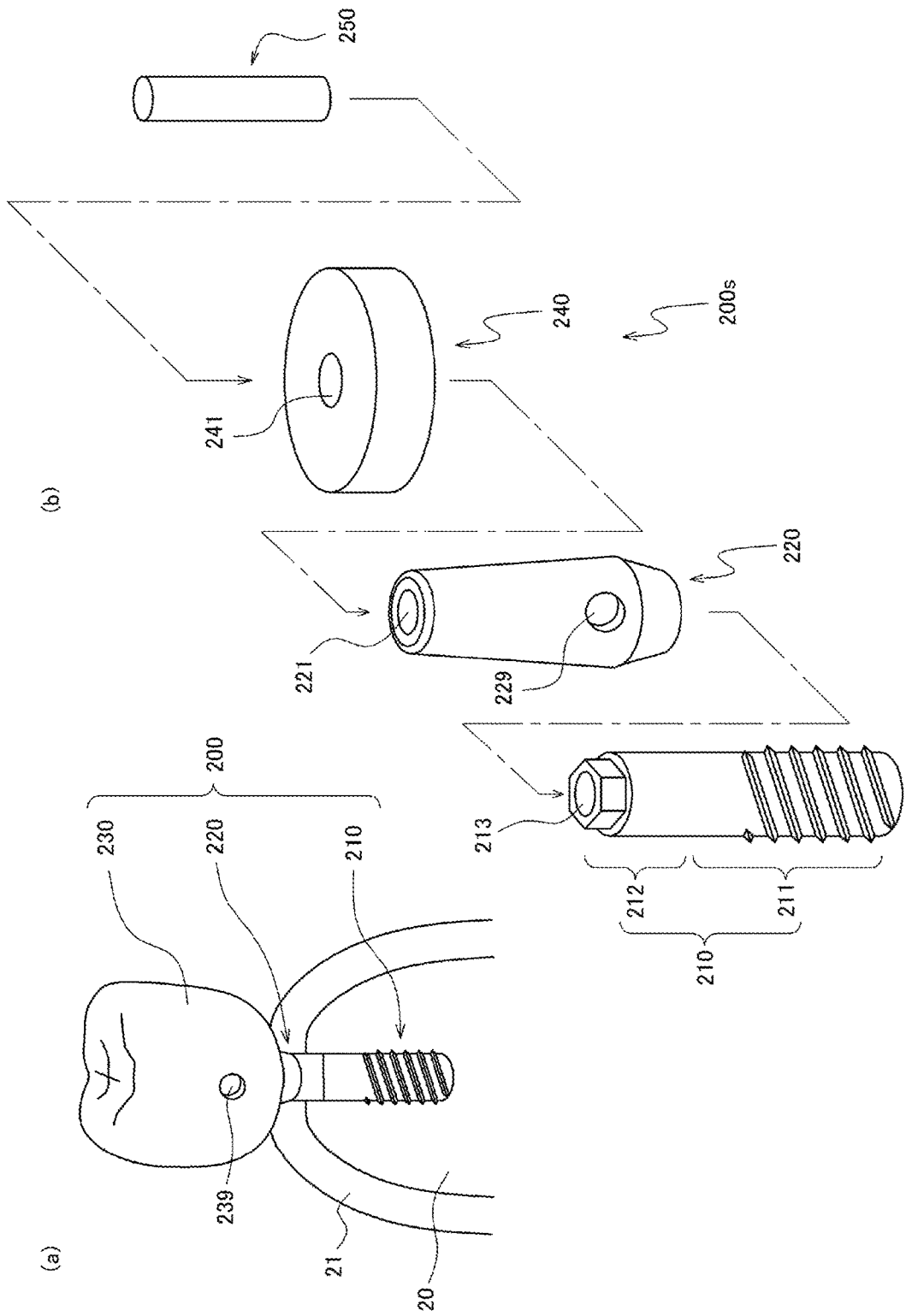

[Fig. 15]
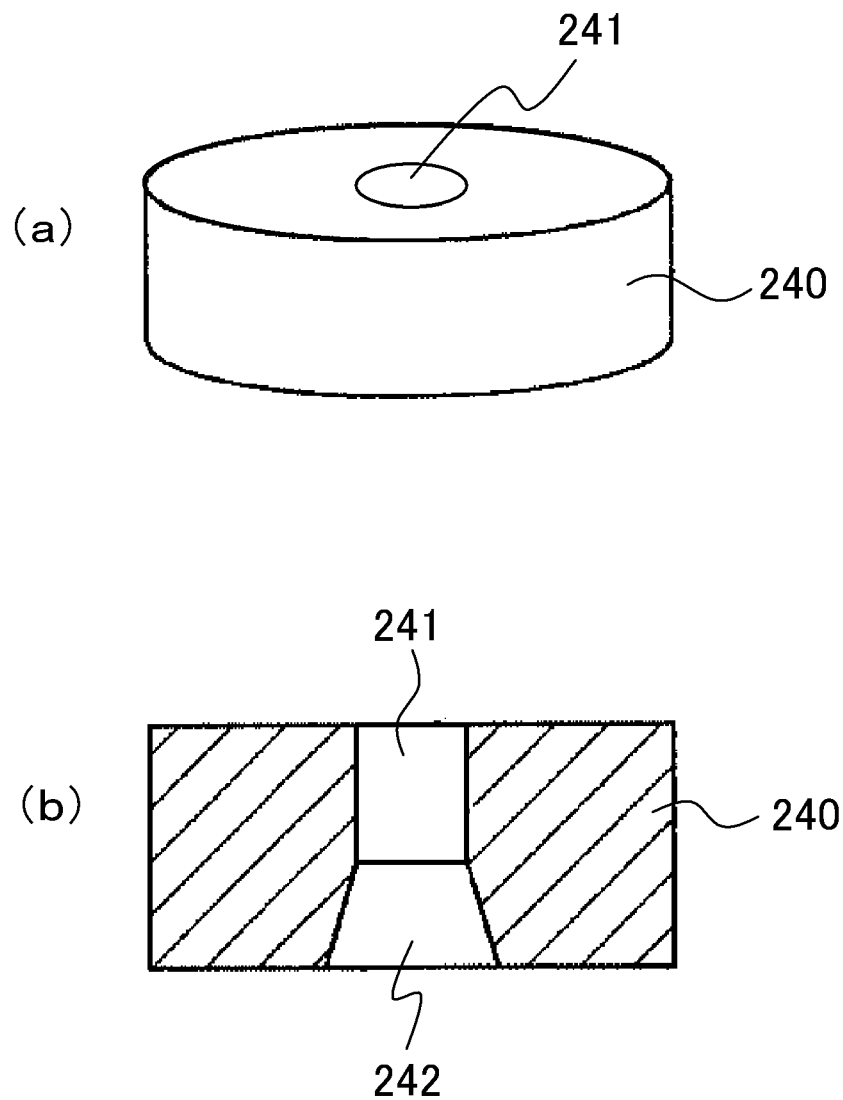

[Fig. 16]
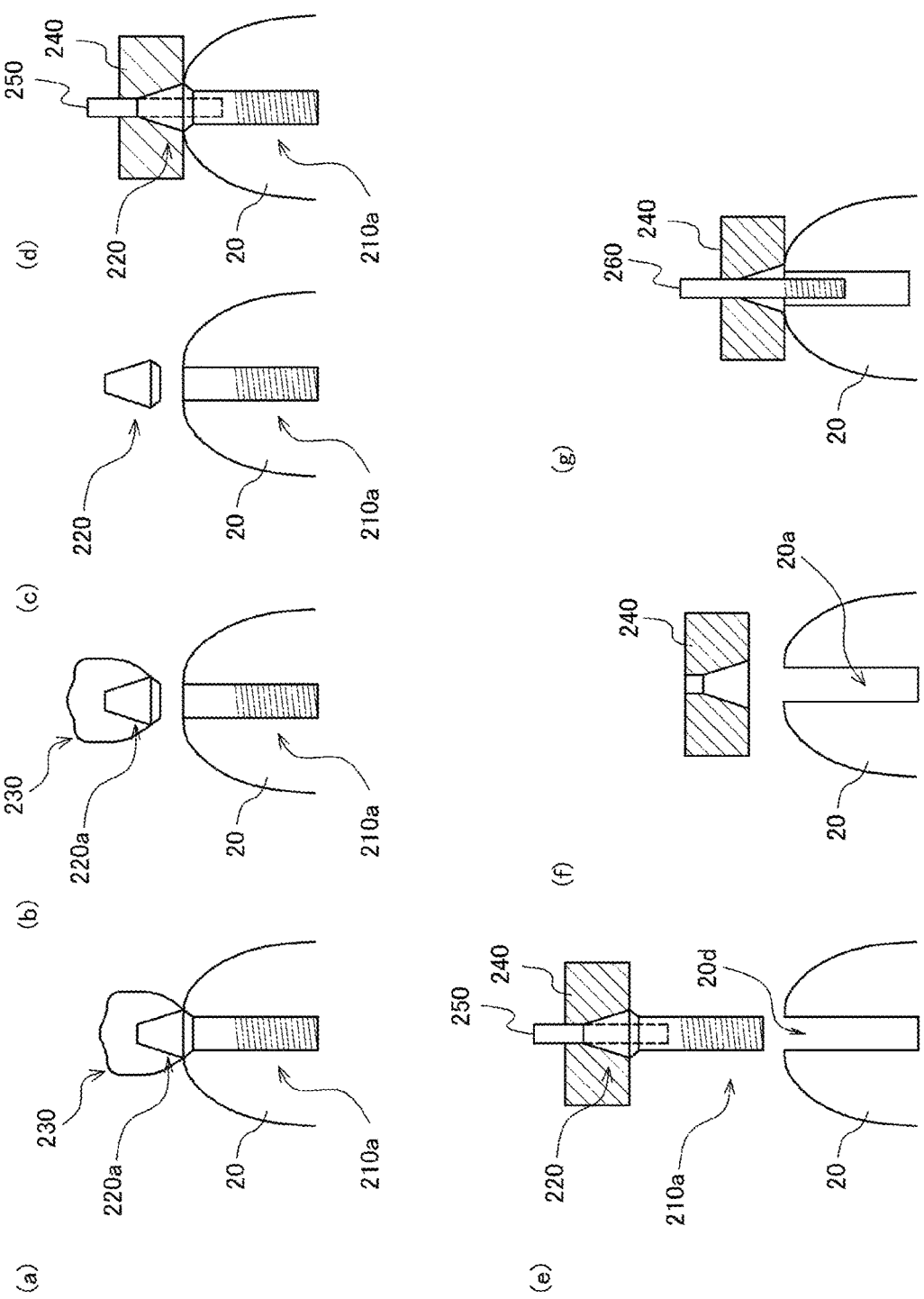

[Fig. 17]
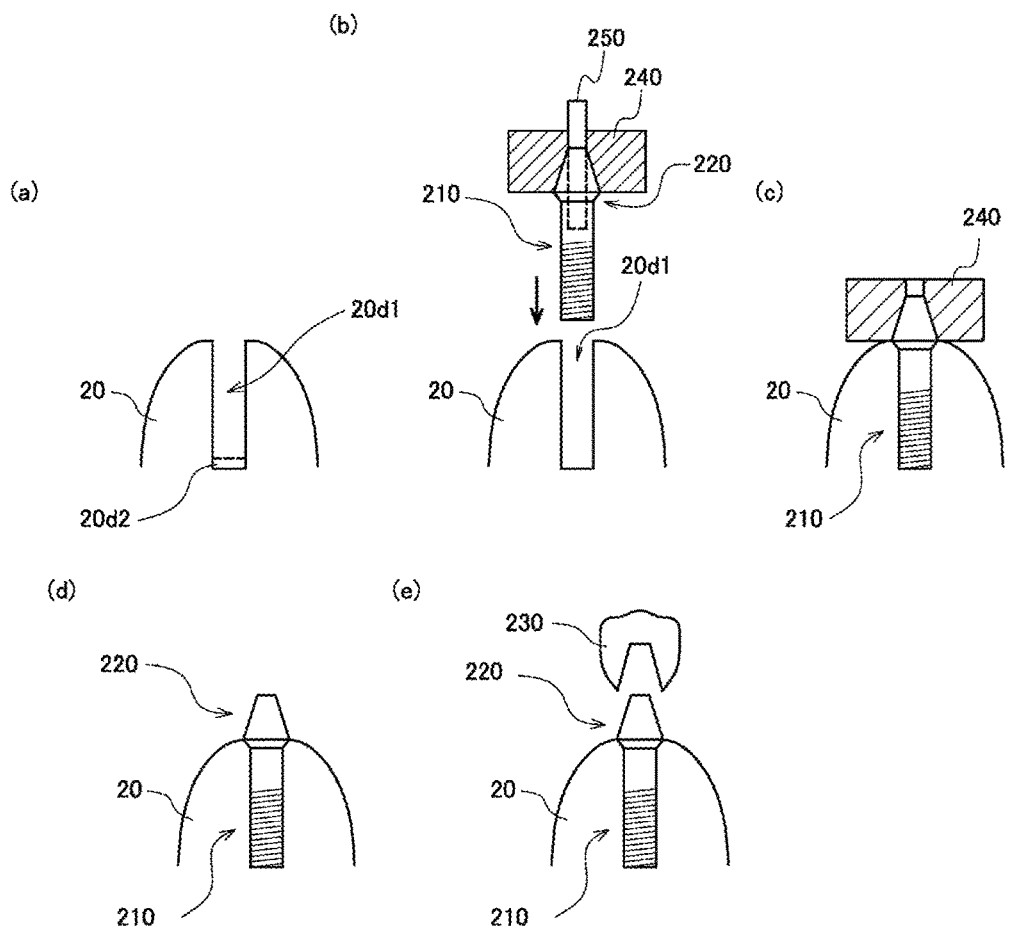
[Fig. 18]
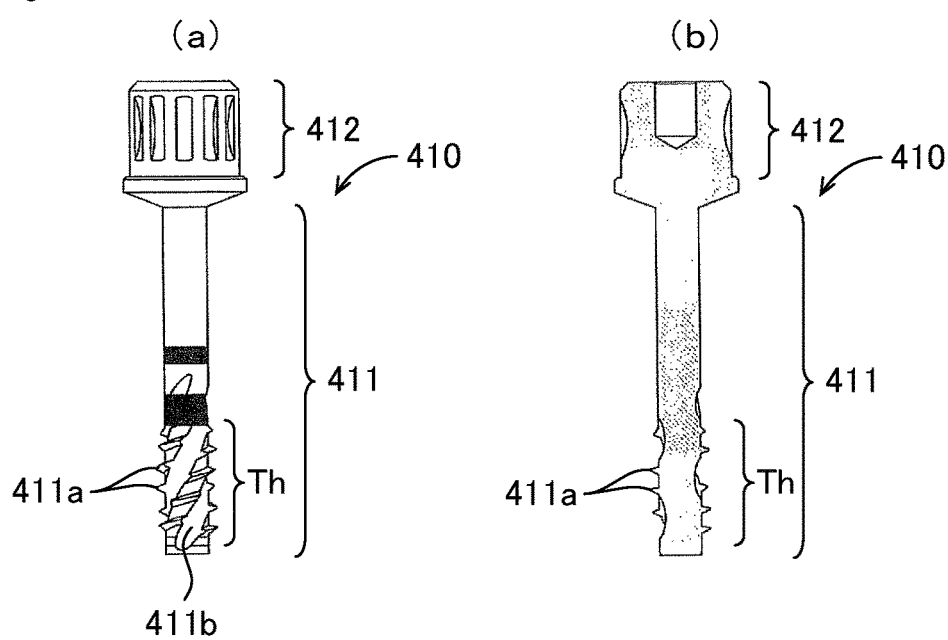

[Fig. 19]
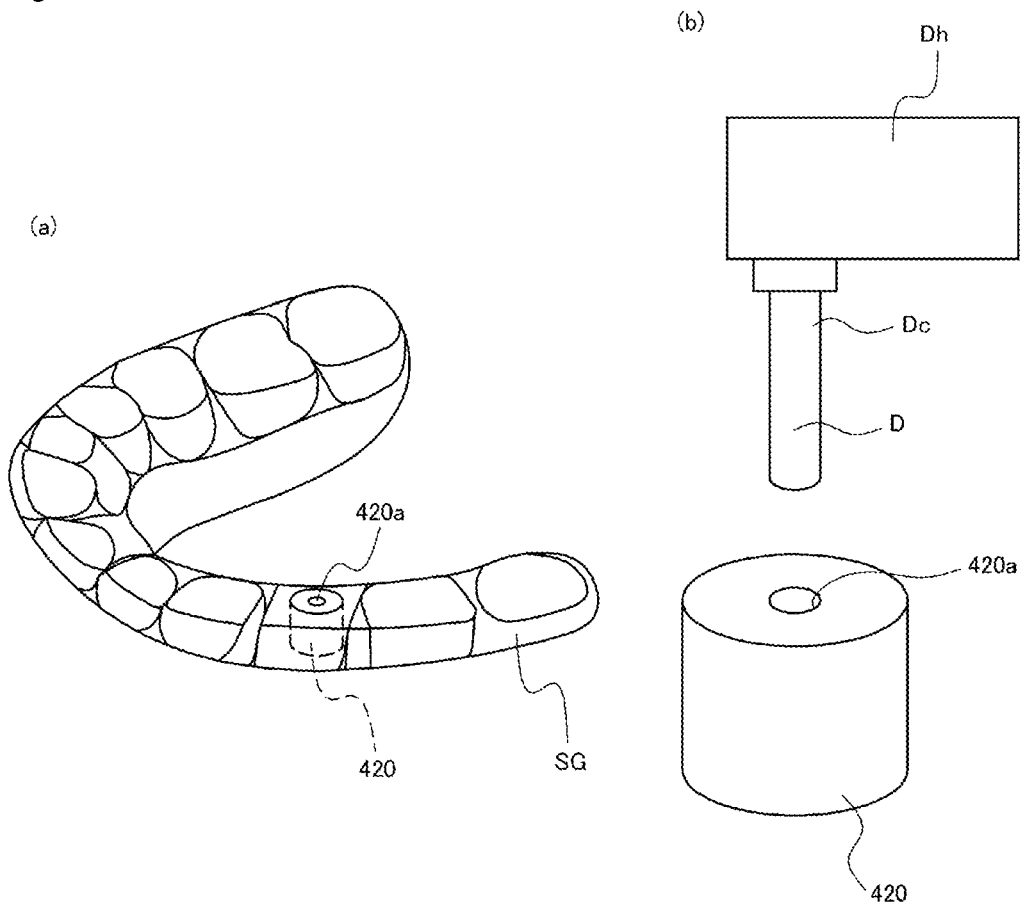
[Fig. 20]
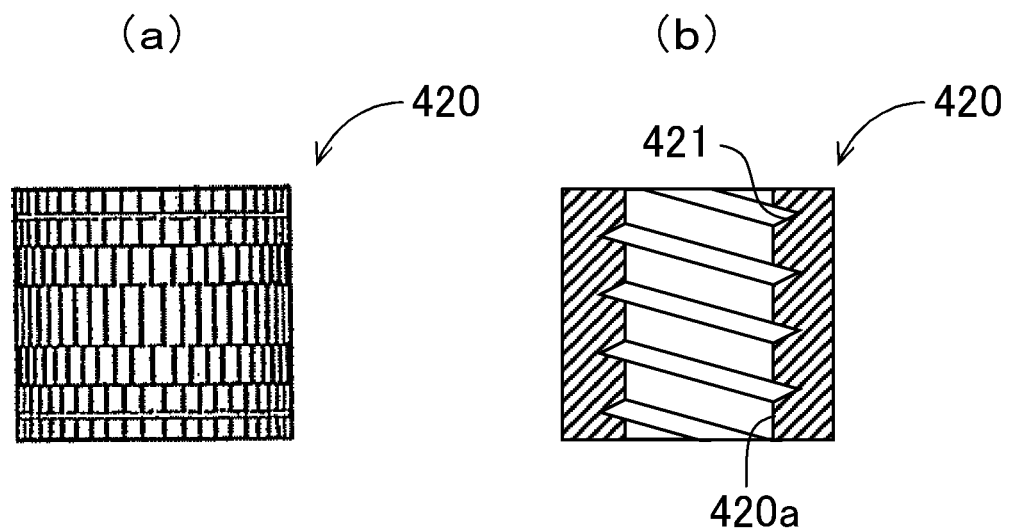

[Fig. 21]
(a) 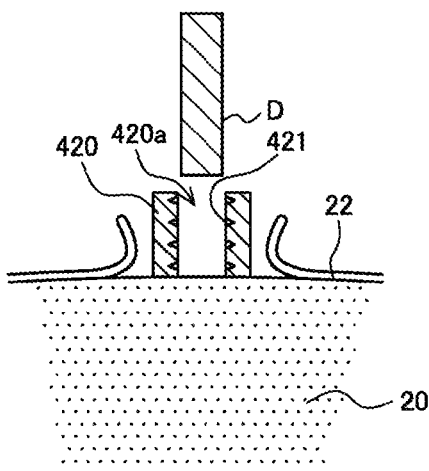
(b) 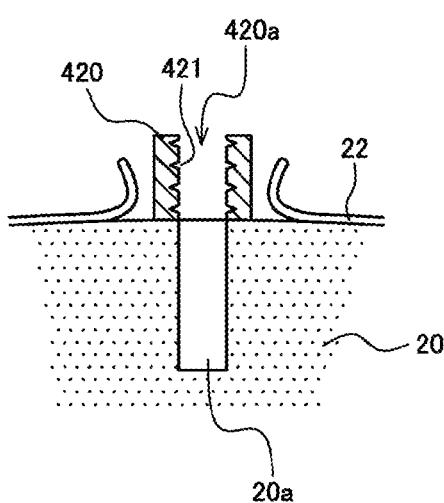
(c) 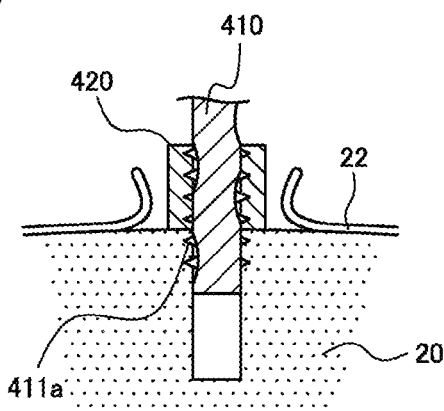
(d) 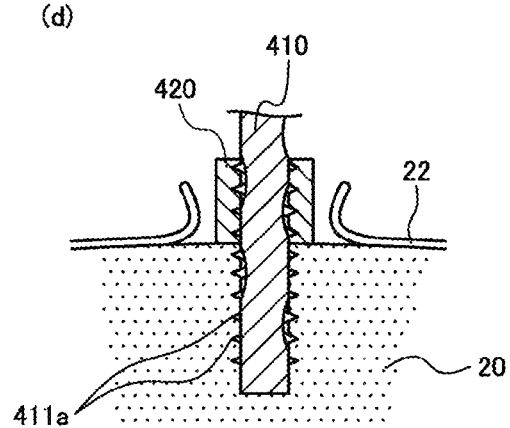
(e) 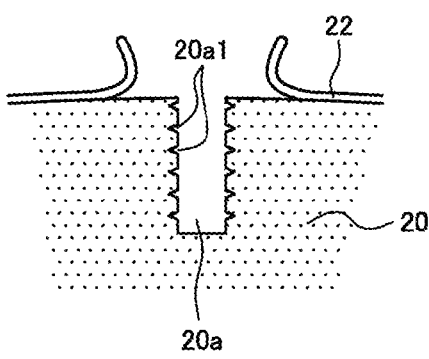
(f) 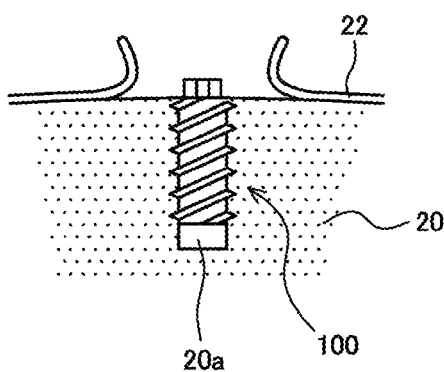

[Fig. 22]
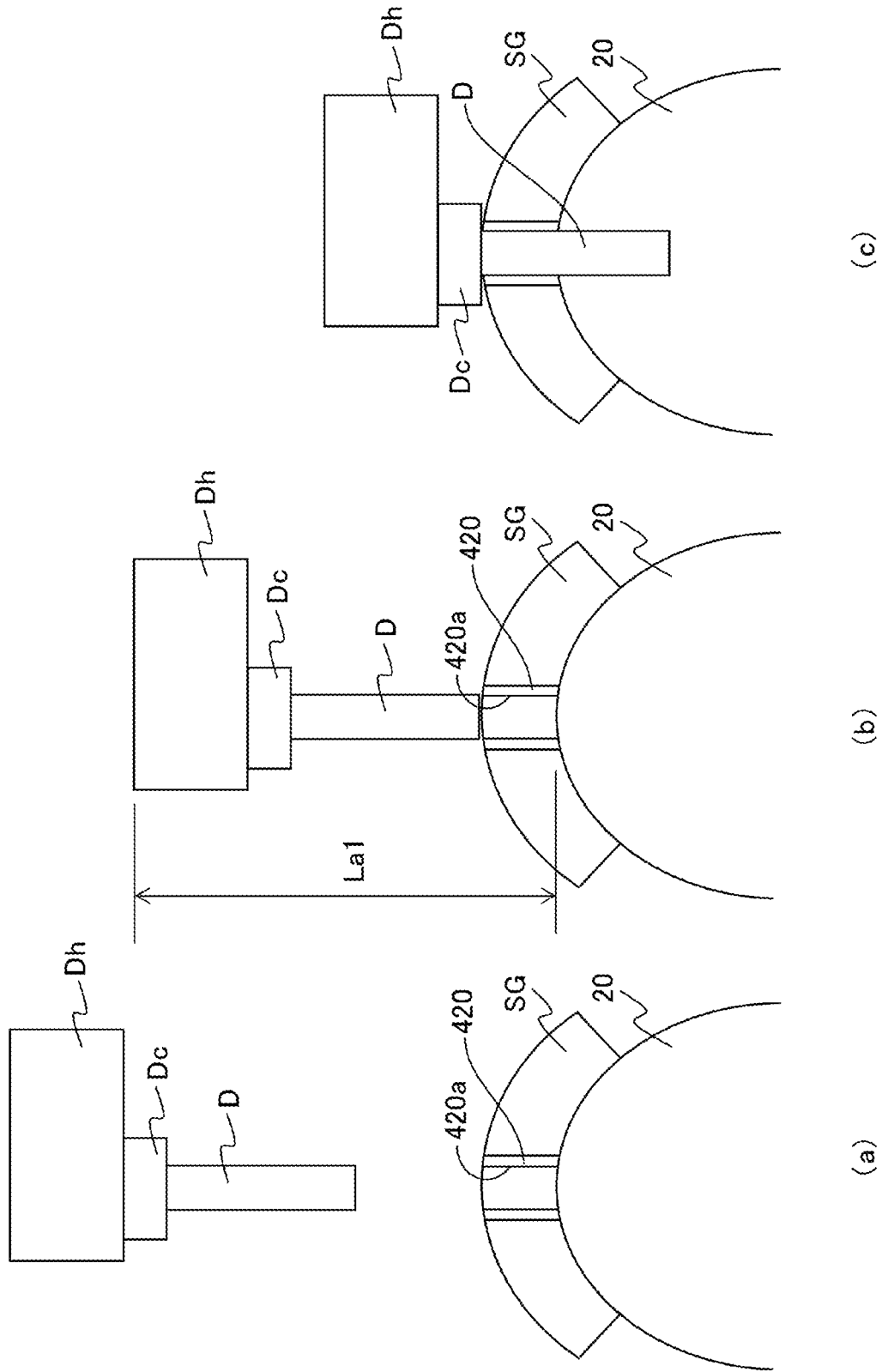

[Fig. 23]
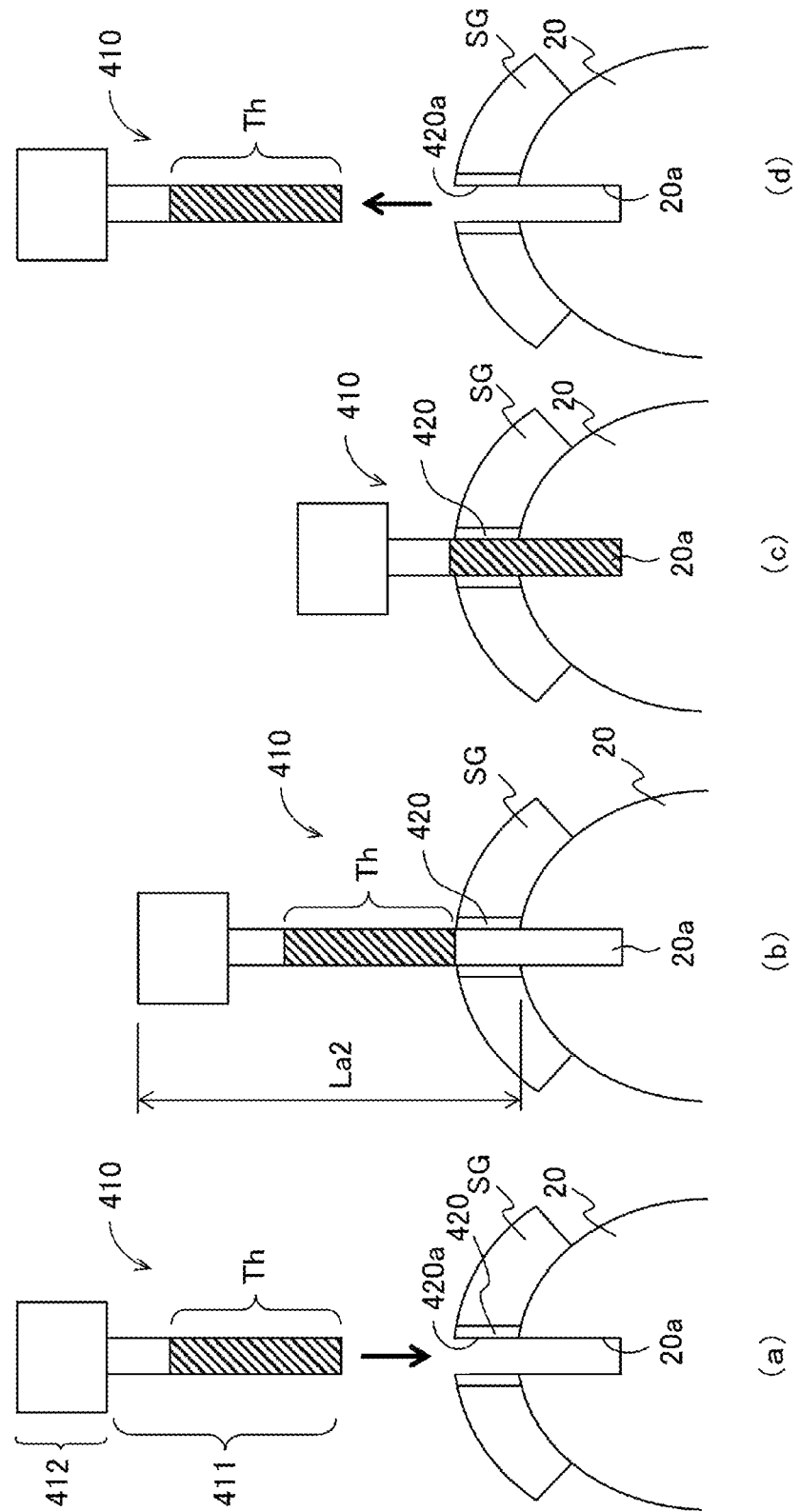

[Fig. 24]
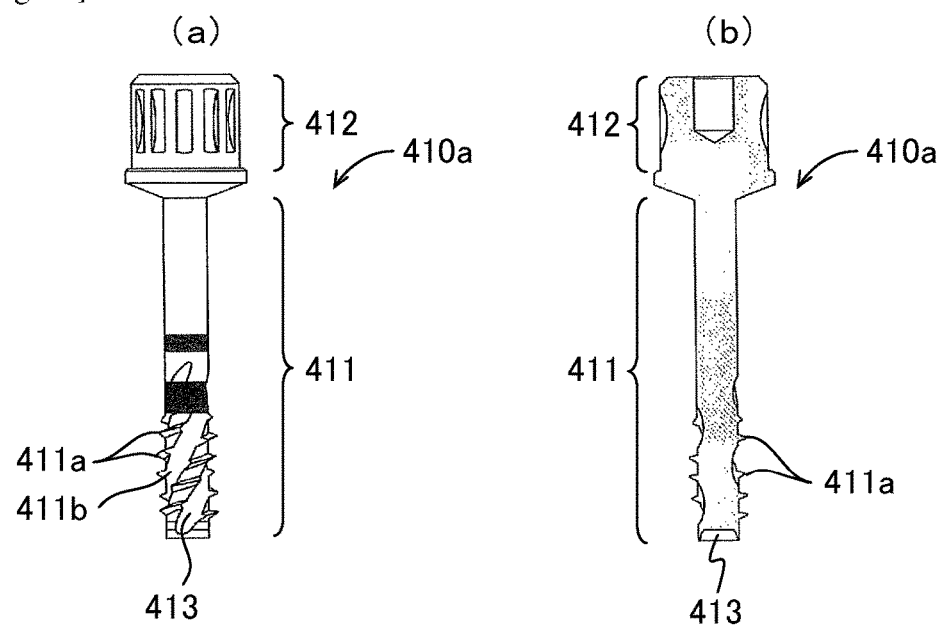

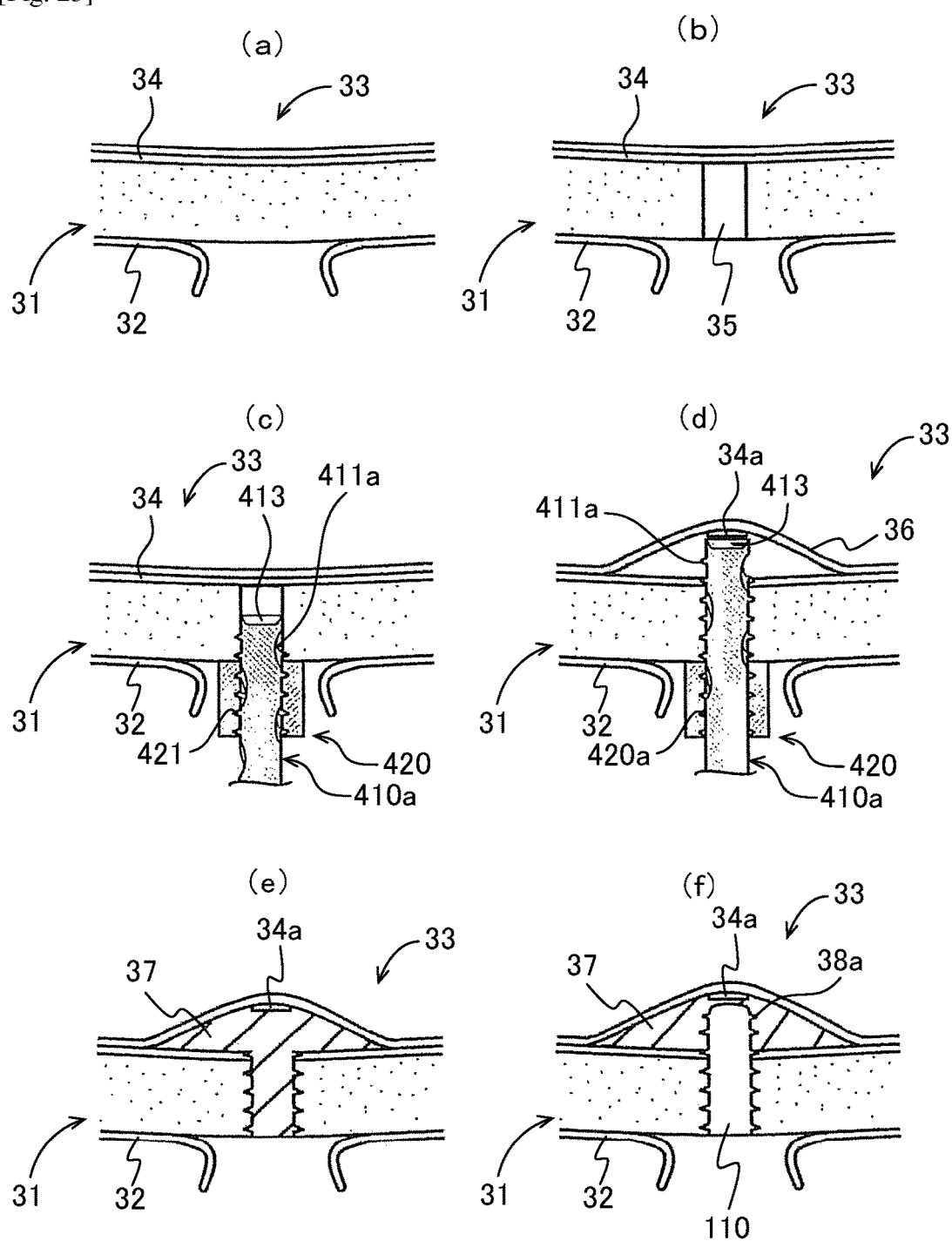
[Fig. 25]

[Fig. 26]
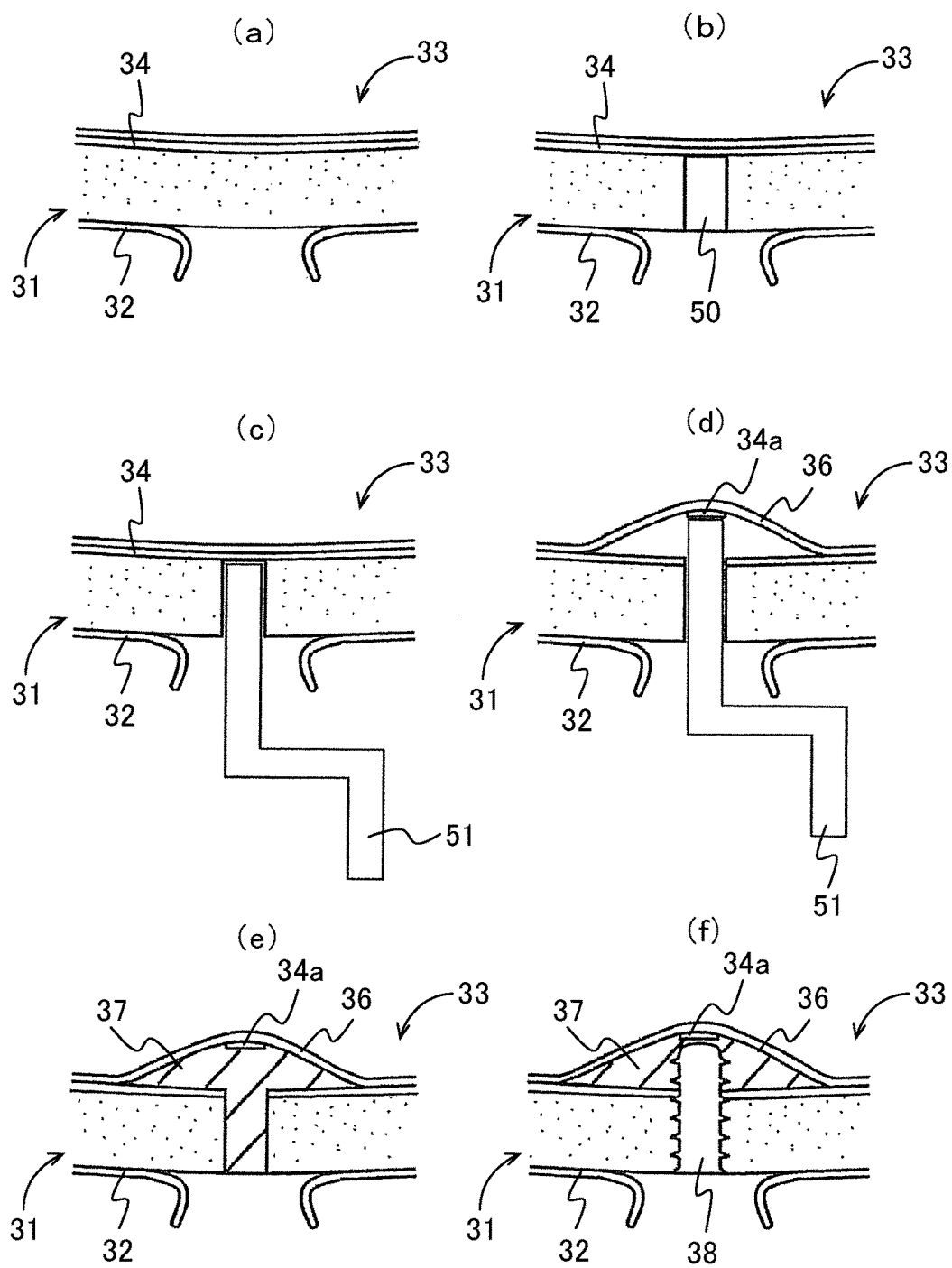

[Fig. 27]
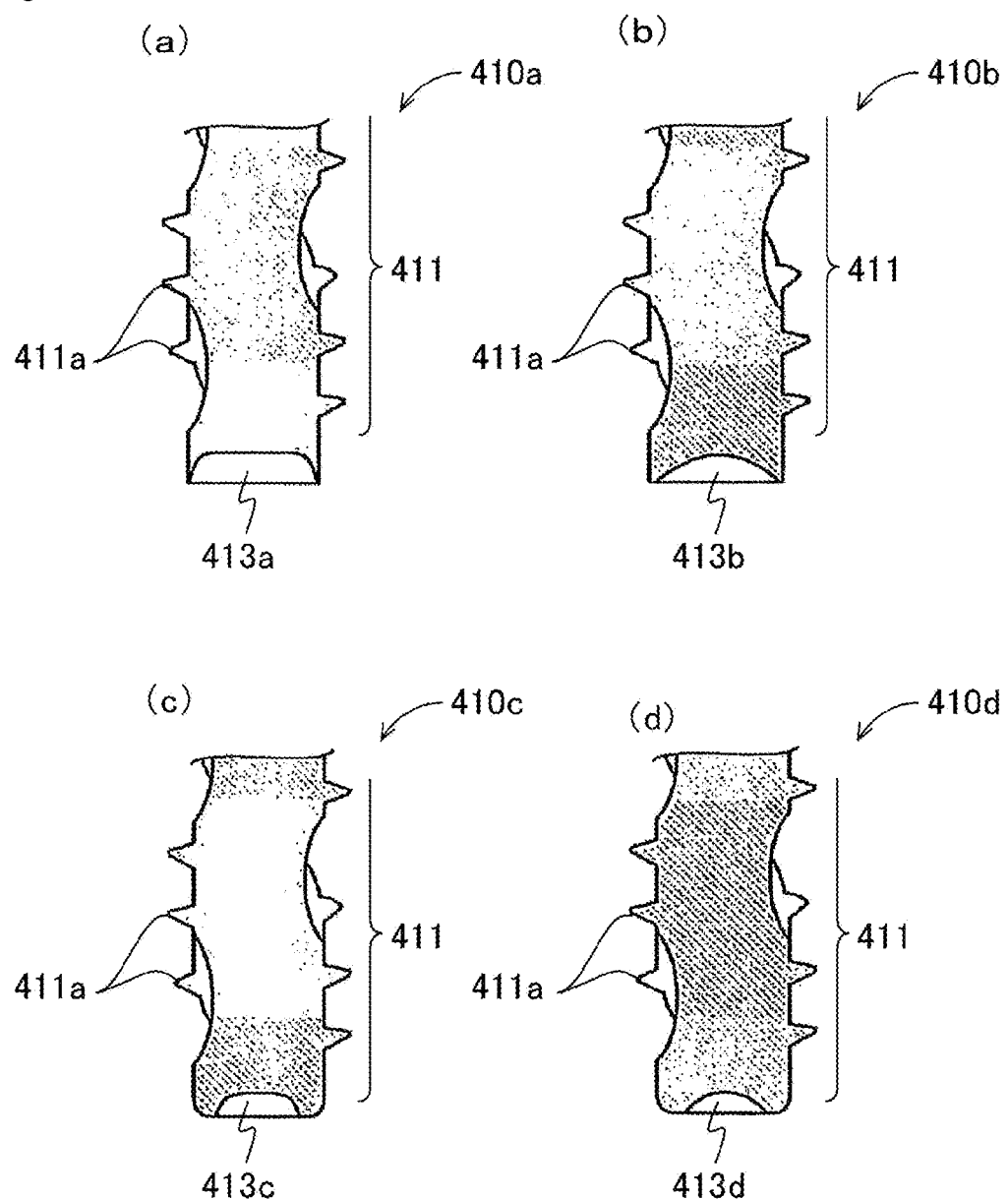

[Fig. 28]
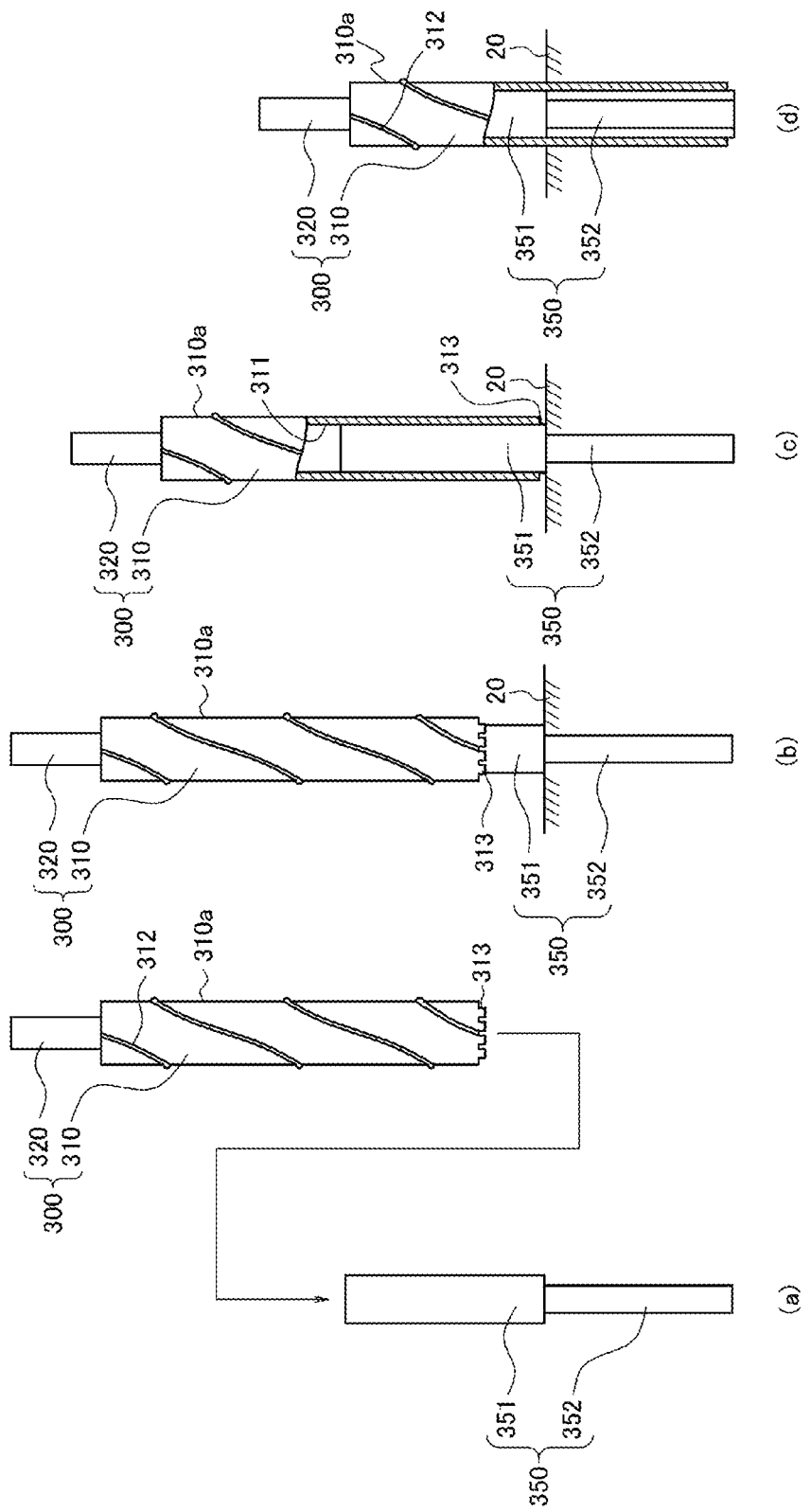

[Fig. 29]
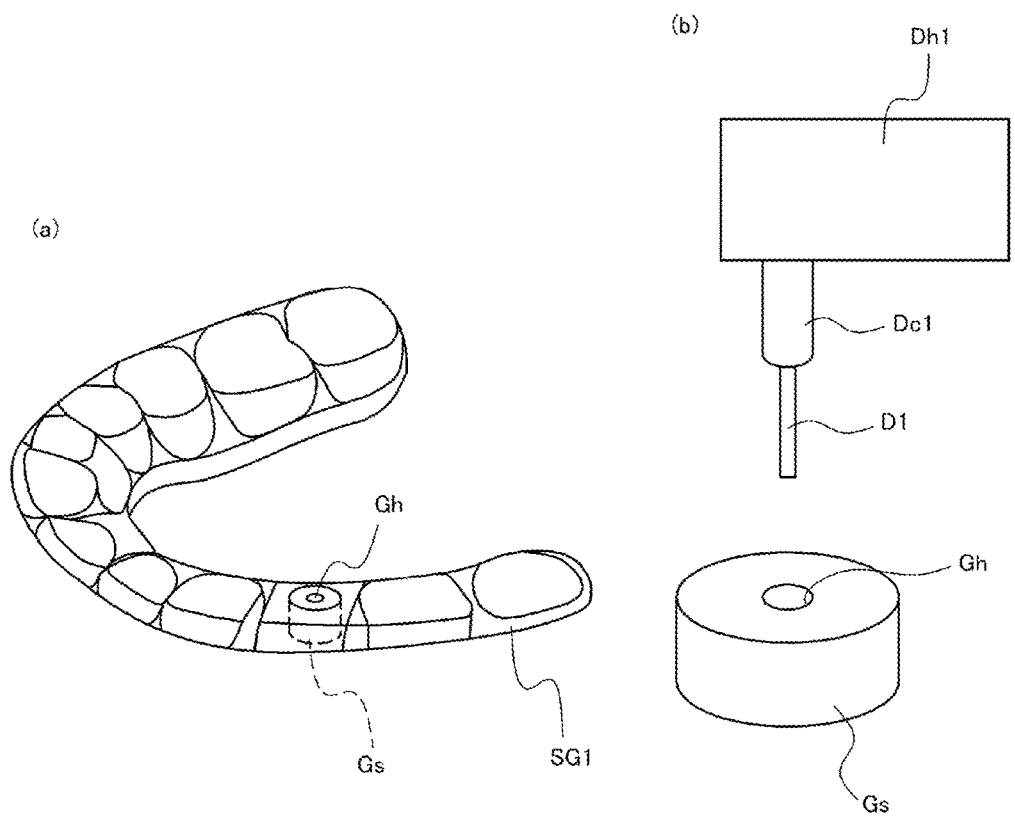

[Fig. 30]
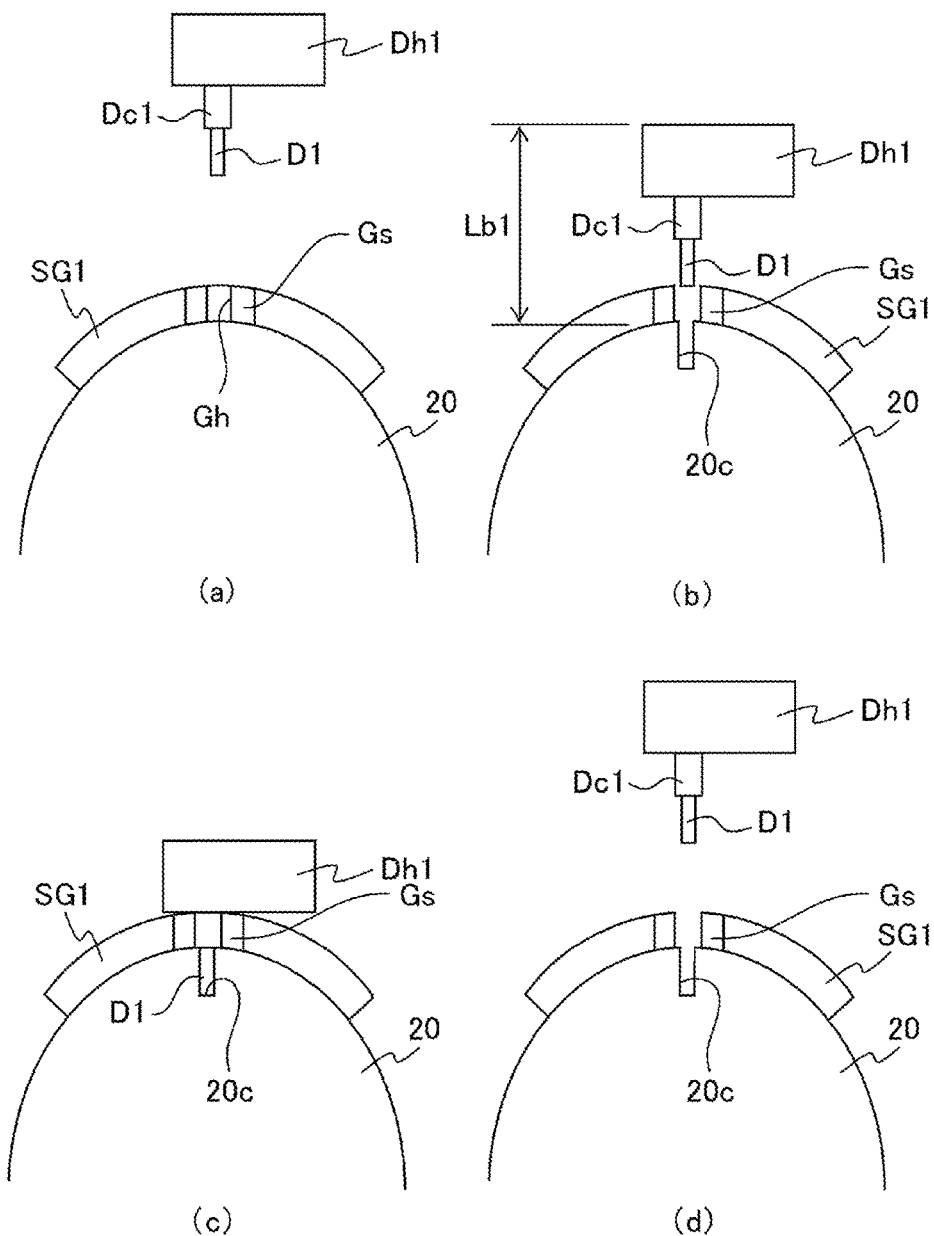

[Fig. 31]
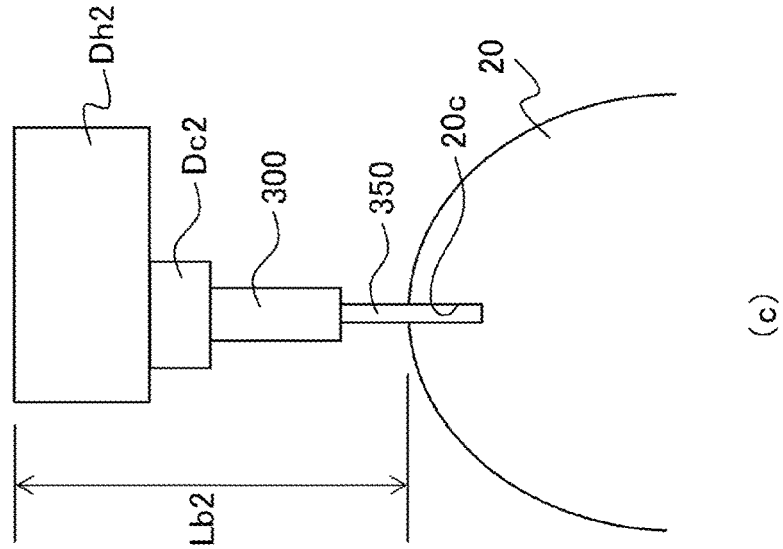
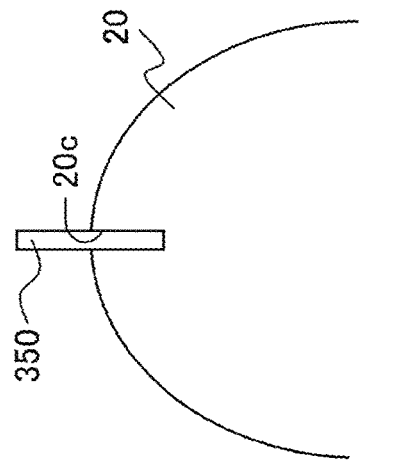
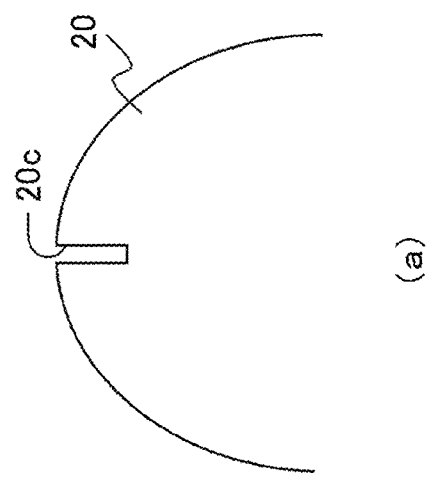

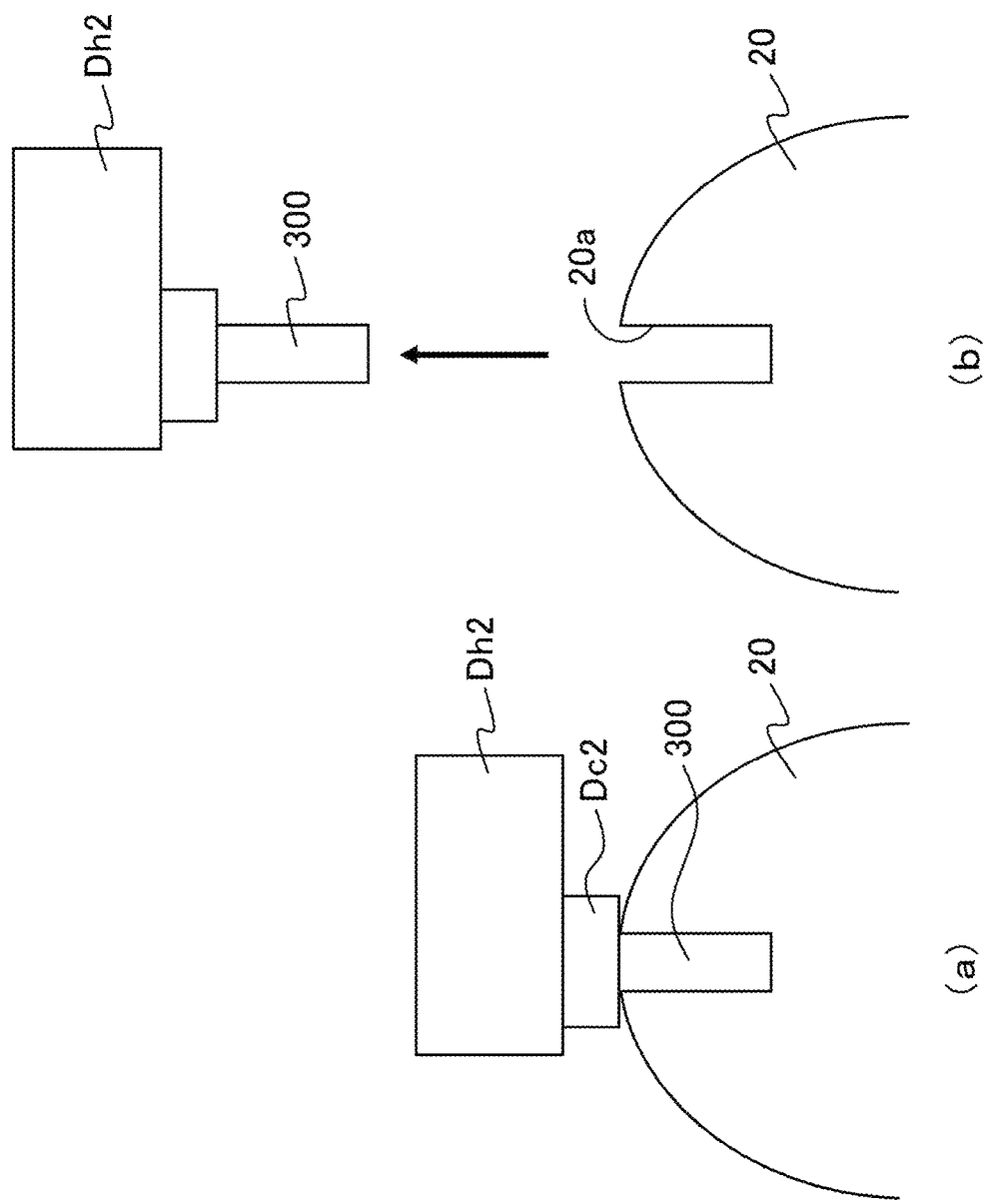
[Fig. 32]

[Fig. 33]
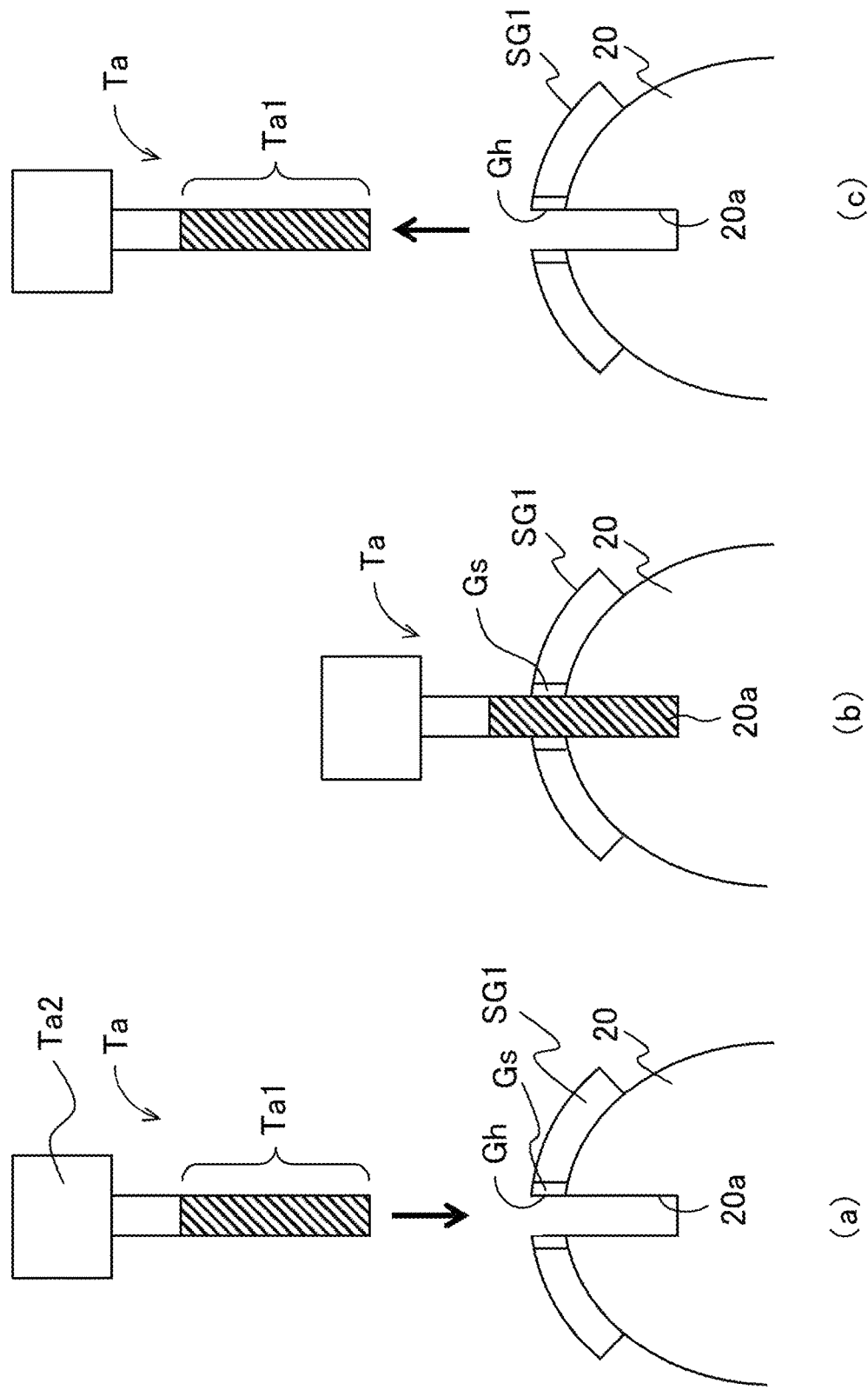

[Fig. 34]
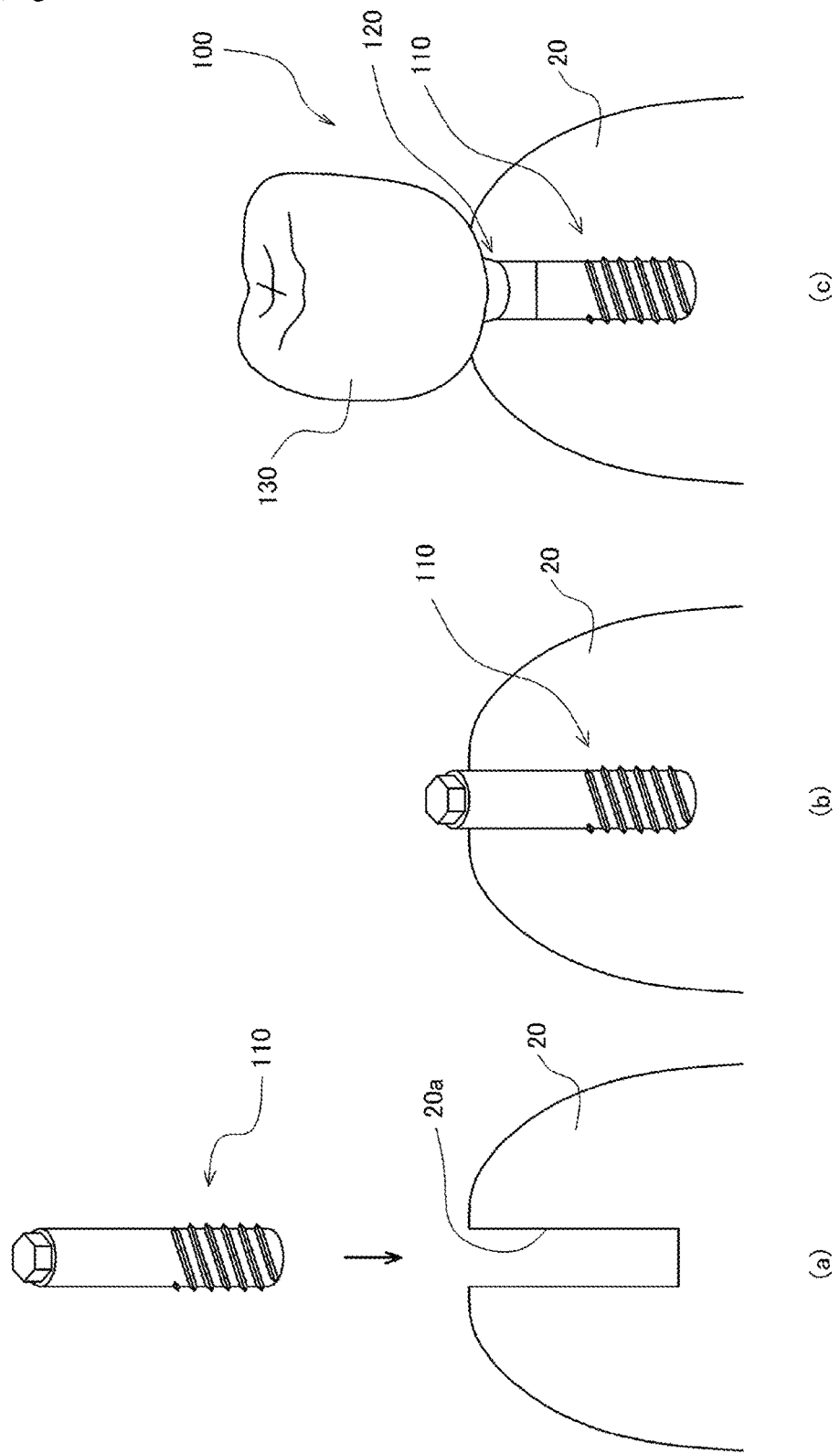

[Fig. 35]
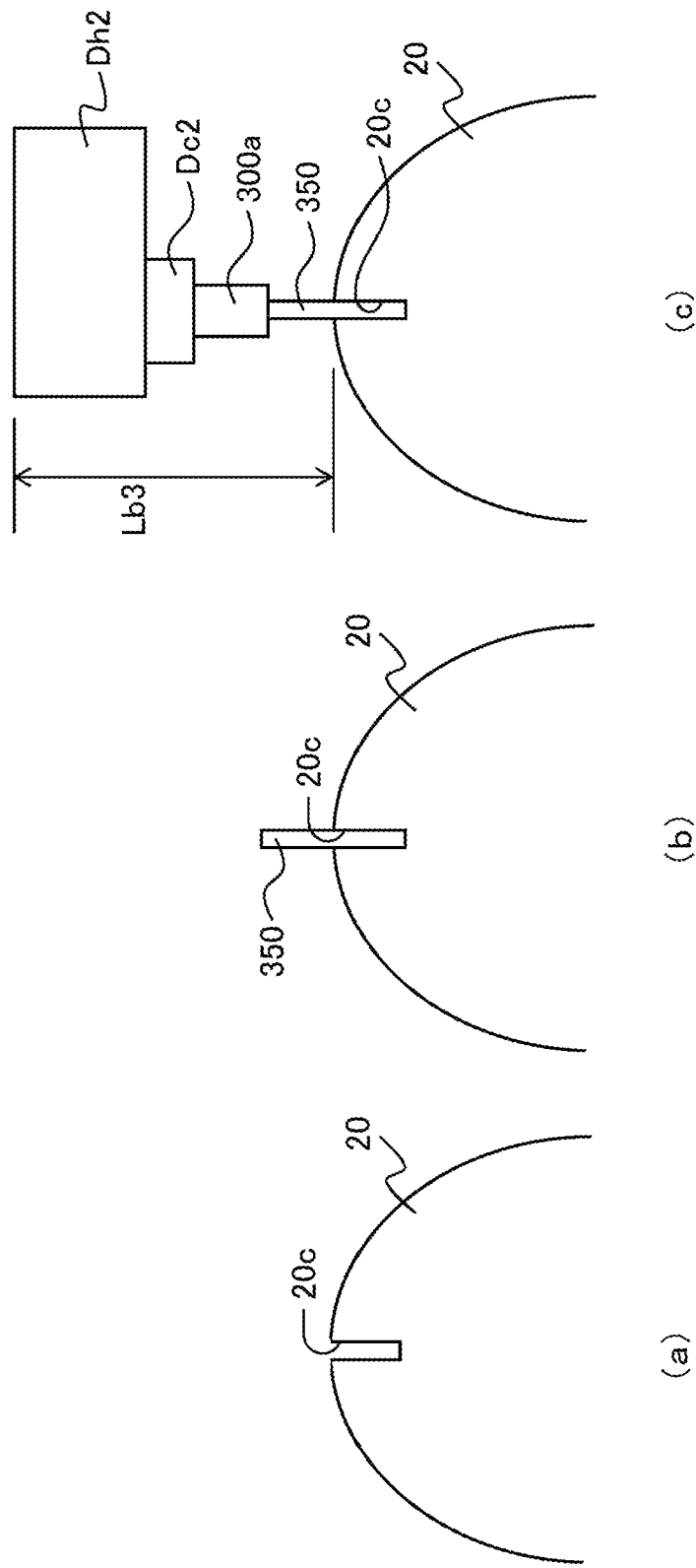

[Fig. 36]
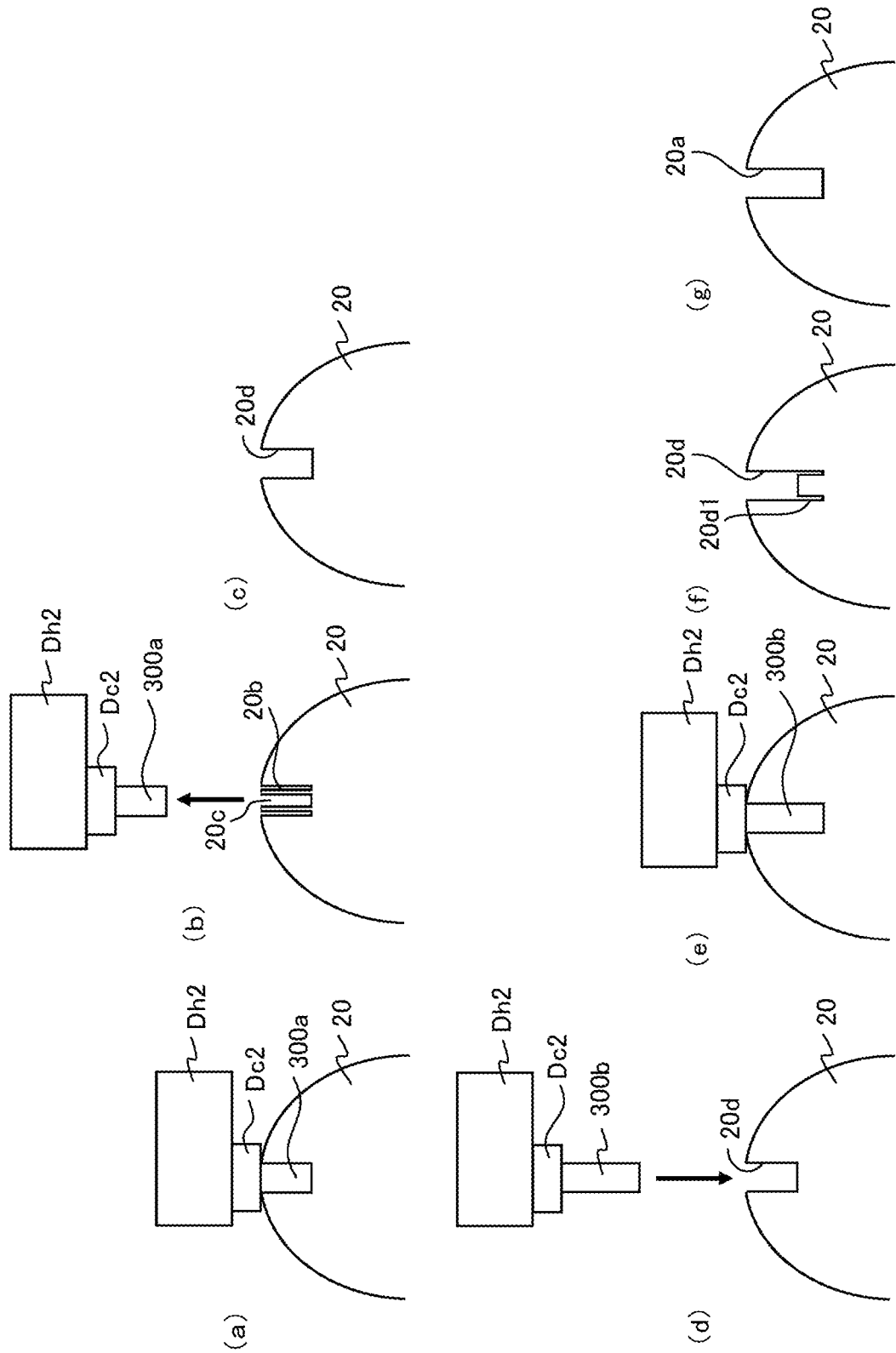

[Fig. 37]
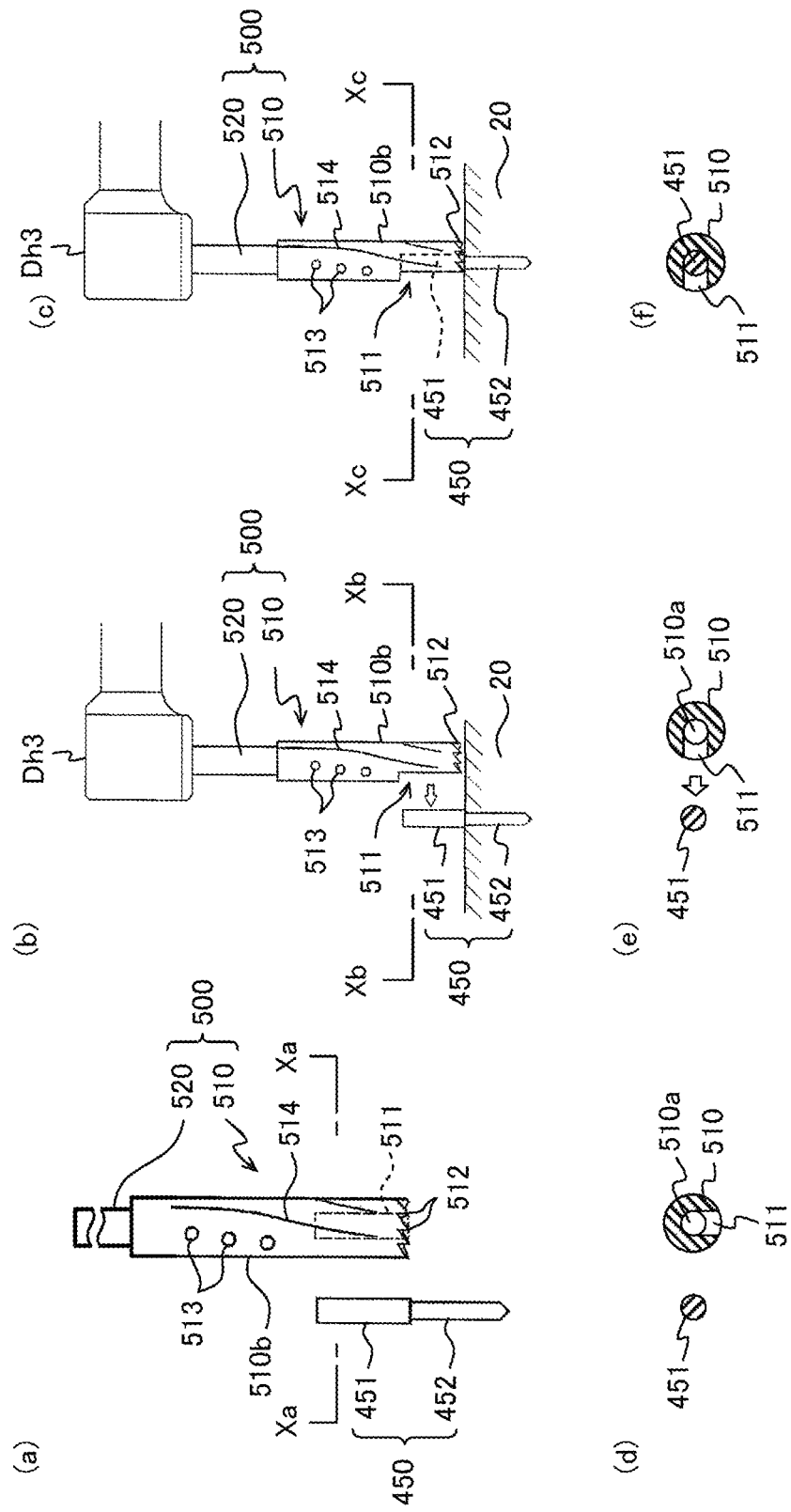

[Fig. 38]
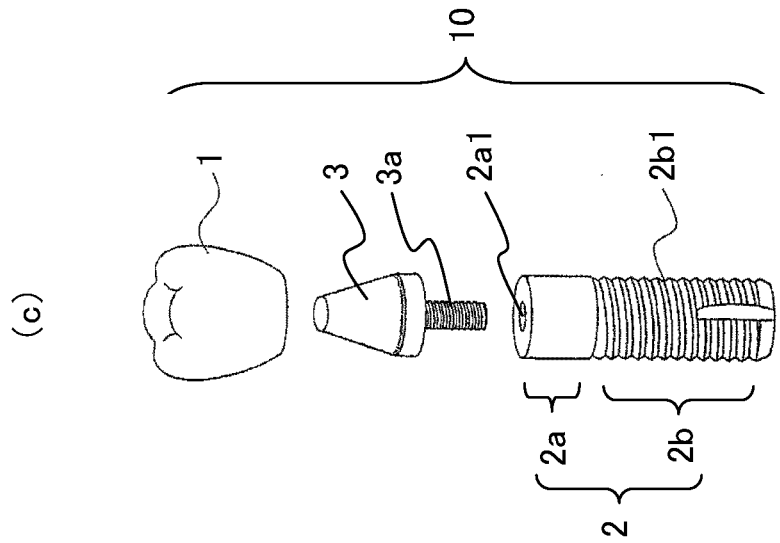
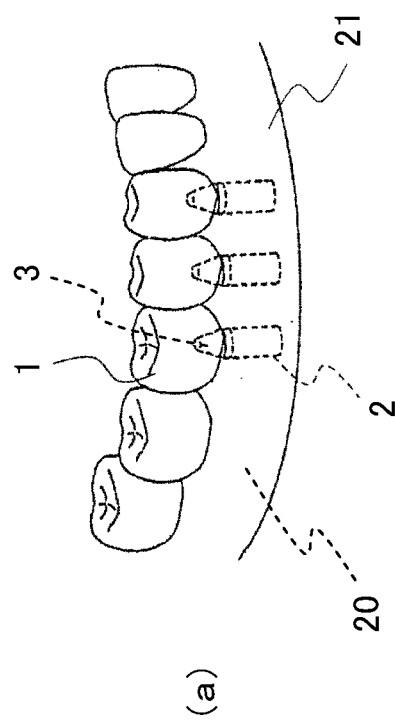
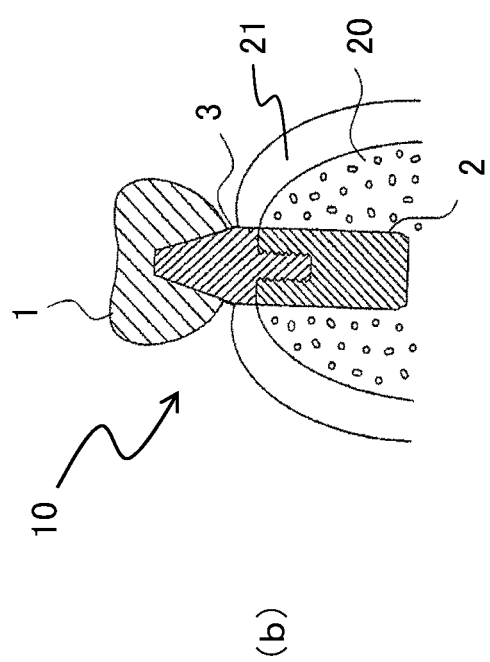

ABUTMENT, FIXTURE, DENTAL IMPLANT SET, DENTAL TAP, DENTAL GUIDE, DENTAL TAP SET AND DENTAL DRILL

CROSS-REFERENCE TO RELATED APPLICATIONS

This application is a U.S. national phase filing under 35 U.S.C. §371 of PCT/IB2013/058990 filed Sep. 30, 2013, which claims priority to and the benefit of JP Application No. 2012-233044 which was filed on Oct. 22, 2012, PCT Application No. PCT/JP2012/081268 which was filed on Dec. 3, 2012, JP Application No. 2013-038299 filed on Feb. 28, 2013 and JP Application No. 2013-170439 filed on Aug. 20, 2013. All of the aforementioned applications are incorporated herein by reference in their entirety.

TECHNICAL FIELD

The present invention relates to abutments, fixtures, dental implant sets, dental taps, dental guides, dental tap sets, and dental drills, and particularly relates to structures of a dental implant and dental equipment for enhancing workability and safety of an implant treatment and for alleviating strain on a patient at the time of an implant treatment.

BACKGROUND ART

Conventionally, there has been a treatment method for replacing a natural tooth that is lost from tooth decay, periodontal disease or the like with an artificial tooth. Such a treatment method is called an implant treatment, which is a method where an artificial root of a tooth is embedded in a jawbone and an artificial tooth is secured onto the artificial root of the tooth to restore the appearance and functions that are no different from those of the natural tooth.

FIG. 38 is a diagram for explaining a common dental implant that is used as an artificial teeth in such an implant treatment. FIGS. 38(a) and 38(b) are a perspective view and a cross-sectional view that illustrate an implanted state of a dental implant embedded in a jawbone. FIG. 38(c) is an exploded perspective view of a dental implant.

A dental implant 10 comprises, for example, a cylindrical implant body (hereinafter, referred to as a fixture) 2 that is implanted into a jawbone (alveolar bone) 20 as an artificial root of a tooth, a support mount (hereinafter, referred to as an abutment) 3 that is secured to the head of the fixture 2, and a top structure 1 that is mounted onto the abutment 3 as an artificial tooth with an adhesive or a screw. The top structure 1 is called a restoration or a prosthetic crown, and the top structure 1 will also be referred to as a restoration hereinafter.

Here, the fixture 2 and the abutment 3 are connected by a threaded engagement so that they can be detached for cleaning between the abutment 3 and gums 21 or for replacing the abutment. That is, a female screw section (screw hole) 2a1 for threadedly engaging a male screw section 3a, which is formed at the lower portion of the abutment 3, is formed on a head 2a of the fixture 2.

Patent Literature 1 discloses the structure of the common implant explained in FIG. 38.

CITATION LIST

Patent Literature

PTL 1: Japanese Laid-Open Publication No. 2007-98054

SUMMARY OF INVENTION

Technical Problem

In a conventional implant, an abutment is coupled to a fixture such that the abutment is detachable from the fixture for replacement or cleaning. However, a detaching operation of an abutment is not easy, as it is necessary to be performed in a narrow oral cavity. Thus, there is a risk of accidentally ingesting or swallowing an abutment that comes off. Further, detachment of an abutment is performed by loosening a screw that secures the abutment to a fixture by using a driver and a wrench while inserting the driver and the wrench into an oral cavity. Thus, an operation of detaching an abutment requires a patient to open his/her mouth wide during the operation, resulting in imposing great strain on the patient.

The present invention is for solving issues such as those described above and is intended to obtain an abutment and a fixture that enable an operation of detaching the abutment from the fixture to be readily performed without having a patient open his/her mouth wide while inhibiting accidental ingestion or swallowing of an abutment that comes off, and to obtain a dental implant set comprising such a fixture and an abutment.

Solution to Problem

An abutment for a dental implant according to the present invention, comprising a fitting recess for fitting onto a head of a fixture configured to couple with a jawbone, is provided, where the head of the fixture is secured to the fitting recess by a frictional force that is generated between an outside surface of the head of the fixture and an inside surface of the fitting recess when the head of the fixture fits into the fitting recess so that a space is formed between a top surface of the head of the fixture and a bottom surface of the fitting recess, and an instrument insertion hole for inserting, in the space, an instrument for disengaging the fitting recess secured to the head of the fixture by the frictional force, is formed on a sidewall of the fitting recess, thereby achieving an objective described above.

Preferably, in the abutment according to the present invention, the fitting recess has a structure in which at least a part of the inside surface of the fitting recess tightly contacts the outside surface of the head of the fixture so that an object that enters the fitting recess from the instrument insertion hole does not seep out toward the jawbone.

Still preferably, in an abutment according to the present invention, the fitting recess has a shape that matches a shape of the head of the fixture so that a rotation of the abutment with respect to the fixture is restricted when the head of the fixture fits into the fitting recess.

Still preferably, in an abutment according to the present invention, the inside surface of the fitting recess is tilted with respect to an insertion direction of the head of the fixture to the fitting recess to conform to the outside surface of the head of the fixture.

An abutment for a dental implant according to the present invention, comprising a plurality of fitting recesses for fitting onto a plurality of heads of fixtures configured to couple with a jawbone, is provided, where adjacent fitting recesses among the plurality of fitting recesses are linked to each other by a linking section, each of the plurality of heads of fixtures is secured to a corresponding fitting recess by a frictional force that is generated between an outside surface of each of the plurality of heads of fixtures and an inside surface of the corresponding fitting recess when each of the plurality of fitting recesses fits onto the head of a corresponding fixture so that a space is formed between a bottom surface of each of the plurality of fitting recesses and a top surface of the head of the corresponding fixture, and an instrument insertion hole for inserting an instrument for disengaging the fitting recess secured to the head of the fixture by the frictional force in the space, is formed on at least one sidewall of the plurality of fitting recesses, thereby achieving an objective described above.

Preferably, in an abutment according to the present invention, the fitting recess is configured such that a space is created between portions other than an edge section on an opening side of the inside surface of the fitting recess and the outside surface of the head of the fixture when the head of the fixture is inserted in the fitting recess.

A fixture for a dental implant according to the present invention, comprising an embedded section that is embedded in a jawbone; and a head for securing an abutment for supporting an artificial tooth, is provided, where the abutment has a fitting recess for fitting onto the head, and an instrument insertion hole for inserting an instrument is formed on a sidewall of the fitting recess, and the head is secured to the fitting recess of the abutment by a frictional force that is generated between an outside surface of the head and an inside surface of the fitting recess of the abutment when the head fits into the fitting recess of the abutment so that a space is formed between a top surface of the head and a bottom surface of the fitting recess of the abutment, thereby achieving an objective described above.

Preferably, in a fixture according to the present invention, the fixture consists of two components, which are a first component constituting the head and a second component constituting the embedded section; and the head and the embedded section are configured to be fastened by threadedly engaging a male screw section formed on the first component with a female screw section formed on the second component.

Still preferably, in a fixture according to the present invention, the head comprises an IC chip that stores data related to history of the dental implant.

A dental implant set according to the present invention comprising a fixture configured to couple with a jawbone and an abutment for supporting an artificial tooth is provided, where the fixture comprises an embedded section that is embedded in the jawbone and a head for securing the abutment, the abutment comprises a fitting recess for fitting onto the head of the fixture, the head of the fixture is secured to the fitting recess of the abutment by a frictional force that is generated between an outside surface of the head of the fixture and an inside surface of the fitting recess of the abutment when the head of the fixture fits into the fitting recess of the abutment so that a space is formed between a top surface of the head of the fixture and a bottom surface of the fitting recess of the abutment, and an instrument insertion hole for inserting an instrument for disengaging the fitting recess of the abutment secured to the head of the fixture by the frictional force in the space, is formed on a sidewall of the fitting recess of the abutment, thereby achieving an objective described above.

Preferably, in a dental implant set according to the present invention, the abutment is a standardized abutment that is attached to a head of an existing fixture embedded in the jawbone in place of an existing abutment; the fixture is a standardized fixture to which the standardized abutment is secured; the dental implant set further comprises a stent having a recess for fitting onto the standardized abutment and a securing pin for securing the stent to the standardized abutment; and the stent is configured such that a posture when the recess of the stent fits onto the standardized abutment attached to the existing fixture defines a direction of the standardized fixture replacing the existing fixture.

Still preferably, in a dental implant set according to the present invention, the securing pin is inserted through the fixture and the abutment secured to the head of the fixture.

A dental tap according to the present invention for forming a screw groove in an implant embedding hole for embedding a dental implant formed on a jawbone by using a dental drill and a guide member of the dental drill includes: a tap body that is screwed into the implant embedding hole so that the screw groove is formed in the implant embedding hole; and a tap holding section provided on one end of the tap body; where the guide member has a drill guide hole for guiding the dental drill and a screw groove is formed on an inside surface of the drill guide hole; and a screw thread for forming the screw groove in the implant embedding hole is formed on an outer circumferential surface of the tap body to threadedly engage the screw groove formed on the inside surface of the drill guide hole of the guide member, thereby achieving an objective described above.

Preferably, in a dental tap according to the present invention, a cutting section for cutting out a cortical bone constituting the jawbone is formed on the other end of the tap body.

A dental guide according to the present invention, used as a guide member of a dental drill when forming an implant embedding hole for embedding a dental implant with the dental drill and as a guide member of a dental tap when forming a screw groove in the implant embedding hole with the dental tap, comprising a guide hole for guiding the dental drill and the dental tap, is provided, where a screw groove is formed to threadedly engage the screw thread for forming a screw groove in the implant embedding hole, where the screw thread is formed on an outer circumferential surface of the dental tap, thereby achieving an objective described above.

A dental tap set according to the present invention for forming a screw groove in an implant embedding hole for embedding a dental implant, formed on a jawbone, the dental tap set comprising a dental tap and a dental guide, is provided, where the dental tap comprises a tap body that is screwed into the implant embedding hole so that the screw groove is formed in the implant embedding hole and a tap holding section provided on one end of the tap body, and a screw thread for forming the screw groove in the implant embedding hole is formed on an outer circumferential surface of the tap body; the dental guide is used as a guide member of a dental drill when forming the implant embedding hole with the dental drill and as a guide member of the dental tap when forming a screw groove in the implant embedding hole with the dental tap, the dental guide having a guide hole for guiding the dental drill and the dental tap, and the screw groove is formed on an inside surface of the guide hole to threadedly engage the screw thread formed on the outer circumferential surface of the tap body, thereby achieving an objective described above.

Preferably, in a dental tap set according to the present invention, the dental tap set comprises a plurality of dental taps; height of the screw thread formed on the tap body differs for each of the plurality of dental taps; and only some of the plurality of dental taps have a cutting section for cutting out a cortical bone constituting the jawbone, where the cutting section is formed on the other end of the tap body.

A dental drill according to the present invention for forming an implant embedding hole for embedding a dental implant on a jawbone, comprising a drill body for drilling the jawbone; and a drill support for supporting the drill body, is provided, where the drill body has a throughhole for inserting a rod-shaped guide, and the drill body is configured to be rotatable and to be movable along the rod-shaped guide while having the rod-shaped guide inserted in the throughhole, and the implant embedding hole is formed by drilling the jawbone by rotating the drill body and entering the drill body into the jawbone, thereby achieving an objective described above.

Preferably, in a dental drill according to the present invention, the drill body has an incision formed at a bottom end of a sidewall so that the rod-shaped guide secured to the jawbone passes through the sidewall of the drill body.

Still preferably, in a dental drill according to the present invention, the jawbone comprises a regenerated section in which a bone of another person is embedded; the implant embedding hole is formed in the regenerated section by drilling the regenerated section with the drill body while the rod-shaped guide secured to the regenerated section is inserted in the throughhole of the drill body.

Still preferably, in a dental drill according to the present invention, a helical groove is formed on an outer circumferential surface of the drill body, and drilling scrap that is generated by drilling the jawbone when forming the implant embedding hole is discharged from the helical groove.

Still preferably, in a dental drill according to the present invention, the drill body is a cylindrical body, and a drilling blade is formed along a circumferential edge on one end of the cylindrical body.

Advantageous Effects of Invention

According to the present invention, it is possible to materialize an abutment and a fixture that enable an operation of detaching the abutment from the fixture to be readily performed without having a patient open his/her mouth wide while inhibiting accidental ingestion or swallowing of an abutment that comes off from occurring, and a dental implant set comprising such a fixture and an abutment.

According to the present invention, it is possible to materialize a dental tap and a dental guide that enable a fixture to be screwed into a jawbone with non-uniform hardness without misalignment, and a dental tap set comprising such a dental tap and a dental guide.

According to the present invention, it is possible to materialize a dental drill that is capable of forming an implant embedding hole for embedding a fixture in an appropriate position and direction as well as eliminating the need to have a patient open his/her mouth wide in forming the implant embedding hole.

Thus, the present invention is capable of materializing an implant treatment that enables enhancement in workability and safety as well as alleviation in strain imposed on a patient during establishment or maintenance of a dental implant. Therefore, the present invention is an essential technique for the popularization of dental implants.

BRIEF DESCRIPTION OF DRAWINGS

FIG. 1 is a diagram for explaining a dental implant according to Embodiment 1 of the present invention. FIG. 1 illustrates a mounted state of a dental implant on a jawbone (FIG. 1(a)) and a disassembled state of the dental implant into a fixture, an abutment, and a restoration (FIG. 1(b)).

FIG. 2 is a diagram for explaining a dental implant according to Embodiment 1 of the present invention. FIG. 2 compares and illustrates cross-sectional structures of the essential parts of the dental implant in a state where a fixture and an abutment are separated (FIG. 2(a)) and in a state where the fixture and the abutment are coupled (FIG. 2(b)).

FIG. 3 is a diagram for explaining a dental implant according to Embodiment 1 of the present invention. FIG. 3 is a diagram for explaining a remover device used in procedures such as maintenance of such a dental implant.

FIG. 4 is a diagram (perspective view) for explaining the dental implant according to Embodiment 1 of the present invention. FIG. 4 is an expanded view that illustrates the essential parts of the remover illustrated in FIG. 3.

FIG. 5 is a diagram (perspective view) for explaining a dental implant according to Embodiment 1 of the present invention. FIG. 5 schematically illustrates the states prior to and after operating a remover device, seen from the front of an instrument insertion hole of an abutment (FIGS. 5(a) and 5(b)).

FIG. 6 is a diagram (perspective view) for explaining a dental implant according to Embodiment 1 of the present invention. FIG. 6 schematically illustrates the states prior to and after operating a remover device, seen from the left side surface of an instrument insertion hole of an abutment (FIGS. 6(a) and 6(b)).

FIG. 7 is a diagram for explaining a dental implant according to variants of Embodiment 1 of the present invention. FIG. 7 illustrates an abutment for a dental implant according to Variant 1 (FIG. 7(a)) and an abutment for a dental implant according to Variant 2 (FIG. 7(b)).

FIG. 8 is a diagram (perspective view) for explaining a dental implant according to Variant 3 of Embodiment 1 of the present invention. FIG. 8 schematically illustrates the states prior to and after operating a remover device, seen from the front of an instrument insertion hole of an abutment (FIGS. 8(a) and 8(b)).

FIG. 9 is a diagram (perspective view) for explaining a dental implant according to Variant 3 of Embodiment 1 of the present invention. FIG. 9 schematically illustrates the states prior to and after operating a remover device, seen from the left side surface of an instrument insertion hole of an abutment (FIGS. 9(a) and 9(b)).

FIG. 10 is a diagram for explaining a dental implant according to Variant 4 of Embodiment 1 of the present application. FIG. 10 illustrates a state where gums are formed on a surface of a fixture (FIG. 10(a)) and the structure of essential parts of such a dental implant (FIG. 10(b)).

FIG. 11 is a diagram for explaining a dental implant according to Variant 5 of Embodiment 1 of the present invention.

FIG. 12 is a diagram for explaining a dental implant according to Variant 6 of Embodiment 1 of the present invention. FIG. 12 illustrates the overall structure of an abutment for such a dental implant.

FIG. 13 is a diagram for explaining a dental implant according to Variant 6 of Embodiment 1 of the present invention. FIG. 13 is a cross-sectional view (FIG. 13(a)) illustrating a fitted state of an abutment and an implant for such a dental implant, and an expanded view thereof (FIG. 13(b)).

FIG. 14 is a diagram for explaining a dental implant set according to Embodiment 2 of the present invention. FIG. 14 illustrates an attached state of a dental implant to a jawbone (FIG. 14(a)) and a fixture, abutment, stent and securing pin for repositioning the dental implant (FIG. 14(b)).

FIG. 15 is a diagram for explaining a dental implant set according to Embodiment 2. FIG. 15 is a perspective view (FIG. 15(a)) and a cross-sectional view (FIG. 15(b)) of a stent comprised in such a dental implant.

FIG. 16 is a diagram for explaining a dental implant set according to Embodiment 2 of the present invention. FIG. 16 illustrates a method of repositioning by using such a dental implant set in the order of steps (FIGS. 16(a)-16(g)).

FIG. 17 is a diagram for explaining a dental implant set according to Embodiment 2 of the present invention. FIG. 17 illustrates a method of repositioning by using such a dental implant set in the order of steps (FIGS. 17(a)-17(e)).

FIG. 18 is a side view (FIG. 18(a)) and a cross sectional view (FIG. 18(b)) for explaining a dental tap according to Embodiment 3 of the present invention.

FIG. 19 is a diagram for explaining a dental guide according to Embodiment 3 of the present invention. FIG. 19 illustrates the overall structure of the dental guide (FIG. 19(a)) and a guide sleeve attached to the dental guide (FIG. 19(b)).

FIG. 20 is a diagram for explaining a dental guide according to Embodiment 3 of the present invention. FIG. 20 is a side view (FIG. 20(a)) and a cross-sectional view (FIG. 20(b)) of a guide sleeve of the dental guide.

FIG. 21 is a diagram for explaining a method of using a dental tap set according to Embodiment 3 of the present invention. FIG. 21 illustrates the formation of an implant embedding hole and tapping (FIGS. 21(a)-21(f)) in the order of steps.

FIG. 22 is a diagram for explaining a method of using a dental tap set according to Embodiment 3 of the present invention. FIG. 22 illustrates a method of forming an implant embedding hole (tap pilot hole) (FIGS. 22(a)-22(c)) in the order of major steps.

FIG. 23 is a diagram for explaining a method of using a dental tap set according to Embodiment 3 of the present invention. FIG. 23 illustrates a method of forming a screw groove in an implant embedding hole (tap pilot hole) (FIGS. 23(a)-23(d)) in the order of major steps.

FIG. 24 is a diagram for explaining a dental guide according to the Variant of Embodiment 3 of the present invention. FIG. 24 is a side view (FIG. 24(a)) and a cross-sectional view (FIG. 24(b)) of a guide sleeve of a dental guide.

FIG. 25 is a diagram for explaining a method of using a dental tap set according to the Variant of Embodiment 3. FIG. 25 illustrates the formation of an implant embedding hole and tapping (FIGS. 25(a)-25(f)) in the order of steps.

FIG. 26 is a diagram for comparing a common socket lift procedure with a method of using a dental tap set according to the Variant of Embodiment 3 of the present invention. FIG. 26 illustrates the formation of an implant embedding hole and tapping (FIGS. 26(a)-26(f)) in the order of major steps.

FIG. 27 illustrates other structural examples of a dental tap used in a dental tap set according to the Variant of Embodiment 3 of the present invention (FIGS. 27(a)-27(d)).

FIG. 28 is a diagram for explaining a dental drill according to Embodiment 4 of the present invention. FIG. 28 illustrates such a dental drill and a rod-shaped guide for guiding the dental drill (FIG. 28(a)) and states of use of the dental drill and the rod-shaped guide (FIGS. 28(b)-28(d)).

FIG. 29 is a diagram for illustrating a guide member (surgical guide) for use in positioning a rod-shaped guide of a dental drill according to Embodiment 4 of the present invention. FIG. 29 illustrates the overall structure of the guide member (FIG. 29(a)) and a guide sleeve that is attached to the guide member (FIG. 29(b)).

FIG. 30 is a diagram for explaining a method of forming an implant embedding hole by using a dental drill according to Embodiment 4 of the present invention. FIG. 30 illustrates processing at major steps of such a method (FIGS. 30(a)-30(d)).

FIG. 31 is a diagram for explaining a method of forming an implant embedding hole by using a dental drill according to Embodiment 4 of the present invention. FIG. 31 illustrates processing at major steps of such a method (FIGS. 31(a)-31(c)).

FIG. 32 is a diagram for explaining a method of forming an implant embedding hole by using a dental drill according to Embodiment 4 of the present invention. FIG. 32 illustrates processing at major steps of such a method (FIGS. 32(a)-32(b)).

FIG. 33 is a diagram for explaining a method of forming a screw groove in an implant embedding hole formed by using a dental drill according to Embodiment 4 of the present invention. FIG. 33 illustrates processing at major steps of such a method (FIGS. 33(a)-33(c)).

FIG. 34 is a diagram for explaining a method of installing a dental implant in an implant embedding hole formed by using a dental drill according to Embodiment 4 of the present invention. FIG. 34 illustrates processing at major steps of such a method (FIGS. 34(a)-34(c)).

FIG. 35 is a diagram for explaining a method of forming an implant embedding hole by using a dental drill according to Variant 1 of Embodiment 4 of the present invention. FIG. 35 illustrates processing at major steps of such a method (FIGS. 35(a)-35(c)).

FIG. 36 is a diagram for explaining a method of forming an implant embedding hole by using a dental drill according to Variant 1 of Embodiment 4 of the present invention. FIG. 36 illustrates processing at major steps of such a method (FIGS. 36(a)-36(g)).

FIG. 37 is a diagram for explaining a dental drill according to Variant 2 of Embodiment 4 of the present invention. FIG. 37 illustrates such a dental drill and a rod-shaped guide thereof (FIG. 37(a)), a cross-section at the Xa-Xa line of FIG. 37(a) (FIG. 37(d)), a method of engaging the dental drill with the rod-shaped guide (FIGS. 37(b) and 37(c)), a cross-section at the Xb-Xb line of FIG. 37(b) (FIG. 37(e)), and a cross-section at the Xc-Xc line of FIG. 37(c) (FIG. 37(f)).

FIG. 38 is a diagram for explaining a conventional, common dental implant. FIGS. 38(a) and 38(b) are a perspective view and a cross-sectional view that illustrate an implanted state of a dental implant in a jawbone. FIG. 38(c) is an exploded perspective view of the dental implant.

DESCRIPTION OF EMBODIMENTS

Hereinafter, the Embodiments of the present invention will be disclosed while referring to the drawings.

Embodiment 1

(Dental Implants)

FIG. 1 is a diagram for explaining a dental implant according to Embodiment 1 of the present invention. FIG. 1 illustrates a mounted state of a dental implant on a jawbone (FIG. 1(a)) and a disassembled state of the dental implant into a fixture, an abutment, and a restoration (FIG. 1(b)). FIG. 2 is a diagram for illustrating the essential parts of the fixture and the abutment constituting the dental implant of Embodiment 1. FIG. 2(a) illustrates a separated state of the fixture and the abutment and FIG. 2(b) illustrates a coupled state of the fixture and the abutment.

A dental implant 100 of Embodiment 1 comprises a fixture 110 that is embedded into a jawbone (alveolar bone) 20 and is configured to couple with the jawbone 20, an abutment 120 that is configured to be secured to the fixture 110, and an artificial tooth 130 that is configured to be attached to the abutment 120 as a top structure. Such an artificial tooth is called a restoration or a prosthetic crown and is also referred to as a restoration hereinafter.

At least the fixture and the abutment among the fixture 110, the abutment 120, and the restoration 130 that constitute such a dental implant 100 are generally supplied by a manufacturer of dental implants as a dental implant set. Further, such a dental implant set may comprise a tool or the like for use in an implant treatment.

Here, the fixture 110 and the abutment 120 are both constituted of a metallic material, such as pure titanium or a titanium alloy with excellent biocompatibility, histocompatibility and mechanical biocompatibility. Since titanium is a material with high bioaffinity, this is especially for the jawbone 20 to be securely coupled to the fixture 110 without having the fixture 110 recognized as a foreign substance by a human body. Further, the fixture 110 comprises an embedded section (hereinafter, also referred to as a fixture embedded section) 111 that is embedded in the jawbone 20 and a head (hereinafter, also referred to as a fixture head) 112 for securing the abutment 120. Threads 111a are formed on the outer circumferential surface of the embedded section 111 of the fixture 110 so that the fixture 110 is less likely to slip out from the jawbone 20. Furthermore, the fixture head 112 has a truncated conical section (hereinafter, also referred to as an outer tapered section) 112a and a hexagonal prism section 112b that is formed on the truncated conical section 112a. Further, the diameter of the abutment is 2.5 mm-4.0 mm and is preferably 3.0 mm in particular.

Further, the abutment 120 has a fitting recess 121 that fits onto the fixture head 112. Such a fitting recess 121 is formed by forming a longitudinal hole 123 on the lower portion of the abutment 120. The fitting recess 121 comprises: a circular groove section (hereinafter, referred to as an inner tapered section) 121a for receiving the outer tapered section 112a of the fixture 110; and a hexagonal groove section 121b formed at the bottom surface of the hexagonal groove section 121a, for receiving the hexagonal prism section 112b of the fixture head 112. The hexagonal groove section 121b is configured to fit onto the hexagonal prism section 112b of the fixture head 112 when the fixture head 112 is inserted into the fitting recess 121 of the abutment 120.

In the abutment 120, when the fixture head 112 is fitted into the fitting recess 121 of the abutment 120 so as to form a space S between a top surface 112b1 of the fixture head 112 (i.e., top surface of the hexagonal prism section) and a bottom surface 121d of the fitting recess 121 of the abutment 120, the fixture head 112 is secured to the fitting recess 121 of the abutment 120 by a frictional force generated between an outer circumferential surface 114 of the outer tapered section 112a of the fixture 110 and an inner circumferential surface 125 of the inner tapered section 121a of the fitting recess 121 of the abutment 120. An instrument insertion hole 129 (transverse hole) for inserting an instrument (remover) 80c (see FIG. 3) into the space S is formed on a sidewall 121c of the fitting recess 121 of the abutment 120, where the instrument (remover) 80c disengages the fitting recess 121 of the abutment 120 secured to the head 112 of the fixture 110 by a frictional force. The position for forming such an instrument insertion hole 129 is not limited to a specific position on the surface of the fitting recess 121 of the abutment 120. The instrument insertion hole 129 may be formed either on an inside surface facing in towards an oral cavity of the surface of the fitting recess 121 or on an outside surface facing out of the oral cavity. Furthermore, the instrument insertion hole 129 may be formed on a surface position on the fitting recess 121 that matches the position of the abutment within the oral cavity. Further, the restoration 130 has an instrument insertion hole 139 that corresponds to the instrument insertion hole 129 of the abutment 120. The instrument insertion hole 139 of the restoration 130 is formed so as to overlap the instrument insertion hole 129 of the abutment 120 when the restoration 130 is mounted on the abutment 120.

Further, the fitting recess 121 of the abutment 120 is configured so that the entire surface of the inner circumferential surface 125 of the inner tapered section 121a is tightly in contact with the outer circumferential surface 114 of the outer tapered section 112a of the fixture 110. For this reason, the space between the fitting recess 121 and the fixture head 112 is sealed. Thus, objects that enter the fitting recess 121 or bacteria that propagates would not seep through between the fitting recess 121 and the fixture head 112 to the gums.

Specifically, a taper angle between the outer tapered section 112a of the fixture 110 and the inner tapered section 121a of the abutment 120 (i.e., an angle formed by the outer circumferential surface 114 of the outer tapered section 112a and the inner circumferential surface 125 of the inner tapered section 121a with respect to the axis of the fixture) can be, for example, 0-10 degrees, and more preferably 1.0-3.0 degrees. Furthermore, the angle is set at 1.5 degrees in the present Embodiment to secure a strong retentive force by a taper connection.

Further, the surface roughness of the outer circumferential surface 114 of the outer tapered section 112a and that of the inner circumferential surface 125 of the inner tapered section 121a can be set to have an arithmetic mean roughness Ra of, for example, 1.6 μm or less (about 0.26 μm in the Embodiment 1), thereby a strong retentive force is reliably obtained.

Furthermore, the shape of the fitting recess 121 is configured to have a shape that matches the shape of the top surface 112b1 of the fixture head 112 so as to restrict the rotation of the abutment 120 with respect to the fixture 110 when the head 112 of the fixture 110 is fitted into the fitting recess 121 of the abutment 120.

Specifically, in Embodiment 1, as stated above, the fixture head 112 has the hexagonal prism section 112b formed on the truncated conical section (outer tapered section) 112a. In addition, the fitting recess 121 of the abutment 120 has the hexagonal groove section 121b formed on the bottom surface of the circular groove section 121a (inner tapered section) so as to fit onto the hexagonal prism section 112b of the fixture head 112 when the fixture head 112 is inserted into the fitting recess 121 of the abutment 120. Thus, in a state where the fixture head 112 is secured to the fitting recess 121 of the abutment 120, the hexagonal prism section 112b of the fixture head 112 fits into the hexagonal groove section 121b of the fitting recess 121 of the abutment 120 to restrict the rotation of the abutment 120 with respect to the fixture 110.

(Remover Device)

FIGS. 3 and 4 are diagrams for explaining a remover device used in procedures such as maintenance of the dental implant of Embodiment 1. FIG. 3 illustrates the overall structure of such a remover device. FIG. 4 illustrates the essential parts of such a remover device.

A remover device 80 comprises a body 80a, an arm section 80b that is attached to the body 80a, and a fit disengaging rod (remover) 80c that is attached to the tip of the arm section 80b. The fit disengaging rod 80c is configured to rotate by a driving force that is generated electrically or manually at the device body 80a.

Further, the cross-sectional shape of the fit disengaging rod 80c, which is vertical to the rotational axis, has an oval shape. Thus, in a state where the space S between the top surface 112b1 of the fixture head and the bottom surface 121d of the hexagonal groove section 121b in the fitting recess 121 of the abutment 120 is formed, when the fitting recess 121 of the abutment 120 is fitted onto the fixture head 112, the fit disengaging rod 80c is inserted into the space S while in a rotational position where the width in the height direction is narrower than the space S. Then, since the surface of the fit disengaging rod 80c is in contact with the top surface 112b1 of the fixture head 112 and the bottom surface 121d of the hexagonal groove section 121b in the fitting recess 121 of the abutment 120 by a rotation of the fit disengaging rod 80c, the space S between the top surface 112b1 of the fixture head 112 and the bottom surface 121d of the hexagonal groove section 121b in the fitting recess 121 of the abutment 120 is widened to the maximum diameter of the fit disengaging rod 80c, and thereby the fitting recess 121 secured to the fixture head 112 by a frictional force is disengaged.

(Embedding and Mounting Method of an Implant)

Next, a method of embedding such a dental implant of Embodiment 1 will be briefly explained by using FIG. 1(a).

First, an implant embedding hole for embedding the dental implant 100 in the jawbone 20 is formed, and the fixture 110 of the dental implant 100 is embedded into the implant embedding hole. After verifying that the jawbone 20 is coupled to the fixture 110, the abutment 120 is then mounted onto the fixture 110.

Specifically, as illustrated in FIG. 2(a), the longitudinal hole 123 extending from the bottom surface toward the inside is formed in the abutment 120 to form the fitting recess 121. Thus, attachment of the abutment 120 to the fixture 110 is performed by inserting the fixture head 112 into the fitting recess 121 of the abutment 120. That is, the outer tapered section 112a of the fixture head fits into the inner tapered section 121a of the fitting recess 121 of the abutment 120. The fixture 110 and the abutment 120 are thereby in a state of a strong bond by a metal-on-metal friction. Thus, a state is created where it is very difficult or impossible to pull out the abutment 120 fitted onto the fixture 110 with a bare hand from the fixture 110.

This is because the inner tapered section 121a that constitutes the fitting recess 121 of the abutment 120 is configured to slightly widen in diameter towards the bottom surface side of the abutment 120, and the outer tapered section 112a of the fixture head 112 is secured by a taper connection (Morse taper connection), i.e., friction, to the inner tapered section 121a, so as not to create any space between the outer tapered section 112a of the fixture head 112 and the inner tapered section 121a of the fitting recess 121 of the abutment 120.

After securing the abutment 120 to the fixture 110 as such, the restoration 130 as an artificial tooth is mounted onto the abutment 120 with an adhesive or the like. At this time, the restoration 130 is positioned so that the instrument insertion hole 139 thereof overlaps the instrument insertion hole 129 of the abutment 120. Attachment of a dental implant by an implant treatment is thereby completed.

Next, a method of detaching the abutment 120 secured to the fixture 110 by using the remover device 80 will be explained by using FIGS. 3-6.

In FIGS. 3-6, the top structure (restoration) 130 mounted onto the abutment 120 is not illustrated in order to show disengagement of fit between the fixture 110 and the abutment 120 in an easy-to-understand manner. However, in an actual implant treatment, detachment of the abutment 120 secured to the fixture 110 is performed in the state where the restoration 130 is mounted onto the abutment 120, as illustrated in FIG. 1(a). That is, the remover 80c for disengaging the fit between the fixture 110 and the abutment 120 sequentially passes through the instrument insertion hole 139 of the restoration 130 and the instrument insertion hole 129 of the abutment 120 from outside of the restoration 130 to reach the space S between the top surface 112b1 of the fixture head 112 and the bottom surface 121d of the fitting recess 121 of the abutment 120.

FIGS. 5 and 6 are diagrams (perspective view) for explaining the dental implant according to Embodiment 1 of the present invention. FIG. 5 schematically illustrates the states prior to and after operating a remover device, seen from the front of the instrument insertion hole of the abutment (FIGS. 5(a) and 5(b)). FIG. 6 schematically illustrates the states prior to and after operating the remover device, seen from the left side surface of the instrument insertion hole of the abutment (FIGS. 6(a) and 6(b)).

As illustrated in FIG. 2, the instrument insertion hole (transverse hole) 129 is formed on a sidewall of the fitting recess 121 of the abutment 120 such that the instrument insertion hole 129 connects to the longitudinal hole 123 that constitutes the fitting recess 121. As illustrated in FIG. 6(a), the top surface 112b1 of the head 112 of the fixture 110 in a fitted state is at a position, which is spaced downward from the top end of the transverse hole 129 (FIG. 2(b)).

Meanwhile, the remover device 80 has a substantially rod-shaped fit disengaging rod (remover) 80c having a longitudinal section with a substantially oval shape, as illustrated in FIGS. 3, 4, and 5(a). In addition, when the remover 80c is inserted into the transverse hole 129 in the orientation where the thickness in the top-to-bottom direction of the remover 80c is minimized (state where the major axis of an oval is laid down sideways) (see FIG. 5(a)), the remover 80c can reach the area above the top surface 112b1 of the head 112 of the fixture 110 in a fitted state (see FIGS. 3, 4, and 6(a)).

In other words, even if the remover 80c is inserted into the transverse hole 129 in the orientation where the thickness in the top-to-bottom direction of the remover 80c is maximized (state where the major axis of the oval is stood up longitudinally, or the state where the remover 80c having the orientation as shown in FIG. 5(a) is rotated 90 degrees around the axial center), the remover 80c would collide with a side surface 112b2 of the head 112 of the fixture 110 in a fitted state. Thus, the remover 80c cannot reach the area above the top surface 112b1 of the head 112 of the fixture 110.

In order to separate the abutment 120 in a fitted state from the fixture 110 by using such a remover 80c, first, the remover 80c is oriented to minimize the thickness in the top-to-bottom direction thereof and is inserted in the transverse hole 129 to reach the area above the top surface 112b1 of the head 112 of the fixture 110, as illustrated in FIGS. 5(a) and 6(a). In addition, if the remover 80c of the remover device 80 is rotated around the axial center in this state as illustrated in FIGS. 5(b) and 6(b), the remover 80c would be in a state where the outer surface (bottom surface) of the tip section of the remover 80c touches the top surface 112b1 of the head 112 of the fixture 110 and the outer surface (top surface) of the remover 80c touches the top edge section of the transverse hole 129 before the orientation of the remover 80c becomes the orientation where the thickness of the remover 80c in the top-to-bottom direction is maximized.

If the remover 80c is further rotated in this state, the abutment 120 is lifted up by the remover 80c and is separated from the fixture 110.

In this manner, removal operation of the abutment 120 that is secured to the fixture 110 can be performed simply by rotating the remover 80c that is inserted into the instrument insertion hole 139 (transverse hole) of the restoration 130 and the instrument insertion hole 129 (transverse hole) of the abutment 120 in Embodiment 1. The operation is very simply and it is not necessary to force a patient to open his/her mouth wide. Further, barely any repercussion is generated when detaching the abutment 120 from the fixture 110. Thus, accidental ingestion or the like of the restoration 130 or abutment 120 is unlikely to occur.

Furthermore, in the present Embodiment, the abutment 120 is configured such that the top surface 112b1 of the fixture head 112 is positioned between the top edge and the bottom edge of the transverse hole 129 when the head 112 of the fixture 110 is fitted into with the fitting recess 121 of the abutment 120. Thus, when the abutment 120 is mounted onto the fixture 110, it is possible to determine the quality of the mounting state of the abutment 120 to a certain degree from whether the head 112 of the fixture 110 can be seen from the transverse hole 129.

The present invention is not limited to the above-described Embodiment. It is understood as a matter of course that a variety of variants can be practiced within the scope that does not deviate from the purport of the present invention. For example, a dental implant according to variants of Embodiment 1 of the present invention will be explained hereinafter.

In the above-described Embodiment, a straight abutment that linearly extends from the top end to the bottom end was shown as the abutment 120. However, an abutment for a dental implant is not limited thereto.

FIG. 7 is a diagram for explaining variants of Embodiment 1. FIGS. 7(a) and 7(b) illustrate an abutment for a dental implant according to Variant 1 and Variant 2, respectively.

(Variant 1 of Embodiment 1)

For example, as illustrated in FIG. 7(a), an angled abutment 120a in which a top section 120a2 of the abutment 120a is tilted with respect to a bottom section 120a1 may be used as the abutment for the dental implant of Embodiment 1.

(Variant 2 of Embodiment 1)

Furthermore, as illustrated in FIG. 7(b), an abutment 120b having a structure of a transverse hole that is different from that of Embodiment 1 may be used in place of the abutment 120 of Embodiment 1.

Such an abutment 120b has a structure where an instrument insertion hole 129a, which is different from the instrument insertion hole 129 of the abutment 120 of Embodiment 1, penetrates through the fitting recess 121.

In the abutment 120b with such a structure, the instrument insertion hole (transverse hole) 129a would have openings on both opposing sidewalls of the fitting recess 121 of the abutment 120.

In such an abutment 120b, the remover 80c of the remover device 80 can be inserted from either opening on both sides of the instrument insertion hole 129a, and the workability of the operation to disengage the fitting recess of the abutment 120b secured to the fixture head 112 is thus improved. Furthermore, it is possible to thread a yarn through the instrument insertion hole 129a for preventing the abutment 120 from falling, and such a yarn enables reliable prevention of accidental ingestion of the abutment 120 due to the abutment 120 falling out.

Further, the above-described Embodiment 1 discloses a remover device in which the remover (fit disengaging rod) 80c has a substantially oval-shaped cross section and a uniform thickness across the entire length as the remover device 80 for disengaging an abutment fitted onto a fixture. However, the shape of a remover is not limited thereto.

(Variant 3 of Embodiment 1)

FIGS. 8 and 9 are diagrams (perspective views) for explaining a dental implant according to Variant 3 of Embodiment 1 of the present invention. FIG. 8 schematically illustrates the states prior to and after operating a remover device, seen from the front of an instrument insertion hole of an abutment (FIGS. 8(a) and 8(b)). FIG. 9 schematically illustrates the states prior to and after operating the remover device, seen from the left side surface of the instrument insertion hole of the abutment (FIGS. 9(a) and 9(b)).

For example, as illustrated in FIGS. 8 and 9, a remover 81a of a remover device may be configured such that a tip section 81a1 has a different cross-sectional shape from a body section 81a2 supporting the tip section 81a1.

That is, in such a remover 81a of a remover device, only the tip section 81a1 that touches the top surface 112b1 of the fixture head 112 and the bottom surface 121d1 of the fitting recess 121 when disengaging the fixture 110 fitted into an abutment 120c has a substantially oval-shaped cross section, and the cross-sectional shape of the body section 81a2 that supports such a tip section 81a1 is configured in a circular shape with a diameter that is shorter than the minor axis of the oval-shaped cross-section of the tip section 81a1. Further, an entrance section 129b1 of a transverse hole 129b of the abutment 120c is an oval shape that is the same or slightly larger than the minor axis of the oval-shaped cross-section of the tip section 81a1 of a remover to match the change in the shape of the remover. However, an interior section 129b2 of the transverse hole 129b may be a perfect circle with a major diameter that is larger than the entrance section 129b1.

For the abutment 120c with such a structure, removal operation of the abutment 120c using the remover 81a can be performed similarly to those in Embodiment 1 illustrated in FIGS. 5 and 6. However, if the remover 81a inserted in the transverse hole 129b is rotated to transition from the states illustrated in FIGS. 8(a) and 9(a) to the states illustrated in FIGS. 8(b) and 9(b), the tip section 81a1 of the remover 81a cannot be pulled out from the transverse hole 129b. Thus, unintended fall of the abutment 120c can be prevented more effectively.

Further, in the above-described Embodiment 1, in order to restrict the rotation of the abutment 120 with respect to the fixture 110, the fixture head 112 is configured to comprise the hexagonal prism section 112b (see FIG. 2(a)) and the hexagonal groove section 121b (see FIG. 2(a)) is formed in the longitudinal hole 123 of the abutment 120. However, a configuration for restricting the rotation of an abutment with respect to a fixture is not limited to that in the above-described Embodiment 1.

For example, a polygon-shaped groove section other than a hexagonal groove section (e.g. square groove section), an egg-shaped groove section, a key groove section, a spline groove section, or the like may be formed in the longitudinal hole 123 of the abutment 120 of the above-described Embodiment 1 instead of the hexagonal groove section 121*b*, and the head of the fixture 110 may be configured to fit such a longitudinal hole 123. Further, the configuration for restricting the rotation of the abutment 120 with respect to the fixture 110 may be provided on, for example, an upper prosthetic (crown, bridge, or the like) that is secured to the abutment 120, without providing one in the abutment 120.

Furthermore, a structure for coupling the fixture 110 and the abutment 120 is not limited to a taper connection from fitting them together. For example, a method of using fastening with a screw in conjunction with a taper connection may be employed. For example, a relative movement toward a direction for disengaging the fitting between a fixture and an abutment may be restricted with a screw that is screwed into the fixture from a sidewall of the abutment.

(Variant 4 of Embodiment 1)

FIG. 10 is a diagram for explaining a dental implant according to Variant 4 of Embodiment 1 of the present application. FIG. 10 illustrates a state where gums are formed on a surface of the fixture (FIG. 10(*a*)) and the structure of essential parts of such a dental implant (FIG. 10(*b*)).

Further, in a two-stage implantation method, a fixture is embedded into a jawbone first and an abutment is secured to the fixture in two stages. However, when securing the abutment, the fixture is in a state of being covered with a cortical bone of the jawbone 20 or gums 21, as illustrated in FIG. 10(*a*). For example, only the top surface of the fixture is generally exposed (released) by cutting the gums 21. In addition, there is little strain on a patient.

However, in the above-described Embodiment where the fixture 110 and the abutment 120 are directly coupled, it is necessary to allow the abutment 120 to advance to the outer circumferential section of the fixture 110. Thus, a case where it is difficult to mount an abutment to a fixture is conceivable.

In this regard, a fixture 110*a* of Variant 4 of Embodiment 1 consists of two components, a first component (connector) 1122 constituting a head and a second component (body section) 1121 constituting an embedded section, as illustrated in FIG. 10(*b*) for example.

Further, for the fixture 110*a*, the coupling structure of the first component 1122 and the abutment 120 may be the same as the coupling structure of the fixture 110 and the abutment 120 in the above-described Embodiment.

That is, the connector 1122 has an outer tapered section 1122*a* and a hexagonal prism section 1122*b* having the same structure as the fixture 110 in the above-described Embodiment 1.

Further, as the body section 1121 of the fixture 110*a*, for example, those having a structure of a known fixture or an existing body section (in particular, those with a structure that is compatible with a two-stage implantation method is preferably) can be used. The connector 1122 only needs to be appropriately connectable to the body section 1121. For example, the connector 1122 and the main body section 1121 may be configured to be fastened by threadedly engaging a male screw section formed on the connector 1122 to a female screw section formed on the body section 1121. Coupling of the connector 1122 and the body section 1121 is not limited to fastening with a screw.

(Variant 5 of Embodiment 1)

FIG. 11 is a diagram for explaining a dental implant according to Variant 5 of Embodiment 1 of the present invention.

A dental implant according to Variant 5 of Embodiment 1 comprises an IC implemented fixture 110*b*, which is equipped with an IC chip 113 for storing data related to history of the dental implant in place of a fixture constituting the dental implant of Embodiment 1. Such an IC implemented fixture 110*b* has the same structure as the fixture 110 that constitutes the dental implant of Embodiment 1, except that an IC chip is implemented on a head 110*b*1 thereof.

In an IC chip implemented fixture with such a structure, even after a dental implant is mounted into a patient, it is possible to know information such as the manufacturer and manufactured year of the dental implant by electronically reading out data that is stored in an IC chip.

(Variant 6 of Embodiment 1)

FIGS. 12 and 13 are diagrams for explaining a dental implant according to Variant 6 of Embodiment 1 of the present invention. FIG. 12 schematically illustrates the overall structure of an abutment of such a dental implant. FIG. 13(*a*) is a cross-sectional view illustrating a coupled state of an abutment and an implant. FIG. 13(*b*) is a partially expanded cross-sectional view of FIG. 13(*a*).

A dental implant according to Variant 6 of Embodiment 1 comprises a linked abutment 1000, which is constituted by linking a plurality of abutment sections 1120 that are matched with a plurality of fixtures 110 with a linking section 1130, instead of the abutment constituting the dental implant of Embodiment 1.

Here, similarly to the abutment 120 of Embodiment 1, the abutment section 1120 has a fitting recess 1121 for fitting onto the head 112 of the fixture 110 that is embedded into the jawbone 20. That is, the fitting recess 1121 has an inner tapered section 1121*a* that fits onto the outer tapered section 112*a* of the fixture head 112 and a groove section 1121*b* for receiving the hexagonal prism section 112*b* of the fixture head 112.

The fitting recess 1121 of the abutment 1000 according to Variant 6 of Embodiment 1 is different from the fitting recess 121 of the abutment of Embodiment 1 in that: the fitting recess 1121 is configured so that a space is created between sections other than the edge on the opening side of an inside surface 1125 of the fitting recess 1121 and the outside surface 114 of the outer tapered section 112*a* of the fixture head 112 when the head 112 of the fixture is inserted into the fitting recess 1121; and the groove section 1121*b* constituting the fitting recess 1121 is a circular groove section.

Other structures of such a fitting recess 1121 are the same as those of the fitting recess 121 of the abutment 120 of Embodiment 1.

In Variant 6 of Embodiment 1, an abutment constituted by linking eight abutment sections 1120 with the linking section 1130 is shown as the linked abutment 1000. However, a linked abutment only needs at least two abutment sections linked with a linking section.

Further, Variant 6 of Embodiment 1 shows a linked abutment in which the fitting recess of each of the eight abutment sections 1120 has an instrument insertion hole (transverse hole) 129 for inserting a remover. However, in a linked abutment, it is only necessary for some of fitting recesses of the plurality of abutment sections to have an instrument insertion hole. Further, the instrument insertion hole 129 may be formed on an inside surface facing toward the inside of an oral cavity of the surface of the fitting recess 1121 of the abutment section 1120, or on an outside surface facing out of the oral cavity of the surface of the fitting recess 1121 of the abutment section 1120. Furthermore, the instrument insertion hole 129 may be formed at a position on the surface of the fitting recess 1121, which matches the position of individual fitting recess 1121 in the oral cavity.

Furthermore, in Variant 6 of Embodiment 1, the groove section for receiving the hexagonal prism section of the fixture head 112 is configured as the circular groove section 1121b. Thus, the fitting recess of each abutment section is not structured to restrict the rotation of the abutment section 1120 with respect to the fixture 110.

This is because for the linked abutment 1000 according to Variant 6 of Embodiment 1, when the fixture head 112 fits into the fitting recess 1121 of one abutment section 1120, rotation of the abutment section 1120 with respect to the fixture 110 is naturally restricted by another fitting recess 1120 of the abutment section fitting onto the fixture head 112.

Embodiment 2

FIG. 14 is a diagram for explaining a dental implant set according to Embodiment 2 of the present invention. FIG. 14 illustrates an attached state of a dental implant to a jawbone (FIG. 14(a)) and a fixture, abutment, stent and securing pin for repositioning the dental implant (FIG. 14(b)). FIG. 15 is a perspective view (FIG. 15(a)) and a cross-sectional view (FIG. 15(b)) of the stent used for repositioning the dental implant of Embodiment 2.

A dental implant 200 of Embodiment 2 comprises a fixture 210 constituted so as to be embedded into the jawbone (alveolar bone) 20 and to couple with the jawbone 20, an abutment 220 constituted to be secured to the fixture 210, and an artificial tooth 230 constituted to be attached to the abutment 220 as a top structure. Such an artificial tooth is called a restoration or a prosthetic crown and is also referred to as a restoration hereinafter.

Further, at least the fixture 210, abutment 220, and restoration 230 that constitute the dental implant 200 of Embodiment 2 are comprised in a dental implant set 200s together with a tool that is used for repositioning of a dental implant, i.e., a tubular stent 240 and a securing pin 250. Such a dental implant set 200s is supplied from a manufacturer of dental implants.

Here, the stent 240 and the securing pin 250 are instruments that are used to install a new standardized fixture and a new standardized abutment in place of an existing fixture 210a and an existing abutment 220a (see FIG. 16(a)). Each of the fixture 210 and the abutment 220 constituting the dental implant 200 of Embodiment 2 is standardized to engage the stent 240 and the securing pin 250, in addition to the structure of the fixture 110 and 120 of Embodiment 1. Further, the existing fixture 210a, the existing abutment 220a and the existing restoration 230 constituting the dental implant 200 have the same structure as those in Embodiment 1.

Specifically, the stent 240 has a recess 242 that fits onto a standardized abutment. Furthermore, the stent 240 has an insertion hole 241 that connects to the recess 242. Further, the securing pin 250 is for securing the stent 240 to the standardized abutment 220.

Furthermore, insertion holes 213 and 221 for the securing pin 250 are formed on the standardized fixture 210 and the abutment 220. In addition, the top portion of the standardized abutment 220 is configured to fit into the recess 242 of the stent 240.

Here, the above-described securing pin 250 is formed to a size to the extent such that the securing pin 250 can be inserted into the insertion hole 241 of the stent 240, the insertion hole 221 of the abutment 220, and the insertion hole 213 of the fixture 210. The securing pin 250 can be inserted into the insertion hole 241 of the stent 240, the abutment 220 and the fixture 210 without any space so that they do not move with respect to one another when the securing pin 250 is inserted into the insertion hole 241 of the stent 240, the insertion hole 221 of the abutment 220, and the insertion hole 213 of the fixture 210.

The length of the stent 240, although not limited thereto, can be about 3-7 mm, and is particularly preferable at around 5 mm. Further, the securing pin 250 ideally enters about 5 mm inside the abutment 220, and in such a case, the length of the securing pin 250 is preferably about 10 mm. Here, the standardized abutment 220 and the standardized fixture 210 refer to those, the shape, dimension and the like of which are determined to conform with each component of a dental implant.

Further, the positions of the fixture 210 and the abutment 220 match the positions of the insertion hole 241 for the securing pin 250 in the stent 240 and a drill 260 guided thereby.

(Method of Repositioning)

Next, a method of replacing an existing fixture and an existing abutment with a standardized fixture and a standardized abutment and reusing thereupon an existing restoration by using the dental implant set of Embodiment 2 will be explained.

FIGS. 16 and 17 are diagrams for explaining the repositioning of a dental implant. FIGS. 16(a)-16(g) and FIGS. 17(a)-17(e) illustrate the states of a dental implant at the main stages.

An existing dental implant is attached to the jawbone 20 (FIG. 16(a)). For such an existing dental implant, the existing abutment 220a is detached from the existing fixture 210a together with the existing restoration 230. In this state, the existing fixture 210a is secured to the jawbone 20 (FIG. 16(b)). The abutment 220a and the restoration 230 that are detached from the existing fixture 210a are separated by an operation outside the oral cavity in order to reuse the restoration 230.

Next, a new abutment 220 is secured to the top portion of the existing fixture 210a by a frictional force generated by the fitting of the two, similarly to Embodiment 1 (FIG. 16(c)). The shape, dimension, and the like of the new abutment 220 are standardized as described above.

Subsequently, the tubular stent 240 is attached to the new abutment 220 that is secured to the existing fixture 210a so that the recess 242 fits onto the top portion of the abutment 220. Furthermore, the securing pin 250 is put through the insertion hole 241 and the recess 242 of the stent 240 and the insertion hole 221 of the abutment 220 and is inserted into the existing fixture 210a (FIG. 16(d)). At this time, the stent 240 is positioned along natural teeth and the like that are normally located on both sides of the section where an existing restoration is disposed.

The existing fixture 210a, the new abutment 220, the stent 240, and the securing pin 250 are then detached from the jawbone 20. At this time, the existing fixture 210a is pulled out from the jawbone 20, leaving a hole 20d from pulling out the existing fixture 210a in the jawbone 20 (FIG. 16(e)).

Next, only the stent 240 is installed in the oral cavity as positioned in advance along the natural teeth and the like (FIG. 16(*f*)) and the standardized drill 260 is inserted towards the jawbone 20 from the pin insertion hole 241 of the stent 240 to drill into the jawbone 20 (FIG. 16(*g*)). Thereby, an implant embedding hole 20*d*1 that matches the dimension of the new standardized fixture 210 is formed on the jawbone 20 (FIG. 17(*a*)). In the diagram, 20*d*2 refers to the portion that is drilled out.

Here, the size of an implant embedding hole 20*d*1 is determined as follows. The size of an implant embedding hole is determined by drilling the jawbone 20 with the drill 260 in accordance with the remaining bone. At this time, only the direction of embedding a fixture is determined by the stent 240. When embedding a new fixture, the depth of an implant embedding hole is appropriately set to match the condition of the jawbone after detaching an existing fixture. The length of a new abutment 220 is determined in accordance with such a depth.

Subsequently, the new standardized fixture 210, the new standardized abutment 220, the stent 240, and the securing pin 250 are prepared (FIG. 17(*b*)).

The new standardized fixture 210, the new standardized abutment 220, the stent 240 and the securing pin 250 are combined, and the fixture 210 is embedded into the implant embedding hole 20*d*1 of the jawbone 20 (FIG. 17(*b*)). Here, the new fixture 210 and the new abutment 220 are secured by a frictional force generated by the fitting, similarly to securing of a fixture to an abutment in Embodiment 1.

Next, the securing pin 250 is pulled out from the new fixture 210, the new abutment 220 and the stent 240 (FIG. 17(*c*)). Furthermore, the stent 240 is detached from the abutment 220 (FIG. 17(*d*)).

The abutment 220 that is secured to the new fixture 210 is covered with the restoration 230 that was detached from the existing abutment 220*a* (FIG. 17(*e*)). Thereby, a repositioning, which replaces a fixture and an abutment of an existing dental implant with a new fixture and a new abutment and thereupon reuses an existing restoration, is completed.

In this manner, the dental implant set 200*s* of Embodiment 2 comprises: the stent 240 having the recess 242 that fits onto the standardized abutment 220; and the securing pin 250 for securing the stent 240 to the standardized abutment 220. In addition, the stent 240 is configured such that the posture when the recess 242 of the stent 240 fits onto the standardized abutment 220 attached to the existing fixture 210*a* defines the direction of the standardized fixture 210 that replaces the existing fixture 210*a*. Thus, it is possible to attach a restoration that was attached to the existing abutment 220*a* to the abutment 220 secured to the new fixture 210 by embedding the new standardized fixture 210 replacing the existing fixture 210*a* into the jawbone 20 by using the stent 240. For this reason, when the abutment 220*a* and the fixture 210*a* of a dental implant are replaced, it is possible to avoid wasting the existing restoration 230.

In an implant treatment that uses the dental implant explained in the above-described Embodiment 1, it is necessary to embed a fixture in an appropriate position and direction while considering the condition of the jawbone of a patient.

Especially in the linked abutment explained in Variant 6 of Embodiment 1, when an abutment secured to a fixture is disengaged, a plurality of abutment sections are simultaneously pulled out from fixtures. Thus, it is required that the directions of the axis of the fixtures are each configured to be parallel to each other with high precision.

In this regard, as an invention that meets such a requirement, a dental tap set that is used in a method of forming an implant embedding hole by using a surgical guide will be explained below as Embodiment 3.

Embodiment 3

In a method of installing a dental implant by using a dental tap set according to Embodiment 3 of the present invention, a surgical guide is mounted in an oral cavity and a jawbone is drilled with a drill while a dental drill is mounted in a drill guide hole that is formed on the surgical guide when forming an implant embedding hole. When a jawbone is drilled by using a surgical guide as such, the drilling position and the drilling angle of a drill is determined by a drill guide hole of the surgical guide, enabling the formation of an implant embedding hole in an appropriate position and direction.

Such a surgical guide is designed by simulating the optimal embedding position and embedding direction of an artificial root of a tooth, i.e., fixture, in accordance with the condition of remaining teeth or bone of a patient on a computer, based on an image obtained by a CT image of a jawbone section of the patient. A structural body as a surgical guide constituted by laminating resin is molded by a three-dimensional lamination molding device by inputting design data (three-dimensional image data) into the three-dimensional lamination molding device.

This will be explained in detail by using the figures.

FIG. 18 is a diagram for explaining a dental tap according to Embodiment 3 of the present invention. FIG. 18 illustrates the side view and cross section of the dental tap (FIGS. 18(*a*) and 18(*b*)). Further, FIG. 19 illustrates the overall structure of the dental guide of Embodiment 3 (FIG. 19(*a*)) and a guide sleeve attached to the dental guide (FIG. 19(*b*)). Furthermore, FIG. 20 is a side view (FIG. 20(*a*)) and a cross-sectional view (FIG. 20(*b*)) of the guide sleeve of the dental guide.

Such a dental tap set comprises a dental tap 410 and a dental guide SG. The dental tap set is for forming a screw groove in an implant embedding hole that is formed in a jawbone for embedding a dental implant.

The dental tap 410 comprises a tap body 411 that is screwed into an implant embedding hole 20*a* so that a screw groove is formed in the implant embedding hole 20*a* (FIG. 23(*a*)) and a tap holding section 412 that is provided on one end of the tap body 411. A screw thread 411*a* for forming a screw groove in an implant embedding hole is formed on the outer circumferential surface of the side section Th on the other end of the tap body 411. Here, screw threads 411*a* of the tap body 411 constitute a double threaded screw. Further, a spiral groove 411*b* is also formed on the outer circumferential surface of the tap body 411 to enable smooth discharge of bones that are drilled out by tapping.

Meanwhile, a dental guide SG is a surgical guide comprising a guide sleeve 420. The guide sleeve 420 is used as a guide member of a dental drill D when forming the implant embedding hole 20*a* with the dental drill D. Furthermore, the guide sleeve 420 is used as a guide member of the dental tap 410 when forming a screw thread in the implant embedding hole 20*a* with the dental tap 410. The guide sleeve 420 has a guide hole 420*a* for guiding the dental drill D and the dental tap 410. A screw groove 421 is formed on the inner surface of the guide hole 420*a* so as to threadedly engage the screw thread 411*a* formed on the outer circumferential surface of the tap body 411.

The guide sleeve 420 is attached to a surgical guide that is molded based on design data from a computer such that the axis of the guide hole 420a matches with the axis of a fixture to be embedded.

Next, a method of forming the implant embedding hole 20a having a screw groove on the jawbone 20 by using a dental tap set will be explained.

FIGS. 21-23 are diagrams for explaining a method of using the dental tap set according to Embodiment 3 of the present invention. FIGS. 22 and 23 illustrate a dental guide and a guide sleeve. However, only a guide sleeve of a dental guide is illustrated in FIG. 21.

As illustrated in FIGS. 21(a) and 22(a), after cutting open a mucous membrane 22 on the alveolar ridge (oral cavity) side of the jawbone (alveolar bone) 20, the dental guide SG is secured to the jawbone 20 and the jawbone 20 is drilled with the dental drill D while the dental drill D is inserted in the guide hole 420a of the guide sleeve 420. The implant embedding hole 20a is thereby formed on the jawbone 20, as illustrated in FIGS. 21(b), 22(b), and 22(c).

At this time, the drill D is mounted on a drill chuck Dc of a drill head Dh. A member with a length La1, including both of the drill head Dh and the surgical guide SG, is inserted in an oral cavity (see FIG. 22(b)).

Here, the dental guide (surgical guide) SG may be secured by hand. However, for example, when there is impairment on the free end, the dental guide may be secured to a tooth that is adjacent to the section with tooth impairment. In this case, a portion for securing the tooth adjacent to the section with the tooth impairment may be provided on the dental guide SG.

Subsequently, as illustrated in FIGS. 21(c) and 23(a)-23(c), the screw thread 411a of the dental tap 410 is threadedly engaged to the screw groove 421 that is formed in the guide hole 420a of the guide sleeve by screwing the dental tap 410 into the guide hole 420a of the guide sleeve 420 of the dental guide SG by hand. For this reason, a force to enter the jawbone 20 is generated for the dental tap 410 by rotating the dental tap 410. Thus, the dental tap 410 would advance into the implant embedding hole 20a while forming the screw groove 20a1 on the inner surface of the implant embedding hole 20a by the screw thread 411a on the outer circumferential surface of the dental tap. When the dental tap 410 is screwed into the guide hole 420a, a member with a length La2, including both of the dental tap 410 and the surgical guide SG, is inserted in the oral cavity (see FIG. 23(b)).

The screw groove 20a1 is formed to a predetermined depth in the implant embedding hole 20a (FIG. 21(d), FIG. 23(c)). The dental tap 410 is then pulled out from the jawbone 20, and the dental guide 420 is detached from the jawbone 20 (FIGS. 21(e) and FIG. 23(d)).

The fixture 100 of the dental implant illustrated in Embodiment 1 is then screwed into the implant embedding hole 20a, to which the screw groove 20a1 is formed, to secure the fixture to the jawbone 20 (FIG. 21(f)).

Thereafter, the abutment 120 is secured to the fixture 100 by a frictional force from the fitting, as explained in Embodiment 1. Furthermore, the restoration 130 is attached to the abutment 120 that is secured to the fixture 100 to complete the installation of the dental implant.

In this manner, the drill D is guided by the dental guide (surgical guide) SG when forming the implant embedding hole 20a in Embodiment 3. Furthermore, when forming a screw hole on the implant embedding hole 20a by using the dental tap 410, since the same dental guide as the dental guide SG that is used in the formation of an implant embedding hole is used, the implant embedding hole can be formed in the position and direction as designed. In addition, when a screw groove is formed on such an implant embedding hole, a dental tap can be screwed into a jawbone with non-uniform hardness without any misalignment. As a result, it is possible to embed a fixture into a jawbone in an optimal position toward an optimal direction that are obtained by a computer analysis of the jawbone.

It is possible to materialize installation precision that is required for a fixture for installing a linked abutment by precisely setting an embedding position and an embedding direction of the fixture in this manner.

The screw thread 411 of the dental tap 410 in the Embodiment 3 described above is not limited to those constituting a double-threaded screw. The screw thread may also be those constituting a single-threaded screw. Further, the screw thread 411 of the dental tap 410 may also be those constituting a multi-threaded screw other than a double-threaded screw.

Further, in the above-described Embodiment 3, the above-described dental tap 410 may be those with a cutting section for cutting out a cortical bone that constitutes a jawbone at the tip of the section on the other end of the tap body 411. Such a dental tap can be used as a tap for a maxillary sinus floor augmentation procedure. Hereinafter, a dental tap set comprising such a dental tap will be explained as a variant of Embodiment 3.

(Variant of Embodiment 3)

Next, a dental tap set according to the Variant of Embodiment 3 of the present invention will be explained.

FIG. 24 is a diagram for explaining a dental tap set according to the Variant of Embodiment 3 of the present invention. FIG. 24 illustrates a side surface and a cross-section of a dental guide of such a dental tap set (FIGS. 24(a) and 24(b)).

The dental tap set according to the Variant of Embodiment 3 comprises a tap for a maxillary sinus floor augmentation procedure (hereinafter, also referred to as a dental tap) in place of the dental tap of the dental tap set according to Embodiment 3. The other configurations are the same as the dental tap set according to Embodiment 3.

For a dental tap 410a of the dental tap set according to the Variant of Embodiment 3, a cutting section 413 for cutting out a cortical bone that constitutes a jawbone is formed on the other end of the tap body 411 of the dental tap 410 in the above-described Embodiment 3. The other configurations are the same as the dental tap 410 of Embodiment 3.

Next, a socket lift procedure, which is performed by using the tap set according to the Variant of Embodiment 3, will be explained.

FIG. 25 is a diagram for explaining a method of using the dental tap set according to the Variant of Embodiment 3, which sequentially illustrates the steps for forming a screw groove in an implant embedding hole (FIGS. 25(a)-25(f)).

First, as illustrated in FIG. 25(a), a mucous membrane 32 on the alveolar ridge (oral cavity) side of a maxillary alveolar bone 31 is cut open, and as illustrated in FIG. 25(b), a drill (and a reamer) is used to form a tap pilot hole (implant embedding hole) 35 from the alveolar ridge side of the maxillary alveolar bone 31, so that at least a portion of a cortical bone 34 on the maxillary sinus 33 side of the maxillary alveolar bone 31 remains. Here, the dental guide SG comprising the guide sleeve 420, which is explained in Embodiment 3, is used upon forming such a tap pilot hole 35.

Next, as illustrated in FIG. 25(c), the dental guide SG that is used for guiding the dental tap 410a is secured outside the tap pilot hole 35. The screw thread (male screw) 411a for tapping that is provided on the outer circumferential surface of the dental tap 410a is then threadedly engaged to the screw groove (female screw) 421 on the guide sleeve 420 of the dental guide SG, and the dental tap 410a is screwed into the tap pilot hole 35 by hand to perform tapping.

Here, the male screw 411a of the dental tap 410a has substantially the same shape as the male screw 111a that is provided on the outer circumferential surface of the fixture 110 of the dental implant used later. In the Variant of Embodiment 3, the male screw is a double threaded screw. Further, the spiral groove 411b for a smooth discharge of bones that are drilled out by tapping is provided on the outer circumferential surface of the dental tap 410a (see FIG. 24(a)).

The dental guide SG may be secured by hand. For example, when there is impairment on the free end, the dental guide may be secured to a tooth that is adjacent to the section with tooth impairment. In this case, a portion for securing the tooth adjacent the section with the tooth impairment may be provided on the dental guide SG.

Subsequently, as illustrated in FIG. 25(d), when the dental tap 410a that is screwed into the tap pilot hole 35 reaches the cortical bone 34 that remains on the side away from the maxillary sinus 33, the cortical bone 34 is cut out in a discoidal shape, a mucous membrane of the maxillary sinus 36 is pushed up into the maxillary sinus 33 with a cortical bone 34a that was cut out, and a portion of the mucous membrane of the maxillary sinus 36 is detached from the maxillary alveolar bone 31.

Here, the cutting section 413 for cutting out the cortical bone 34 that remains on the side away from the maxillary sinus 33 is provided on the tip of the dental tap 410a. The cutting section 413 is shaped such that the tip surface of the dental tap 410a is depressed in a bowl shape and the inner surface of the depressed portion is a steeply inclined plane.

Subsequently, an artificial bone 37 is filled in a space formed between the maxillary alveolar bone 31 and the mucous membrane of the maxillary sinus 36 (see FIG. 25(e)). After supplementing the depth of a bone for embedding an implant with the artificial bone 37, the fixture 110 for the dental implant of Embodiment 1 is embedded to the maxillary alveolar bone 31 (see FIG. 25(f)).

Here, a patient's own bone that is collected from another site may be used instead of the artificial bone 37. Furthermore, another person's bone may be used.

In a socket lift procedure that is performed as described above by using the tap set of the present Embodiment, the following effects are obtained.

First, when the dental tap 410a is screwed into the tap pilot hole 35 by hand and a portion of the cortical bone 34 is cut out by the cutting section 413 of the dental tap 410a, the dental tap 410a can be advanced gradually by screwing in. Thus, there is barely any risk of the dental tap 410a penetrating through the mucous membrane of the maxillary sinus 36. Therefore, easiness and enhanced safety of operation for an implant treatment can be obtained. In addition, since it is possible to depend on the sensitive feel of the fingertips when screwing in the dental tap 410a, operational easiness and safety are ensured.

Further, if the dental tap set according to the Variant of Embodiment 3 is used, reliable embedding of the fixture 110 in a desirable direction is facilitated.

A common socket lift procedure will be briefly explained for comparison with the socket lift procedure according to the Variant of Embodiment 3.

FIG. 26 is a diagram for explaining a method of embedding a fixture (implant) for a dental implant by a common socket lift procedure. FIG. 26 sequentially illustrates the major steps (FIGS. 26(a)-26(f)).

In a common socket lift procedure, first, as illustrated in FIG. 26(a), the mucous membrane 32 on the alveolar ridge (oral cavity) side of the maxillary alveolar bone 31 is cut open, and as illustrated in FIG. 26(b), a drill (and a reamer) is used to form a tap pilot hole (implant embedding hole) 50 from the alveolar ridge side of the maxillary alveolar bone 31 so that at least a portion of the cortical bone 34 on the maxillary sinus 33 side of the maxillary alveolar bone 31 remains.

As illustrated in FIGS. 26(c) and 26(d), the tip of an instrument (osteotome) 51 is then inserted in the tap pilot hole 50; the rear end section of the instrument 51 is malleted to punch out the cortical bone 34 that remains on the side way from the maxillary sinus 33 in a discoidal shape; and the mucous membrane of the maxillary sinus (Schneiderian membrane) 36, which separates the maxillary alveolar bone 31 and the maxillary sinus 33, is pushed up into the maxillary sinus 33 with the punched out alveolar bone 34a to detach a part of the mucous membrane of the maxillary sinus 36 from the maxillary alveolar bone 31. In addition, a space that is formed by the detachment between the maxillary alveolar bone 31 and the mucous membrane of the maxillary sinus 36 is filled with artificial bone 37 (FIG. 26(e)). After supplementing the depth of a bone for embedding an implant with the artificial bone 37, an implant 38 is embedded in the maxillary alveolar bone (see FIG. 26(f)).

In such a common socket lift procedure, when the implant (fixture) 110 is screwed into and embedded into the maxillary alveolar bone 31 as illustrated in FIG. 26(f), the density and hardness of the maxillary alveolar bone 31 are not uniform. For example, when the hardness of the bone on the right side and that on the left side of the direction of advancement (embedding) of the implant 38 are different, there is a tendency for the implant to advance by leaning toward the softer bone, and thus there is a risk that embedding toward a desirable direction becomes difficult unless the diameter of the implant 38 is enlarged and the male screw 411a is made more shallow. In addition, when an external force in the axis direction, which is unrelated to screwing in the implant 38 in the axial direction, is applied to the implant 38 that is screwed into the maxillary alveolar bone 31, there is a risk of destroying a screw groove that is formed by self-tapping by the implant 38 itself.

In contrast, in the socket lift procedure that uses the dental tap set according to the Variant of Embodiment 3, tapping is performed prior to the embedding of the implant 110. In addition, such tapping can be performed well such that the dental tap 410a is guided to a desirable direction and an external force unrelated to screwing is not applied to the dental tap 410a by the guide sleeve 420 of the surgical guide (dental guide) SG. For this reason, diagonal advancement of the implant 110 and destruction of a screw groove can be prevented to readily ensure embedding of an implant in a desirable direction. Further, it is not necessary to enlarge the diameter of the implant 110 or to make the male screw 411a shallower. In addition, the diameter of the implant 110 can be reduced and the male screw 411a can be made deeper.

The male screw 411a of the dental tap 410a in the Embodiment described above is not limited to a double-threaded screw. The male screw may also be a single-threaded screw or a multi-threaded screw other than a double-threaded screw.

Further, a dental tap set may be configured to comprise a plurality of dental taps 410a having male screws 411a with heights (depth) that are different from each other such that tapping is performed by sequentially using the plurality of dental taps 410a so that grooves formed becomes gradually deeper. In this case, it is not necessary to provide the cutting section 413 to all of the plurality of dental taps 410a. For example, if the cutting section 413 is not provided to the dental taps 410 that is used in the step illustrated in FIG. 25(d) (step of lifting the cortical bone 34a that is cut out and the mucous membrane of the maxillary sinus 36), damage to the mucous membrane of the maxillary sinus 36 by the cutting section 413 can be effectively prevented. Further, in this case, the dental guide SG may be configured to guide all of the dental taps 410a. Alternatively, for example, the dental guide SG may be configured to guide only the dental tap 410a that is used in the initial stage of tapping a tap pilot hole (i.e., stage for forming a shallow screw groove).

Furthermore, the cutting section 413 of the dental tap 410a in the Variant of the Embodiment described above has a shape where the tip surface of the dental tap 410a is depressed in a bowl shape and the inner side surface of the depressed portion is a steeply inclined surface (FIG. 27(a)). However, the shape of a cutting section is not limited thereto.

A cutting section 413b of a dental tap 410b has a shape where the tip surface of the dental tap 410a is depressed in an arcuate shape and the inner side surface of the depressed portion is a gently inclined surface (FIG. 27(b)).

Further, both cutting sections 413a and 413b of the dental taps 410a and 410b, which are illustrated in FIGS. 27(a) and 27(b), have a shape that is sharp on the edge. However, a dental tap may have a shape that is rounded at the edge of a cutting section.

For example, a cutting section 413c of a dental tap 410c illustrated in FIG. 27(c) is a cutting section that is given roundness to the edge of the cutting section 413a of the dental tap 410a. A cutting section 413d of a dental tap 410d illustrated in FIG. 27(d) is a cutting section that is given roundness to the edge of the cutting section 413b of the dental tap 410b.

In Embodiment 3 and the Variant thereof described above, a surgical guide is used to precisely determine the position and direction of an implant embedding hole. However, when forming an implant embedding hole by using a surgical guide, it is necessary to have a patient open his/her mouth wide, as illustrated in FIG. 22(b). This is because when using a surgical guide, it is necessary to dispose a chuck section of a dental drill in an oral cavity so that the dental drill D with a length that corresponds to the depth of an implant embedding hole is inserted in the guide hole 420a of the guide sleeve 420 of the surgical guide SG while mounting the surgical guide in the oral cavity of a patient.

In this regard, a dental drill that materializes a method of alleviating such strain on a patient will be explained below as Embodiment 4.

Embodiment 4

Next, a dental drill according to Embodiment 4 of the present invention will be explained.

FIG. 28 is a diagram for explaining a dental drill according to Embodiment 4 of the present invention. FIG. 28 illustrates such a dental drill and a rod-shaped guide for guiding the dental drill (FIG. 28(a)) and states of use of the dental drill and the rod-shaped guide (FIGS. 28(b)-28(d)).

A dental drill 300 of Embodiment 4 is a dental drill for forming the implant embedding hole 20a (see FIG. 32(b)) for embedding the dental implant 100 (see FIG. 34(c)) in the jawbone 20. Such a dental drill 300 has a drill body 310 for drilling the jawbone 20 and a drill support 320 for supporting the drill body 310. The drill support 320 is a section that is held by a drill chuck Dc1 of a drill head Dh1 (see FIG. 29(b)).

Here, the drill body 310 has a throughhole 311 for inserting a rod-shaped guide 350 (see FIG. 28(c)) and is configured to be rotatable and to be movable along the rod-shaped guide 350 while having the rod-shaped guide 350 inserted in the throughhole 311. The implant embedding hole 20a is formed by drilling the jawbone 20 by rotating the drill body 310 and entering the drill body 310 into the jawbone 20.

Such a drill body 310 is a cylindrical body, and drilling blades 313 are formed along the circumferential edge on one end of the cylindrical body 310. Further, helical protruding lines 312 are formed on an outer circumferential surface 310a of the drill body 310. In addition, drilling scrap generated by drilling the jawbone 20 when forming the implant embedding hole 20a is discharged from a region between adjacent helical protruding lines (i.e., helical groove). Furthermore, a plurality of water pouring holes (not shown) for pouring physiologic saline or the like on a drilled section may be formed on a sidewall of the cylindrical drill body 310.

Further, the rod-shaped guide 350 for guiding the dental drill 300 comprises: an embedded section 352 that is embedded into the jawbone 20; and a guiding section 351, which is integrally formed with the embedding section 352, for guiding the dental drill 300.

FIG. 29 is a diagram for illustrating a guide member (surgical guide) for use in positioning a rod-shaped guide of the dental drill according to Embodiment 4 of the present invention. FIG. 29 illustrates the overall structure of the guide member (FIG. 29(a)) and a guide sleeve that is attached to the guide member (FIG. 29(b)).

A guide member SG1 is a guide member (surgical guide) that is used to form a guide mounting hole 20c for attaching the rod-shaped guide 350 on the jawbone 20 (see FIG. 30(b)). Such a guide member SG1 is designed by simulating the optimal embedding position and embedding direction of an artificial root of a tooth, i.e., fixture, in accordance with the condition of remaining teeth or bone of a patient on a computer, based on an image obtained by a CT image of a jawbone section of the patient. A structural body is molded as a surgical guide constituted by laminating resin by a three-dimensional lamination molding device by inputting design data (three-dimensional image data) into the three-dimensional lamination molding device.

Such a surgical guide SG1 is mounted on a tooth of a patient for example, and a guide sleeve Gs for guiding the drill D1 is integrated into the surgical guide SG1. Further, a guide hole Gh for guiding the drill chuck section Dc1 for holding the drill D1 is formed on the guide sleeve Gs. When the drill chuck section Dc1 is mounted in the guide hole Gh, the axial direction of the drill D1 that is held by the drill chuck section Dc1 is matched with the axial direction of a dental implant to be embedded. That is, the surgical guide SG1 is formed so that the direction of the guide hole Gh is oriented in a predetermined direction (axial direction of a dental implant) by mounting the guide sleeve Gs on the surgical guide SG1. Further, such a guide sleeve Gs is for guiding a dental tap Ta (see FIG. 33(a)) for forming a screw groove on the inner surface of the implant embedding hole 20*a* (see FIG. 32(*b*)) with the guide hole Gh formed on the guide sleeve Gs.

Next, a method of forming the implant embedding hole 20*a* on the jawbone 20 by using such a dental drill 300 will be explained.

FIGS. 30-34 are diagrams for explaining a method of forming an implant embedding hole and a method of installing a dental implant. FIGS. 30(*a*)-30(*d*), FIGS. 31(*a*)-31(*c*), FIGS. 32(*a*)-32(*b*), FIGS. 33(*a*)-33(*c*), and FIGS. 34(*a*)-34(*c*) illustrate processing at major steps.

First, the surgical guide SG1 is mounted in the oral cavity so as to cover the jawbone (alveolar bone) 20 of the section where a dental implant is to be embedded, and then the drill chuck section Dc1 for holding the drill D1 is inserted into the guide hole Gh of the guide sleeve Gs (FIGS. 30(*a*) and 30(*b*)). At this time, the axial direction of the drill D1 that is held by the drill chuck section Dc1 matches the axial direction of the dental implant to be embedded.

If the drill chuck section Dc1 is moved toward the jawbone 20 side in this state (FIG. 30(*c*)), the drill D1 drills the jawbone 20 to form the guide mounting hole 20*c* for mounting the rod-shaped guide 350.

The drill D1 is then pulled out from the jawbone 20 and the surgical guide SG1 (FIG. 30(*d*)), and the surgical guide SG1 is removed from the oral cavity (FIG. 31(*a*)).

Subsequently, the rod-shaped guide 350 is inserted into the guide mounting hole 20*c* that is formed on the jawbone 20 and is secured to the jawbone 20 (FIG. 31(*b*)).

Furthermore, the dental drill 300 that is held by a drill chuck Dc2 of a drill head Dh2 is disposed so that the rod-shaped guide 350 that is secured to the jawbone 20 is inserted into the throughhole 311 (FIG. 28(*c*)) of the dental drill 300 (FIG. 31(*c*)), and the dental drill 300 is moved toward the jawbone 20 side along the rod-shaped guide 350 (FIG. 32(*a*)). When the dental drill 300 is moved as such, as illustrated in FIGS. 28(*b*)-28(*d*), the dental drill 300 is guided by the rod-shaped guide 350 to dig through the jawbone 20 along the axial direction of the dental implant. Thereby, the implant embedding hole 20*a* is formed along the axial direction of the rod-shaped guide 350 on the jawbone 20.

Subsequently, the dental drill 300 is pulled out from the jawbone 20 with the rod-shaped guide 350 (FIG. 32(*b*)), and a screw groove is then formed on the inside surface of the implant embedding hole 20*a* by using the dental tap Ta and the surgical guide SG1, which was used in the formation of the guide mounting hole 20*c*.

Here, the dental tap Ta comprises a screw forming section Ta1, on which a screw thread for forming a screw groove on the inside surface of the implant embedding hole 20*a* is formed, and a holding section Ta2. The dental tap Ta is configured such that the screw forming section Ta1 is guided by the inside surface of the guide hole Gh of the guide sleeve Gs1 and a screw groove that is formed in the guide hole Gh threadedly engages the screw thread of the dental tap Ta.

Hereinafter, a method of forming a screw thread in the implant embedding hole 20*a* to install a dental implant will be briefly explained.

As illustrated in FIG. 33(*a*), the dental tap Ta is inserted in the guide hole Gh of the guide sleeve Gs while the surgical guide SG1 is mounted on the jawbone 20, and the dental tap Ta is screwed in toward the direction guided by the guide hole Gh (FIG. 33(*b*)). Thereby, a screw thread is formed on the inside surface of the implant embedding hole 20*a*.

At this time, a plurality of dental taps having screw threads with different heights may be used sequentially from those with a lower screw thread as the dental tap Ta to form screw threads with predetermined heights on the inside surface of the implant embedding hole 20*a*.

Next, the dental tap Ta is detached from the jawbone 20 (FIG. 33(*c*)). Furthermore, after detaching the surgical guide SG1, as illustrated in FIGS. 34(*a*) and 34(*b*), the fixture 100 that constitutes the dental implant of Embodiment 1 is embedded in the implant embedding hole 20*a* that is formed on the jawbone 20. The abutment 120 of the dental implant of Embodiment 1 is then secured to the fixture 110 that is embedded in the jawbone 20. Furthermore, the restoration 130 is attached to the abutment 120.

By using the dental drill 300 of Embodiment 4 with the rod-shaped guide 350 in this manner, it is not necessary that the guide mounting hole 20*c* for securing the rod-shaped guide 350 to the jawbone 20 is formed deep as in the case of forming an implant embedding hole on a jawbone. Thus, the drill D1 for forming the guide mounting hole 20*c* can be short. That is, while a member with a length Lb1, including both of the drill head Dh1 and the surgical guide SG1, is inserted into the oral cavity as illustrated in FIG. 30(*b*), since the surgical guide SG1 is thinner than the surgical guide used in Embodiment 3 and the length of a drill is shorter in comparison to the drill in Embodiment 3, opening of the mouth of a patient can be smaller. Furthermore, since a thick surgical guide SG is not used as in Embodiment 3 when an implant embedding hole is drilled with the dental drill 300, the opening of the mouth of a patient can be reduced to a height Lb2 (FIG. 31(*c*)) corresponding to both of the exposed section of the rod-shaped guide 350 and the drill head Dh2. Further, when performing tapping of the implant embedding hole 20*a*, the opening of the mouth of a patient can be reduced by using the surgical guide SG1 that was used to open an insertion hole for the rod-shaped guide 350 (see FIG. 33(*c*)).

Thus, it becomes unnecessary to have a patient open his/her mouth wide when forming the guide mounting hole 20*c*.

Further, the dental drill 300 for forming an implant embedding hole is a cylindrical body and has the throughhole 311 for inserting the rod-shaped guide 350. Thus, an implant embedding hole for embedding a fixture can be formed in an appropriate position and direction by drilling the jawbone 20 while the rod-shaped guide 350 secured to the jawbone 20 is inserted in the throughhole 311 of the dental drill 300.

Further, when receiving and embedding a bone from another person instead of a bone of a patient for use, use of the dental drill 300 and the rod-shaped guide 350 of Embodiment 4 enables the formation of an implant embedding hole for embedding a fixture in an appropriate position and direction in a section where a bone from another person is embedded in a jawbone in one treatment, and enables an expensive regenerative treatment without failure.

In the above-described Embodiment 4, a case is illustrated where tapping is performed on an implant embedding hole by using a dental guide that was used in the formation of a guide mounting hole for a rod-shaped guide, as in Embodiment 3, after forming the implant embedding hole by a dental drill. However, a method of performing tapping on an implant embedding hole is not limited to the method explained in Embodiment 4.

Further, there are cases where it is not necessary to perform tapping on an implant embedding hole, depending on the structure of a fixture to be embedded. In such a case, tapping is not performed after the formation of an implant embedding hole.

(Variant 1 of Embodiment 4)

Hereinafter, a dental drill that is shorter that the dental drill used in Embodiment 4 and a method of use thereof will be explained as Variant 1 of Embodiment 4 of the present invention.

FIGS. 35 and 36 are diagrams for explaining a method of forming an implant embedding hole by using a dental drill according to Variant 1 of Embodiment 4 of the present invention. FIGS. 35 and 36 illustrate the processing at the major steps of such a method (FIGS. 35(a)-35(c) and FIGS. 36(a)-36(g)).

A dental drill 300a according to Variant 1 of Embodiment 4 is for forming a drilling hole of about the same depth as the guide mounting hole 20c for mounting the rod-shaped guide 350 that is used in Embodiment 4 as a part of an implant embedding hole (hereinafter, also referred to as an implant embedding guidance hole) 20d. The dental drill 300a is shorter than the dental drill 300 used in Embodiment 4 for forming an implant embedding hole that is deeper than the guide mounting hole 20c.

Hereinafter, a method of forming an implant embedding hole by using such a dental drill 300a and the rod-shaped guide 350 will be explained.

Processing up to the mounting of the rod-shaped guide 350 onto the jawbone 20 is performed similarly to the case of using the dental drill of Embodiment 4 (FIGS. 35(a) and 35(b)).

The dental drill 300a that is held by the drill chuck Dc2 of the drill head Dh2 is then disposed so that the rod-shaped guide 350 that is secured to the jawbone 20 is inserted in a throughhole (not shown) of the dental drill 300a (FIG. 35(c)), and the dental drill 300a is moved toward the jawbone 20 side along the rod-shaped guide 350 (FIG. 36(a)). When the dental drill 300a is moved as such, as explained in Embodiment 4, the jawbone 20 is drilled through along the axial direction of a dental implant by the dental drill 300a being guided by the rod-shaped guide 350.

Subsequently, the dental drill 300a is pulled out from the jawbone 20 with the rod-shaped guide 350 (FIG. 36(b)), thereby a portion of the implant embedding hole 20a along the axial direction of the rod-shaped guide 350 is formed as the implant embedding guidance hole 20d on the jawbone 20 (FIG. 36(c)). When the dental drill 300a is pulled out from the jawbone 20 with the rod-shaped guide 350, there are cases where an annularly drilled groove 20b is formed, which is formed by a drilling blade of the dental drill 300a around the guide mounting hole 20c as illustrated in FIG. 36(b), depending on the difference between the inner diameter of the dental drill 300a and the outer diameter of the rod-shaped guide 350. In such a case, a normal dental drill is used to drill a cylindrically-remaining jawbone between the guide mounting hole 20c and the annularly drilled groove 20b to form the implant embedding guidance hole 20d (FIG. 36(c)).

Furthermore, another hollow drill 300b for drilling at deep depth is used and inserted in the implant embedding guidance hole 20d (FIG. 36(d)) to drill the bottom section of the implant embedding guidance hole 20d (FIG. 36(e)). Thereby, an annularly drilled groove 20d1 is formed on the bottom surface of the implant embedding guidance hole 20d (FIG. 36(f)). In a state where the annularly drilled groove 20d1 is formed as such on the bottom surface of the implant embedding guidance hole 20d, a normal dental drill (not shown) is further used to drill the implant embedding guidance hole 20d to form the implant embedding hole 20a (FIG. 32(g)).

Similarly to Embodiment 4, a screw groove is then formed on the inside surface of the implant embedding hole 20a by using the dental tap Ta and the surgical guide SG1 that was used in the formation of the guide mounting hole 20c.

The opening of the mouth of a patient, i.e., a height combining the dimension of the exposed section of the rod-shaped guide 350 and the dimension of the drill head section, can be reduced to a shorter dimension (Lb3) (FIG. 35(c)) in comparison to the dimension (Lb2) of Embodiment 4 by using the dental drill 300a according to Variant 1 of Embodiment 4 in this manner, for the amount the dental drill 300a is shorter than the dental drill of Embodiment 4. Thereby, strain on a patient from having to open his/her mouth wide during an implant treatment is further alleviated.

In the above-described Variant 1 of Embodiment 4, the length of a dental drill that is used with a rod-shaped guide is shortened to alleviate strain on a patient from opening the mouth open wide. However, another structure of a dental drill for alleviating strain on a patient from opening the mouth wide will further be explained as Variant 2 of Embodiment 4.

(Variant 2 of Embodiment 4)

FIG. 37 is a diagram for explaining a dental drill according to Variant 2 of Embodiment 4 of the present invention. FIG. 37 illustrates such a dental drill and the rod-shaped guide thereof (FIG. 37(a)), a cross-section at the Xa-Xa line of FIG. 37(a) (FIG. 37(d)), a method of engaging the dental drill with the rod-shaped guide (FIGS. 37(b) and 37(c)), a cross-section at the Xb-Xb line of FIG. 37(b) (FIG. 37(e)), and a cross-section at the Xc-Xc line of FIG. 37(c) (FIG. 37(f)).

Similarly to the dental drill 300 (FIG. 32) or 300a (FIG. 36) in Embodiment 4 or Variant 1 thereof, a dental drill 500 according to Variant 2 of Embodiment 4 is for forming the implant embedding hole 20a (see FIG. 32(b)) or the implant embedding guidance hole 20d (see FIG. 36(c)) by being guided by a rod-shaped guide 450 that is attached to a jawbone. Further, the rod-shaped guide 450 is substantially the same as the rod-shaped guide 350 (see FIGS. 31 and 35) that is used as a guide for the dental drill 300 (or dental drill 300a) of Embodiment 4 (or Variant 1 thereof). The rod-shaped guide 450 has an embedded section (leg section) 452 that is embedded in a jawbone and a guide section (head) 451, which is integrally formed with the embedded 452 and guides the dental drill 500 (see FIG. 37).

Here, the dental drill 500 has a drill body 510 for drilling the jawbone 20 and a drill support 520 for supporting the drill body 510, as illustrated in FIG. 37. Such a drill support 520 is a section that is mounted on a drill head Dh3, similarly to the dental drill of Embodiment 4 or Variant 1 thereof.

Further, the drill body 510 has a throughhole 510a (see FIG. 37(d)) for inserting the rod-shaped guide 450. The drill main body 510 is configured to be rotatable and to be movable along the rod-shaped guide 450 while the rod-shaped guide 450 is inserted in the throughhole 510a. The implant embedding hole 20a (see FIG. 32(b)) or the implant embedding guidance hole (see FIG. 36(c)) 20d is formed by the jawbone 20 being drilled from the rotation of the drill body 510 and the entry into the jawbone 20.

The drill body 510 of the dental drill 500 is a cylindrical body, and a drilling blade 512 is formed along the circumferential edge on one end of the cylindrical body 510, similarly to the drill body 310 of Embodiment 4 or the like. Further, helical protruding lines 514 are formed on a sidewall (outer circumferential surface) 510b of the drill body 510. In addition, drilling scrap, which is generated by drilling the jawbone 20 when forming the implant embedding hole 20a or the implant embedding guidance hole 20d, is discharged from a region between adjacent helical protruding lines 514, i.e., a helical groove. Furthermore, a plurality of water pouring holes 513 for pouring physiologic saline or the like on a drilled section may be formed on the sidewall 510b of the cylindrical drill body 510, as illustrated in FIG. 37.

Furthermore, the drill body 510 has an incision 511 that is formed at the bottom end of the sidewall 510b so that the rod-shaped guide 450 secured to a jawbone passes through the sidewall 510b of the drill body 510. Such an incision 511 is formed with a width to an extent that enables the guide section 451 of the rod-shaped guide 450 to pass through, from the tip of the drill body 510 where the drilling blade 512 is formed toward the drill support 520 side. That is, the width of the incision 511 is about the same as the width of the guide section 451 of the rod-shaped guide 450, and the height of the incision 511 (dimension in the direction along the rotational axis of a drill) is a dimension that substantially matches the length of the guide section 451 of the rod-shaped guide 450.

In the dental drill 500 according to Variant 2 of Embodiment 4 with such a configuration, as illustrated in FIGS. 37(c) and 37(f), when the drill body 510 is disposed so that the guide section 451 of the rod-shaped guide 450 is positioned in the throughhole 510a of the drill body 510, as illustrated in FIGS. 37(b) and 37(e), the guide section (head) 451 of the rod-shaped guide 450 that is mounted on the jawbone 20 relatively passes through the incision 511 of the dental drill 500 to enter the throughhole 510a of the dental drill 500 by merely having the tip of the dental drill 500 that is mounted on the drill head Dh3 move parallel along the jawbone 20.

For this reason, even when the dental drill 500 is mounted on the rod-shaped guide 450 while the dental drill 500 is inserted in the oral cavity, it is not necessary to lift the dental head Dh3 where the dental drill 500 is mounted, for the amount of the height of the guide section 451 in order to avoid interference between the tip of the dental drill 500 and the guide section 451 of the rod-shaped guide 450. In other words, it becomes no longer necessary to secure a space corresponding to the length of the guide section 451 of the rod-shaped guide 450 in the oral cavity when mounting the dental drill 500 onto the rod-shaped guide 450, by providing the incision 511 on the dental drill 500. Thereby, strain on a patient of needing to open the mouth wide during an implant treatment can be further alleviated in comparison to the dental drill of Embodiment 4 or Variant 1 thereof. In particular, such an advantage is prominent when a section positioned deep in the oral cavity where the spatial dimension that can be secured is limited is the targeted site for an implant embedding hole.

As explained above, the present invention can form an implant embedding hole for embedding a fixture in an appropriate position and direction. Furthermore, it is possible to obtain a dental drill that renders opening the mouth wide by a patient unnecessary when forming an implant embedding hole.

Needless to say, the above-described Variants can be appropriately combined with one another.

Further, the present invention is of course not limited to the above-described Embodiments, and the present invention can be altered in various ways and practiced within the scope that does not deviate from the purport of the present invention.

As described above, the present invention is exemplified by the use of preferred embodiments of the present invention. However, the present invention should not be interpreted solely based on the embodiments. It is understood that the scope of the present invention should be interpreted solely based on the claims. It is also understood that those skilled in the art can implement equivalent scope of technology, based on the description of the present invention and common knowledge from the description of the detailed preferred embodiments of the present invention. Furthermore, it is understood that any patent, any patent application and any references cited in the present specification should be incorporated by reference in the present specification in the same manner as the contents are specifically described therein.

INDUSTRIAL APPLICABILITY

In the field of abutments, fixtures, dental implant sets, dental taps, dental guides, dental tap sets, and dental drills, the present invention can enhance workability and safety of an implant treatment and alleviate strain on a patient in the implant treatment. In addition, the present invention is for providing a dental implant and a dental instrument for enhancing workability and safety of the implant treatment and alleviating strain on a patient in the implant treatment.

In particular, use of the dental implant set of the present invention allows an operation of detaching an abutment from a fixture to be readily performed without having a patient open his/her mouth wide while inhibiting accidental ingestion or swallowing of an abutment that comes off from occurring.

Use of the dental drill of the present invention enables the formation of an implant embedding hole for embedding a fixture in an appropriate position and direction and renders having a patient open his/her mouth wide open unnecessary when forming an implant embedding hole.

Furthermore, use of the dental tap set of the present invention enables a fixture to be screwed into a jawbone with non-uniform hardness without misalignment.

Thus, the present invention provides a technique directed to a dental implant and a dental instrument that enable an implant treatment for replacing a natural tooth that is lost from tooth decay, periodontal disease or the like with an artificial tooth with appearance and functions that are no different from the natural tooth.

REFERENCE SIGNS LIST 20 jawbone (alveolar bone)
20a implant embedding hole
20a1 screw groove
21 gums
31 maxillary alveolar bone
32 mucous membrane
33 maxillary sinus
34, 34a cortical bone
35 tap pilot hole (implant embedding hole)
36 mucous membrane of the maxillary sinus (Schneiderian membrane)
37 artificial bone
80 remover device
80a device body
80b arm section
80c fit disengaging rod (remover)
81a fit disengaging rod
81a1 rod tip 81a2 rod body
100, 200 dental implant
110, 110a, 210 fixture
112 fixture head
112a truncated conical section (outer tapered section)
112b hexagonal prism section
112b1 top surface of fixture head (top surface of hexagonal prism section)
113 IC chip
114 outer circumferential surface
120, 120b, 1000 abutment
121, 1121 fitting recess
121a circular groove section (inner tapered section)
121b hexagonal groove section
121c fitting recess sidewall
123 longitudinal hole
125 inner circumferential surface
129 instrument insertion hole (transverse hole)
129b1 opening
129b2 interior section
130 artificial tooth (restoration)
200s dental implant set
210a existing fixture
220 abutment
220a existing abutment
230 artificial tooth (restoration)
240 stent
241 insertion hole
242 recess
250 securing pin
260 drill
300, 500 dental drill
310, 510 drill body
311, 510a throughhole
313, 512 drilling blade
310a outer circumferential surface
312, 514 helical protruding line
320, 520 drill support
350, 450 rod-shaped guide
351, 451 guide section
352, 452 embedding section
410, 410a, 410b, 410c, 410d dental tap
411 tap body
411a screw thread (mail screw)
411b spiral groove
412 tap holding section
413, 413a, 413b, 413c, 413d cutting section
420 dental guide
420a guide hole
421 screw groove
511 incision
513 water pouring hole
1120 abutment section
1130 linking section
D1 drill
D dental drill
Dc drill chuck
Dh, Dh1-Dh3 drill head
Gh guide hole
Gs guide sleeve
S space
SG guide member (surgical guide)
Ta dental tap

The invention claimed is:

1. An abutment for a dental implant, comprising
a fitting recess for fitting onto a head of a fixture configured to couple with a jawbone,
wherein the head of the fixture is secured to the fitting recess by a frictional force that is generated between an outside surface of the head of the fixture and an inside surface of the fitting recess when the head of the fixture fits into the fitting recess so that a space is formed between a top surface of the head of the fixture and a bottom surface of the fitting recess, and
an instrument insertion hole for inserting, in the space, an instrument for disengaging the fitting recess secured to the head of the fixture by the frictional force, is formed on a sidewall of the fitting recess.

2. The abutment according to claim 1, wherein
the fitting recess has a structure in which at least a part of the inside surface of the fitting recess tightly contacts the outside surface of the head of the fixture so that an object that enters the fitting recess from the instrument insertion hole does not seep out toward the jawbone.

3. The abutment according to claim 1, wherein
the fitting recess has a shape that matches a shape of the head of the fixture so that a rotation of the abutment with respect to the fixture is restricted when the head of the fixture fits into the fitting recess.

4. The abutment according to claim 1, wherein the inside surface of the fitting recess is tilted with respect to an insertion direction of the head of the fixture to the fitting recess to conform to the outside surface of the head of the fixture.

5. An abutment for a dental implant, comprising
a plurality of fitting recesses for fitting onto a plurality of heads of fixtures configured to couple with a jawbone,
wherein adjacent fitting recesses among the plurality of fitting recesses are linked to each other by a linking section,
each of the plurality of heads of fixtures is secured to a corresponding fitting recess by a frictional force that is generated between an outside surface of each of the plurality of heads of fixtures and an inside surface of the corresponding fitting recess when each of the plurality of fitting recesses fits onto the head of a corresponding fixture so that a space is formed between a bottom surface of each of the plurality of fitting recesses and a top surface of the head of the corresponding fixture, and
an instrument insertion hole for inserting an instrument for disengaging the fitting recess secured to the head of the fixture by the frictional force in the space, is formed on at least one sidewall of the plurality of fitting recesses.

6. The abutment according to claim 5, wherein the fitting recess is configured such that a space is created between portions other than an edge section on an opening side of the inside surface of the fitting recess and the outside surface of the head of the fixture when the head of the fixture is inserted in the fitting recess.

7. A dental implant set comprising a fixture configured to couple with a jawbone and an abutment for supporting an artificial tooth,
wherein the fixture comprises an embedded section that is embedded in the jawbone and a head for securing the abutment,
the abutment comprises a fitting recess for fitting onto the head of the fixture,
the head of the fixture is secured to the fitting recess of the abutment by a frictional force that is generated between an outside surface of the head of the fixture and an inside surface of the fitting recess of the abutment when the head of the fixture fits into the fitting recess of the abutment so that a space is formed between a top surface of the head of the fixture and a bottom surface of the fitting recess of the abutment, and an instrument insertion hole for inserting an instrument for disengaging the fitting recess of the abutment secured to the head of the fixture by the frictional force in the space, is formed on a sidewall of the fitting recess of the abutment.

8. The dental implant set according to claim 7, further comprising a stent having a recess and a securing pin for securing the stent, wherein the abutment comprises a top portion onto which the recess of the stent fits and an insertion hole for receiving the securing pin, the fixture comprises an insertion hole for receiving the securing pin, and the stent is configured such that a posture of the stent when the recess of the stent fits onto the top portion of the abutment attached to the fixture defines a direction of the fixture.

9. The dental implant set according to claim 8, wherein the securing pin is configured to be inserted through the fixture and the abutment secured to the head of the fixture.

10. The dental implant set according to claim 7, wherein the fixture consists of two components, which are a first component constituting the head and a second component constituting the embedded section; and the head and the embedded section are configured to be fastened by threadedly engaging a male screw section formed on the first component with a female screw section formed on the second component.

11. The dental implant set according to claim 7, wherein the head comprises an IC chip that stores data related to history of the dental implant.

12. The dental implant set according to claim 10, wherein the head comprises an IC chip that stores data related to history of the dental implant.

* * * * *